(12) United States Patent
Uesugi et al.

(10) Patent No.: US 9,085,566 B2
(45) Date of Patent: Jul. 21, 2015

(54) COMPOSITIONS AND METHODS FOR THE TREATMENT OF METABOLIC AND RELATED DISORDERS

(71) Applicants: Motonari Uesugi, Osaka (JP); Salih J. Wakil, Houston, TX (US); Lutfi Abu-Elheiga, Houston, TX (US); Mizuki Watanabe, Kyoto (JP)

(72) Inventors: Motonari Uesugi, Osaka (JP); Salih J. Wakil, Houston, TX (US); Lutfi Abu-Elheiga, Houston, TX (US); Mizuki Watanabe, Kyoto (JP)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 14/013,918

(22) Filed: Aug. 29, 2013

(65) Prior Publication Data

US 2014/0038984 A1 Feb. 6, 2014

Related U.S. Application Data

(63) Continuation-in-part of application No. 13/484,702, filed on May 31, 2012, now Pat. No. 8,927,578, which is a continuation of application No. 12/024,530, filed on Feb. 1, 2008, now Pat. No. 8,207,196.

(60) Provisional application No. 61/012,310, filed on Dec. 7, 2007, provisional application No. 60/887,994, filed on Feb. 2, 2007.

(51) Int. Cl.
| | |
|---|---|
| *A61K 31/427* | (2006.01) |
| *A61K 31/4025* | (2006.01) |
| *C07D 417/04* | (2006.01) |
| *C07D 403/04* | (2006.01) |
| *A61K 31/4439* | (2006.01) |
| *C07D 277/24* | (2006.01) |
| *A61K 31/426* | (2006.01) |
| *C07D 213/16* | (2006.01) |
| *A61K 31/4418* | (2006.01) |
| *A61K 31/454* | (2006.01) |
| *C07D 213/76* | (2006.01) |
| *A61K 31/496* | (2006.01) |
| *C07D 235/14* | (2006.01) |
| *C07D 417/12* | (2006.01) |
| *A61K 45/06* | (2006.01) |
| *C07D 417/14* | (2006.01) |
| *C07D 277/22* | (2006.01) |
| *C07D 471/04* | (2006.01) |
| *C07D 487/04* | (2006.01) |
| *C07D 277/52* | (2006.01) |

(52) U.S. Cl.
CPC ............ *C07D 417/04* (2013.01); *A61K 31/426* (2013.01); *A61K 31/4418* (2013.01); *A61K 31/4439* (2013.01); *A61K 31/454* (2013.01); *A61K 31/496* (2013.01); *A61K 45/06* (2013.01); *C07D 213/16* (2013.01); *C07D 213/76* (2013.01); *C07D 235/14* (2013.01); *C07D 277/22* (2013.01); *C07D 277/24* (2013.01); *C07D 277/52* (2013.01); *C07D 417/12* (2013.01); *C07D 417/14* (2013.01); *C07D 471/04* (2013.01); *C07D 487/04* (2013.01)

(58) Field of Classification Search
CPC .. C07D 417/04; C07D 403/04; A61K 31/427; A61K 31/4025
See application file for complete search history.

(56) References Cited

U.S. PATENT DOCUMENTS

| | | | |
|---|---|---|---|
| 4,791,200 A | 12/1988 | Press et al. | |
| 5,643,932 A | 7/1997 | Chihiro et al. | |
| 7,151,196 B2 | 12/2006 | Wilkening et al. | |
| 7,153,889 B2 | 12/2006 | Altenbach et al. | |
| 2003/0069223 A1* | 4/2003 | Jacobs et al. ............. | 514/211.01 |
| 2006/0229363 A1 | 10/2006 | Hamanaka | |

FOREIGN PATENT DOCUMENTS

| | | |
|---|---|---|
| EP | 0513387 B1 | 11/1992 |
| EP | 1092711 A1 | 4/2001 |
| EP | 1348706 A1 | 10/2003 |
| JP | 11186479 A | 6/1999 |
| WO | 9814191 A1 | 4/1998 |
| WO | 0106261 A2 | 1/2001 |
| WO | 02068417 A2 | 9/2002 |
| WO | 2006017384 A2 | 2/2006 |
| WO | 2006080406 A1 | 8/2006 |
| WO | 2007001973 A1 | 1/2007 |
| WO | 2013110007 A1 | 7/2013 |

OTHER PUBLICATIONS

Bilgin, et al. 2-Pyridylthiazoles II synthesis and structure elucidations, Acta Pharmaceutica Turcica, 1999;vol. 30:133-137.
Choi, et al. Identification of bioactive molecules by adipogenesis profiling of organic compounds, J Biol Chem, Feb. 28, 2003;vol. 278(9);7320-7324.
Ide, et al. Sesamin, a sesame lignin, decreases fatty acid synthesis in rat liver accompanying the down-regulation of sterol regulatory element binding protein-1, Biochemica et Biophysica Acta, 2001;1534:1-13.
Kamisuki, et al. A small molecule that blocks fat synthesis by inhibiting the activation of SREBP, Chemistry & Biology, 2009;16:882-892.

(Continued)

*Primary Examiner* — Yong Chu
(74) *Attorney, Agent, or Firm* — Benjamin Aaron Adler

(57) ABSTRACT

The present invention relates to the compound for treatment and/or prevention of one or more metabolic disorders utilizes an A-B-C tripartite structure, wherein A, B, and C are identical or non-identical structures, for example, but not limited to, heterocyclic, phenyl or benzyl ring structures with or without substitutions and are described in detail herein. Also provided are methods for the treatment and/or prevention of one or more metabolic disorders, for example, obesity or diabetes, utilizing fatostatin A and/or a derivative and/or analog thereof and/or the A-B-C tripartite compounds.

9 Claims, 35 Drawing Sheets

(56) References Cited

OTHER PUBLICATIONS

Kamisuki, et al. Synthesis and elevation of diarylthiazole derivatives that inhibit activation of sterol regulatory element-binding proteins, J Med Chem, 2011;54(13):4923-4927.

Sanfillippo, et al. Synthesis of (aryloxy)alkylamines. 1. Novel antisecretory agents with H+K+-ATPase inhibitory activity, J Med Chem, 1988;31:1778-1785.

Vachal, et al. Highly selective and potent agonists of sphingosine-1-phosphate 1 (S1P1) receptor, Bioorg Medchem Lett, 2006;16:3684-3687.

Reilly, et al. Proceedings of the Nutritioin Society 2003;vol. 62, pp. 611-619.

Pinent, et al. Int J Obesity, 2005;29:934-941.

Das, et al. A rapid and high-yielding synthesis of thiazoles and aminothiazoles using ammonium-12-molybdophosphate, J Mol Catal A, Jun. 2006;252:235-237.

Uesugi, M Organic compounds that control SREBP activities, Ikagaku Oyo Kenkyu Zaidan Kenkyu Hokoku, 2006;25:168-172.

Chihiro, et al. Novel thiazole derivatives as inhibitors of superoxide production by human neutrophils: synthesis and structure-activity relationships, J Med Chem 1995;38:353-358.

* cited by examiner

|  | Fold Decreased | |
| --- | --- | --- |
|  | Microarray | RT-PCR |
| ATP | 0.57 | 0.47 |
| HMG CoAR | 0.50 | 0.54 |
| LDLR | 0.61 | 0.58 |
| MVD | 0.32 | 0.50 |
| SCD | 0.57 | 0.47 |
| INSIG1 | 0.32 | 0.64 |
| GAPDH | 1.00 | 0.92 |

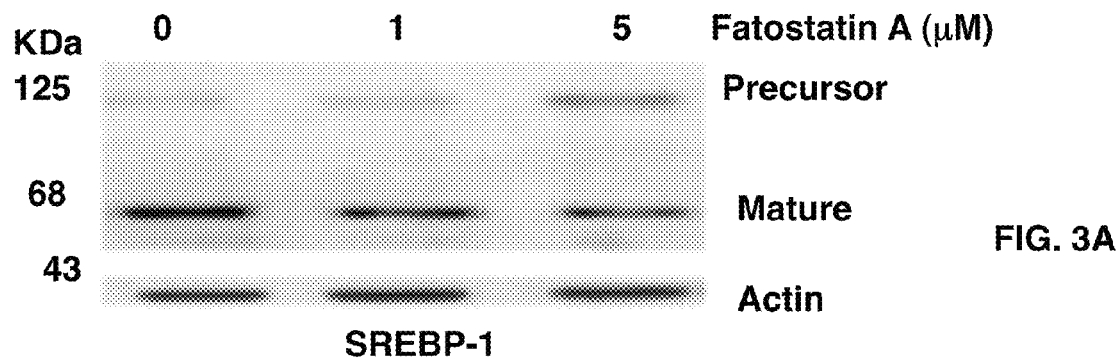
FIG. 3A
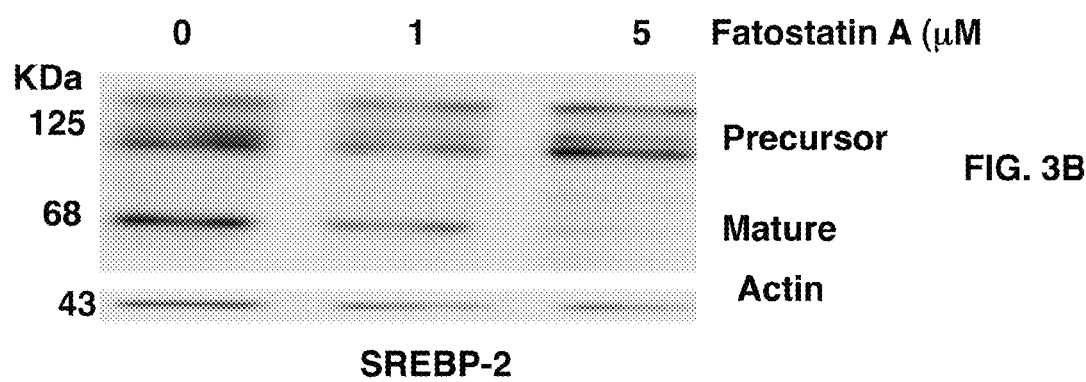
FIG. 3B
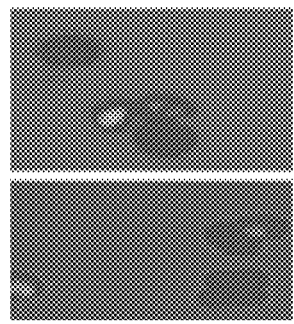
FIG. 3C
DAPI
FIG. 3F
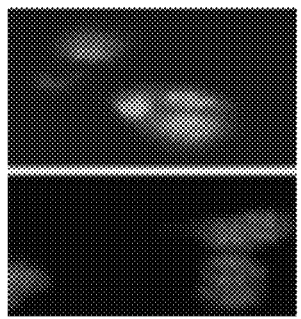
FIG. 3D
SREBP-1
FIG. 3G
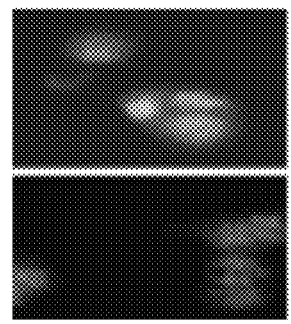
FIG. 3E
MERGE
FIG. 3H

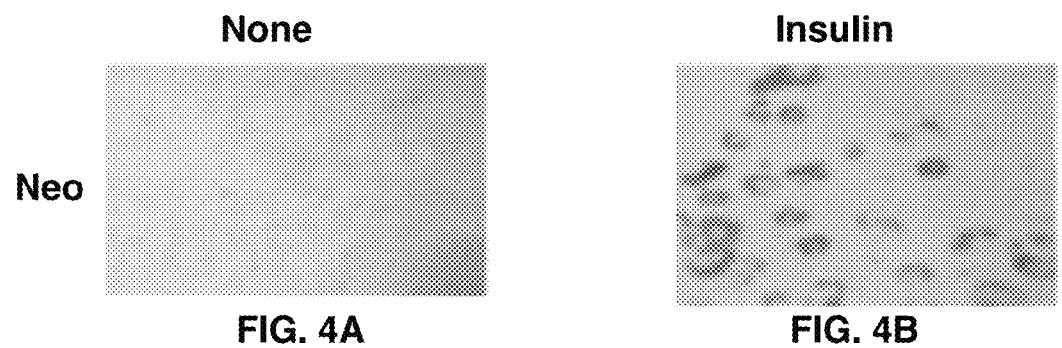
| None | Insulin |
|---|---|
| FIG. 4A | FIG. 4B |
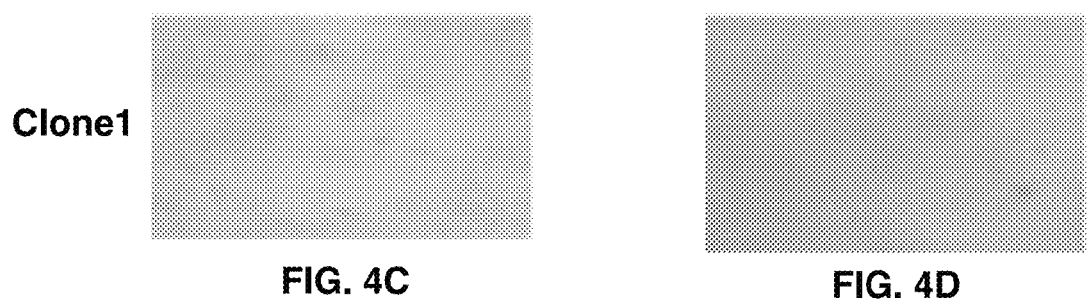
| FIG. 4C | FIG. 4D |
|---|---|
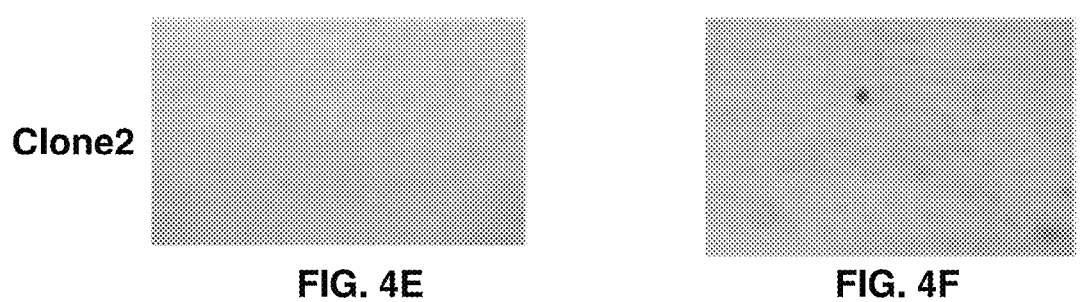
| FIG. 4E | FIG. 4F |
|---|---|
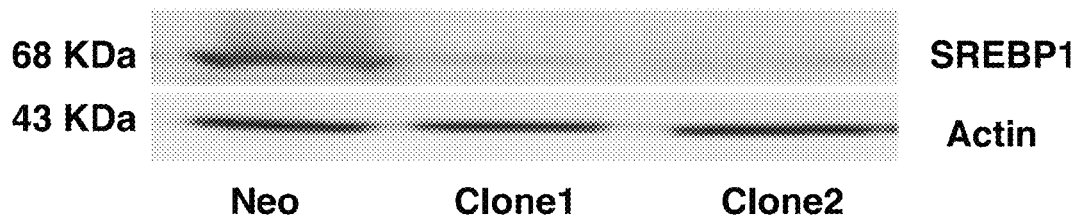
FIG. 4G ■ Fatostatin A
□ Control

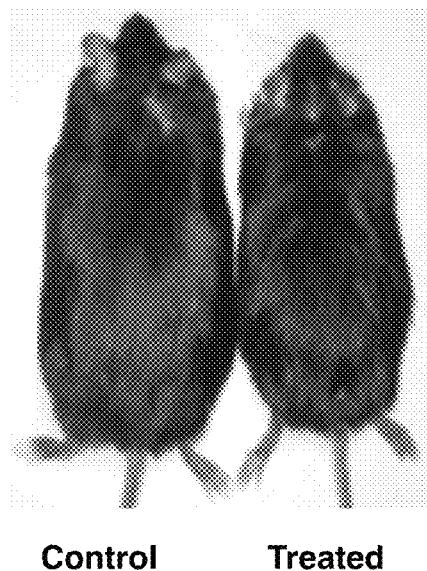
Control    Treated
FIG. 8A
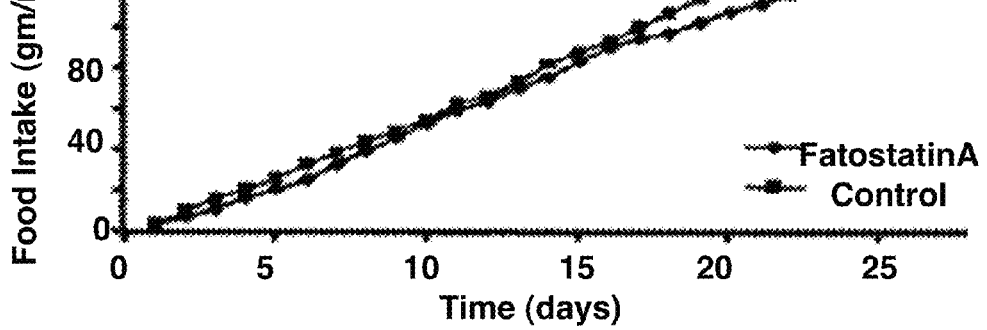
FIG. 8B
FIG. 8C

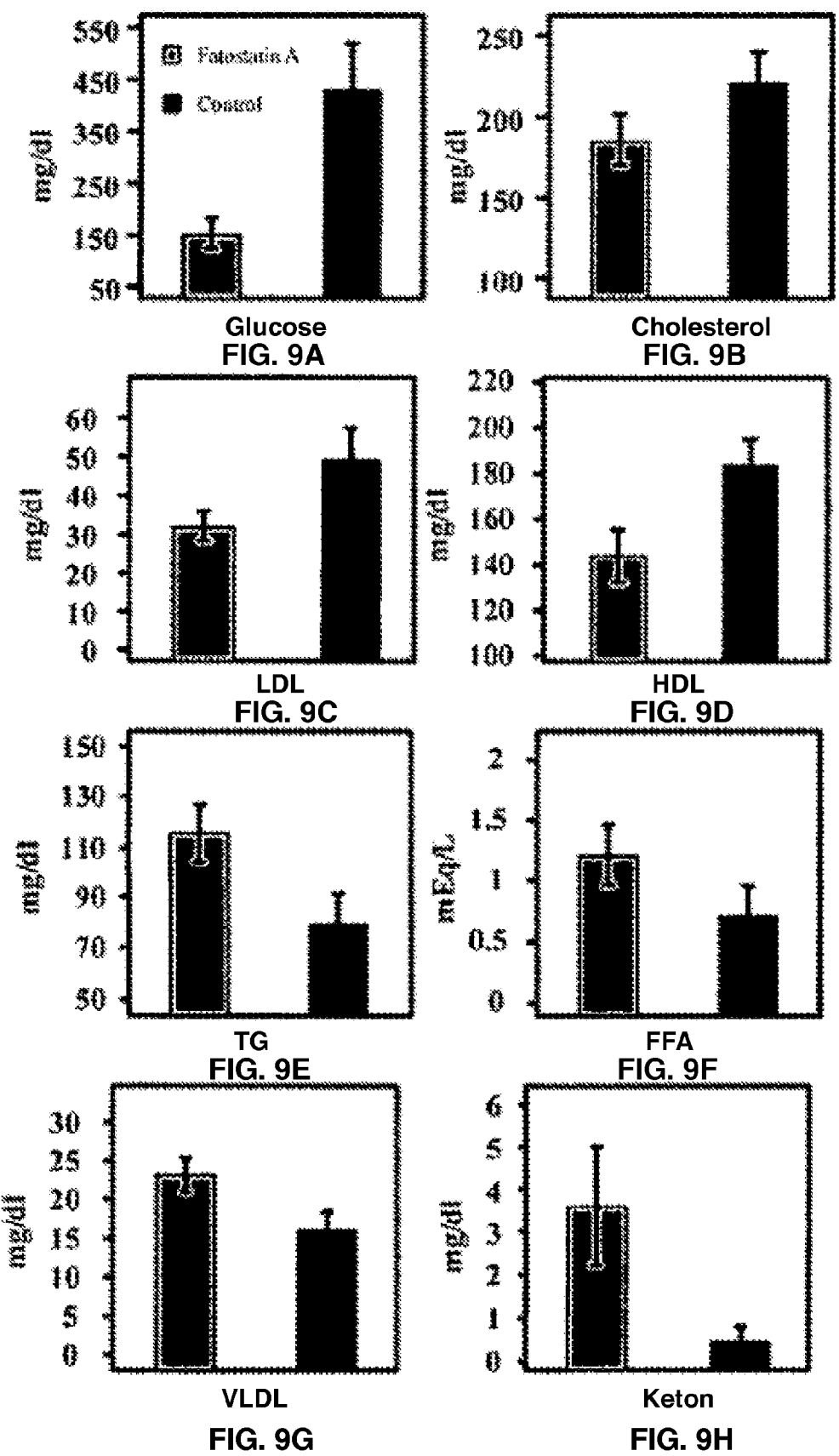
FIG. 9A Glucose
FIG. 9B Cholesterol
FIG. 9C LDL
FIG. 9D HDL
FIG. 9E TG
FIG. 9F FFA
FIG. 9G VLDL
FIG. 9H Keton

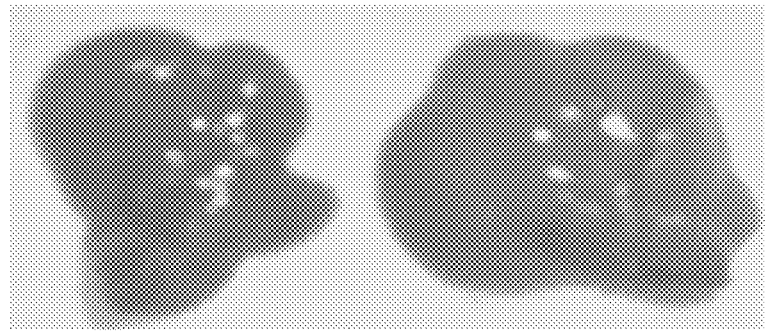
Fatostatin A        control
FIG. 10A
Fatostatin A
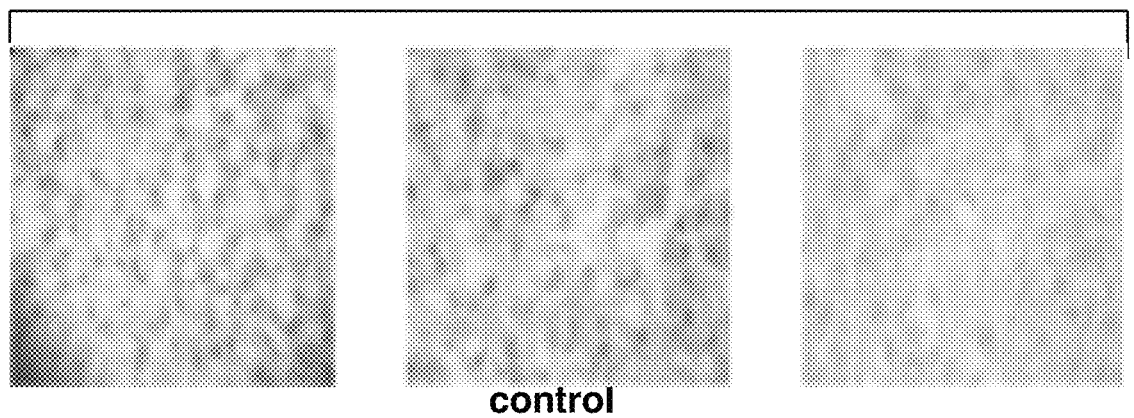
control
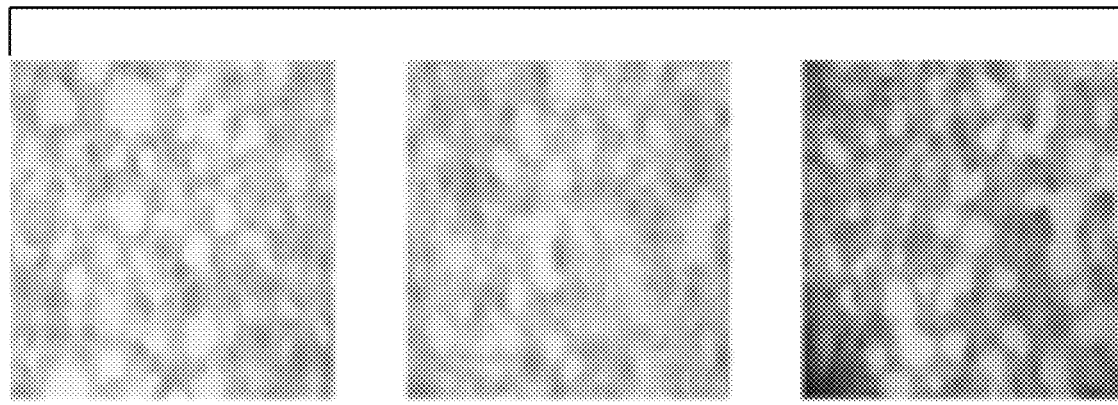
FIG. 10B

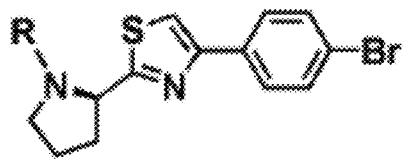
45: R=H
46: R=n-Pr
47: R=Boc
48: R=Cbz
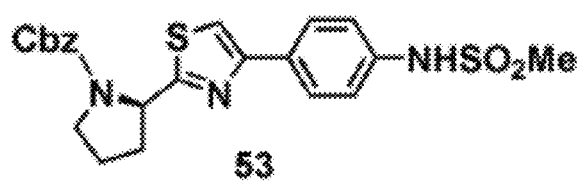
53
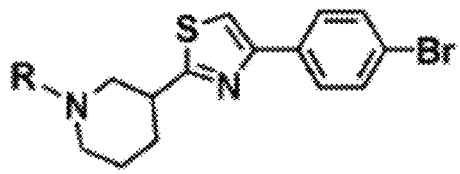
49: R=n-Pr
50: R=Boc
51: R=Cbz
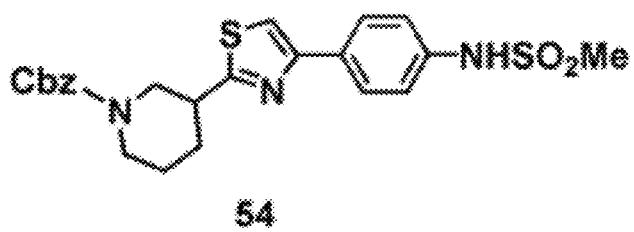
54
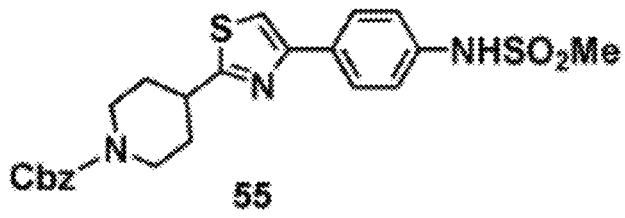
55
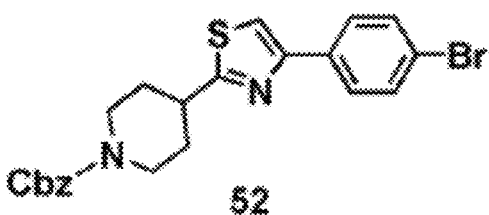
52
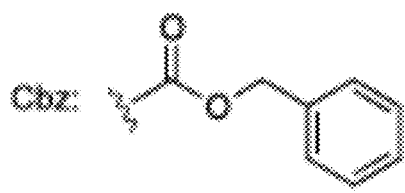
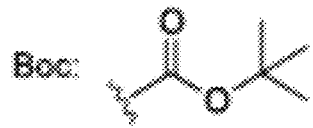
FIG. 14C

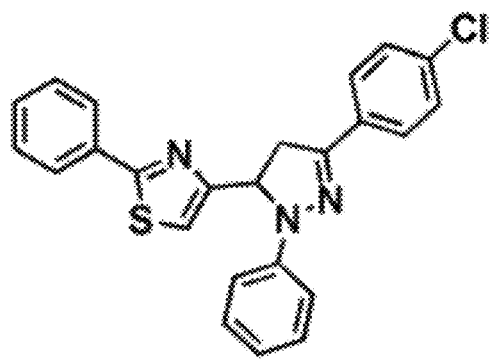
64
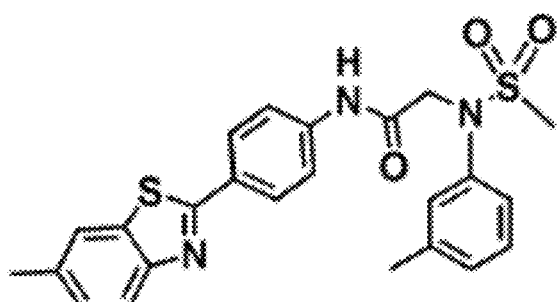
65
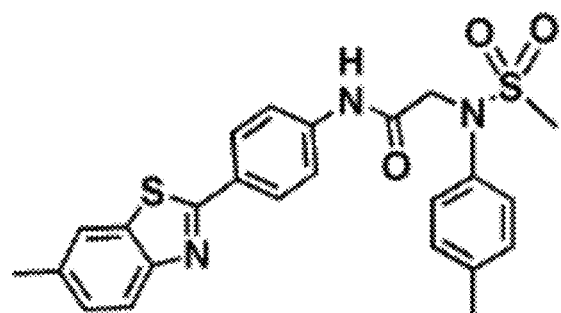
66
FIG. 14F

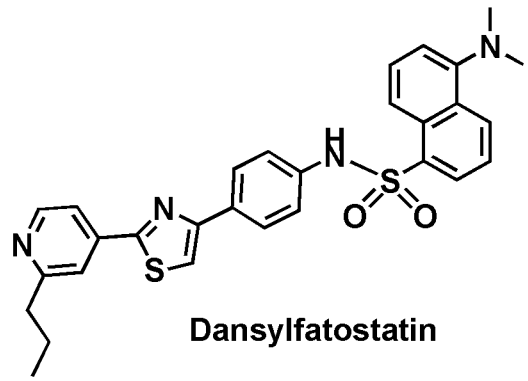
Dansylfatostatin
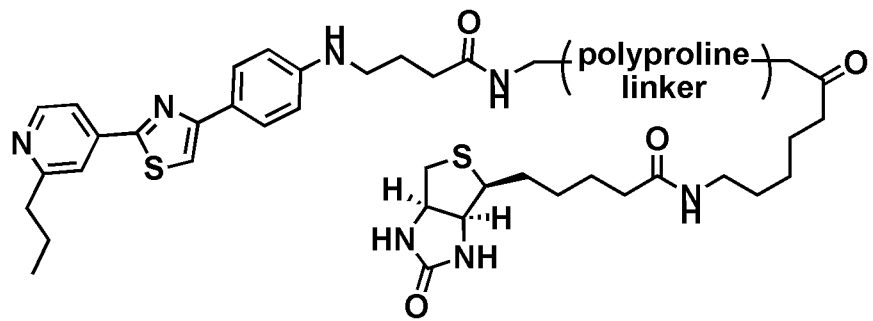
Fatostatin-polyproline linker-biotin conjugate
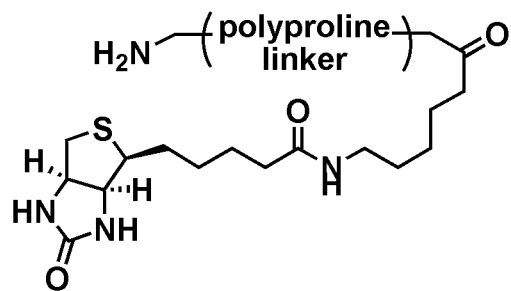
polyproline linker-biotin conjugate
FIG 20A Reagents: a) EtOH; b) benzophenone imine, Pd$_3$dba$_3$, BINAP, NaOtBu, toluene; c) HCl aq, THF; d) dansyl chloride, pyridine, CH$_2$CL$_2$; e) (Boc)$_2$O, DMAP, THF; f) Ethyl 4-bromobutyrate, NaI, NaH, DMF; g) NaOH aq, THF, MeOH; h) iPrNH$_2$, Et$_3$N, HATU, DMF; i) TFA, THF, j) resin-polypropyline diisopropylcarbodiimide, NMP; k) TFA, Ethanedithiol, thioanisol, PhOH, H$_2$O

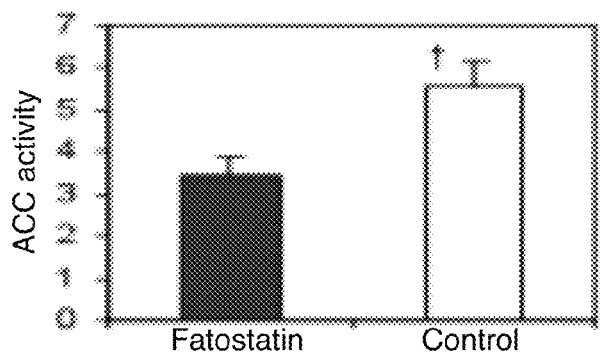
FIG. 25A
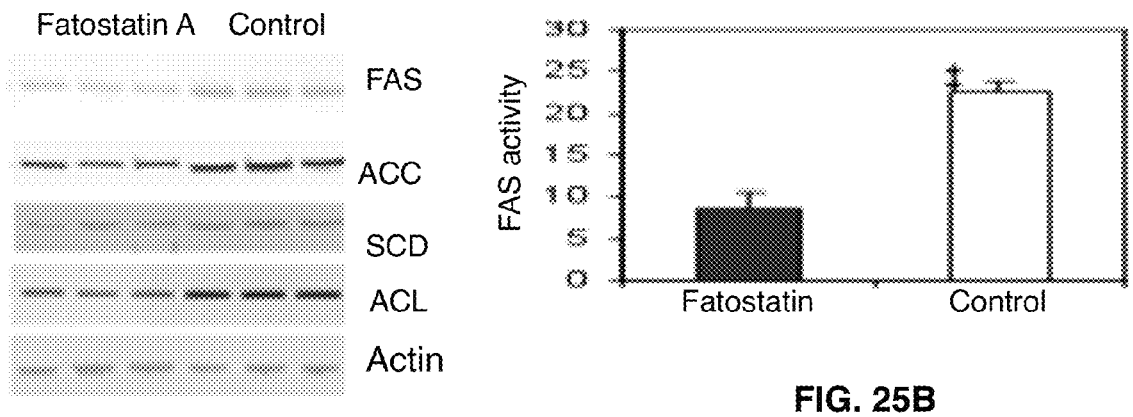
FIG. 25C
FIG. 25B
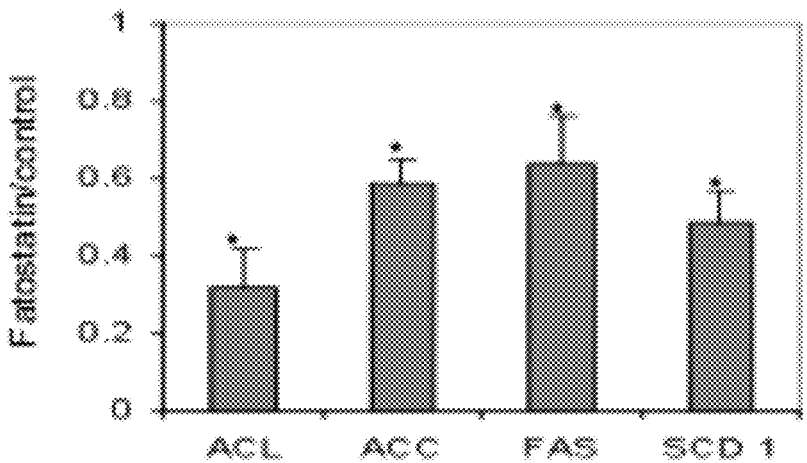
FIG. 25D

Reagents and conditions: a) EtOH, 70°C; b) benzophenone imine, Pd$_2$(dba)$_3$, BINAP, NaOtBu, toluene, reflux; c) HCl aq, THF; d) MsCl, pyridine, CH$_2$Cl$_2$, 0°C

```
                        SEQUENCE LISTING

<160> NUMBER OF SEQ ID NOS: 27

<210> SEQ ID NO 1
<211> LENGTH: 30
<212> TYPE: DNA
<213> ORGANISM: Artificial Sequence
<220> FEATURE:
<223> OTHER INFORMATION: primer for low density lipoprotein receptor

<400> SEQUENCE: 1
tcagaccggg actgcttgga cggctcagtc                                          30

<210> SEQ ID NO 2
<211> LENGTH: 28
<212> TYPE: DNA
<213> ORGANISM: Artificial Sequence
<220> FEATURE:
<223> OTHER INFORMATION: primer for low density lipoprotein receptor

<400> SEQUENCE: 2
ccacttaggc agtggaactc gaaggccg                                            28

<210> SEQ ID NO 3
<211> LENGTH: 21
<212> TYPE: DNA
<213> ORGANISM: Artificial Sequence
<220> FEATURE:
<223> OTHER INFORMATION: primer for stearoyl-CoA desaturase

<400> SEQUENCE: 3
gcctgcttga taatatataa a                                                   21

<210> SEQ ID NO 4
<211> LENGTH: 19
<212> TYPE: DNA
<213> ORGANISM: Artificial Sequence
<220> FEATURE:
<223> OTHER INFORMATION: primer for stearoyl-CoA desaturase

<400> SEQUENCE: 4
cacttgaatt gagctttag                                                      19

<210> SEQ ID NO 5
<211> LENGTH: 23
<212> TYPE: DNA
<213> ORGANISM: Artificial Sequence
<220> FEATURE:
<223> OTHER INFORMATION: primer for ATP citrate lyase
```

```
<400> SEQUENCE: 5
aagaaaaagt gtcagacagc tgg                                           23

<210> SEQ ID NO 6
<211> LENGTH: 20
<212> TYPE: DNA
<213> ORGANISM: Artificial Sequence
<220> FEATURE:
<223> OTHER INFORMATION: primer for ATP citrate lyase

<400> SEQUENCE: 6
tggactgaag gggtgttagc                                               20

<210> SEQ ID NO 7
<211> LENGTH: 24
<212> TYPE: DNA
<213> ORGANISM: Artificial Sequence
<220> FEATURE:
<223> OTHER INFORMATION: primer for 3-hydroxy-3-methylglutaryl-CoA
      reductase

<400> SEQUENCE: 7
gcccgacagt tctgaactgg aaca                                          24

<210> SEQ ID NO 8
<211> LENGTH: 24
<212> TYPE: DNA
<213> ORGANISM: Artificial Sequence
<220> FEATURE:
<223> OTHER INFORMATION: primer for 3-hydroxy-3-methylglutaryl-CoA
      reductase

<400> SEQUENCE: 8
gaacctgaga cctctctgaa agag                                          24

<210> SEQ ID NO 9
<211> LENGTH: 18
<212> TYPE: DNA
<213> ORGANISM: Artificial Sequence
<220> FEATURE:
<223> OTHER INFORMATION: primer for mevalonate kinase

<400> SEQUENCE: 9
ctgcctgact gcctcagc                                                 18

<210> SEQ ID NO 10
<211> LENGTH: 19
<212> TYPE: DNA
<213> ORGANISM: Artificial Sequence
<220> FEATURE:
<223> OTHER INFORMATION: primer for mevalonate kinase

<400> SEQUENCE: 10
acctctcctg acacctggg                                                19

<210> SEQ ID NO 11
<211> LENGTH: 22
<212> TYPE: DNA
<213> ORGANISM: Artificial Sequence
<220> FEATURE:
<223> OTHER INFORMATION: primer for insulin-induced gene 1

<400> SEQUENCE: 11
aagacttcag ggtaagtcat ca                                            22
```

<210> SEQ ID NO 12
<211> LENGTH: 22
<212> TYPE: DNA
<213> ORGANISM: Artificial Sequence
<220> FEATURE:
<223> OTHER INFORMATION: primer for insulin-induced gene 1

<400> SEQUENCE: 12
cgtgtataat ggtgtctatc ag                                        22

<210> SEQ ID NO 13
<211> LENGTH: 64
<212> TYPE: DNA
<213> ORGANISM: Artificial Sequence
<220> FEATURE:
<223> OTHER INFORMATION: oligonucleotide derived from SREBP-1 gene

<400> SEQUENCE: 13
gatccccgcc acattgagct cctctcttca agagagagag gagctcaatg           50
tggctttttg gaaa                                                  64

<210> SEQ ID NO 14
<211> LENGTH: 63
<212> TYPE: DNA
<213> ORGANISM: Artificial Sequence
<220> FEATURE:
<223> OTHER INFORMATION: oligonucleotide derived from SREBP-1 gene

<400> SEQUENCE: 14
agcttttcca aaaagccaca ttgagctcct ctctctcttg aaggaggagc           50
tcaatgtggc ggg                                                   63

<210> SEQ ID NO 15
<211> LENGTH: 22
<212> TYPE: PRT
<213> ORGANISM: Artificial Sequence
<220> FEATURE:
<223> OTHER INFORMATION: polyproline linker sequence

<400> SEQUENCE: 15

Lys Pro Gly Gln Phe Leu Tyr Glu Leu Lys Lys Pro Pro Pro Pro
1               5                   10                  15
Pro Pro Pro Pro Lys Lys
            20

<210> SEQ ID NO 16
<211> LENGTH: 30
<212> TYPE: DNA
<213> ORGANISM: Artificial Sequence
<220> FEATURE:
<223> OTHER INFORMATION: primer for low density lipoprotein receptor

<400> SEQUENCE: 16
tcagaccggg actgcttgga cggctcagtc                                30

<210> SEQ ID NO 17
<211> LENGTH: 25
<212> TYPE: DNA
<213> ORGANISM: Artificial Sequence
<220> FEATURE:
<223> OTHER INFORMATION: primer for low density lipoprotein receptor

<400> SEQUENCE: 17
cttaggcagt ggaactcgaa ggccg                                     25

<210> SEQ ID NO 18
<211> LENGTH: 22
<212> TYPE: DNA
<213> ORGANISM: Artificial Sequence
<220> FEATURE:
<223> OTHER INFORMATION: primer for stearoyl-CoA desaturase

<400> SEQUENCE: 18
gcctgcttga taatatataa ac                                              22

<210> SEQ ID NO 19
<211> LENGTH: 19
<212> TYPE: DNA
<213> ORGANISM: Artificial Sequence
<220> FEATURE:
<223> OTHER INFORMATION: primer for stearoyl-CoA desaturase

<400> SEQUENCE: 19
cacttgaatt gagctttag                                                  19

<210> SEQ ID NO 20
<211> LENGTH: 23
<212> TYPE: DNA
<213> ORGANISM: Artificial Sequence
<220> FEATURE:
<223> OTHER INFORMATION: primer for ATP citrate lyase

<400> SEQUENCE: 20
aagaaaaagt gtcagacagc tgg                                             23

<210> SEQ ID NO 21
<211> LENGTH: 20
<212> TYPE: DNA
<213> ORGANISM: Artificial Sequence
<220> FEATURE:
<223> OTHER INFORMATION: primer for ATP citrate lyase

<400> SEQUENCE: 21
tggactgaag gggtgttagc                                                 20

<210> SEQ ID NO 22
<211> LENGTH: 24
<212> TYPE: DNA
<213> ORGANISM: Artificial Sequence
<220> FEATURE:
<223> OTHER INFORMATION: primer for 3-hydroxy-3-methylglutaryl-CoA
      reductase

<400> SEQUENCE: 22
gcccgacagt tctgaactgg aaca                                            24

<210> SEQ ID NO 23
<211> LENGTH: 24
<212> TYPE: DNA
<213> ORGANISM: Artificial Sequence
<220> FEATURE:
<223> OTHER INFORMATION: primer for 3-hydroxy-3-methylglutaryl-CoA
      reductase

<400> SEQUENCE: 23
gaacctgaga cctctctgaa agag                                            24

<210> SEQ ID NO 24
<211> LENGTH: 18
<212> TYPE: DNA

```
<213> ORGANISM: Artificial Sequence
<220> FEATURE:
<223> OTHER INFORMATION: primer for mevalonate pyrophosphate
      decarboxylase

<400> SEQUENCE: 24
ctgcctgact gcctcagc                                                 18

<210> SEQ ID NO 25
<211> LENGTH: 19
<212> TYPE: DNA
<213> ORGANISM: Artificial Sequence
<220> FEATURE:
<223> OTHER INFORMATION: primer for mevalonate pyrophosphate
      decarboxylase

<400> SEQUENCE: 25
acctctcctg acacctggg                                                19

<210> SEQ ID NO 26
<211> LENGTH: 22
<212> TYPE: DNA
<213> ORGANISM: Artificial Sequence
<220> FEATURE:
<223> OTHER INFORMATION: primer for insulin-induced gene 1

<400> SEQUENCE: 26
aagacttcag ggtaagtcat ca                                            22

<210> SEQ ID NO 27
<211> LENGTH: 22
<212> TYPE: DNA
<213> ORGANISM: Artificial Sequence
<220> FEATURE:
<223> OTHER INFORMATION: primer for insulin-induced gene 1

<400> SEQUENCE: 27
cgtgtataat ggtgtctatc ag                                            22
```

COMPOSITIONS AND METHODS FOR THE TREATMENT OF METABOLIC AND RELATED DISORDERS

CROSS-REFERENCE TO RELATED APPLICATIONS

This application is a continuation-In-part under 35 U.S.C. §120 of pending application U.S. Ser. No. 13/484,702, filed May 31, 2012, which is a continuation of application U.S. Ser. No. 12/024,530, filed Feb. 1, 2008, now U.S. Pat. No. 8,207,196, which is a non-provisional application under 35 U.S.C §119(e) of provisional application U.S. Ser. No. 61/012,310, filed Dec. 7, 2007, and of provisional application U.S. Ser. No. 60/887,994, filed Feb. 2, 2007, the entirety of all of which are hereby incorporated by reference.

FEDERAL FUNDING LEGEND

The present invention utilized federal funding from the National Institutes of Health Grant GM-63115 and Department of Defense Grant No. DAMD17-03-1-0228. The United States Government has certain rights in the invention.

BACKGROUND OF THE INVENTION

1. Field of the Invention

The present invention generally relates to the fields of medicine and molecular biology of metabolic disorders. In particular aspects, the field of the invention relates to particular compositions for the treatment of a metabolic disorder, such as obesity. In certain aspects, the compositions comprise fatostatin A and its analogs or derivatives.

2. Description of the Related Art

Metabolic syndrome covers many cardiovascular risk factors including hypertension, dyslipidaemia, obesity, type 2 diabetes, pancreatic β-cell dysfunction, and atherosclerosis. A diet varying in fat or carbohydrate contents contributes to energy metabolism of animals including humans. Long chain fatty acids are major source of energy and important components of the lipids that comprise the cellular membranes. They are derived from food and synthesized de novo from acetyl-CoA. Cholesterol is also derived from food and synthesized from acetyl-CoA. The conversion of carbohydrates into acylglycerides through de novo fatty acid and cholesterol synthesis involves at least 12 and 23 enzymatic reactions, respectively. Expression levels of the genes encoding these enzymes are controlled by three transcription factors, designated sterol regulatory element-binding proteins (SREBPs), SREBP-1a, -1c and SREBP-2 (Brown and Goldstein, 1997; Osborne, 2000). These membrane-bound proteins are members of a class of the basic helix-loop-helix leucin zipper family of transcription factors (Brown and Goldstein, 1997; Osborne, 2000; Tontonoz et al., 1993). Unlike other leucin zipper members of transcription factors, SREBPs are synthesized as an ER-membrane-bound precursor, which needs to be proteolytically released by two proteases bound to the Golgi membrane, Site-1 and Site-2 proteases, in order to activate transcription of target genes in the nucleus (Brown and Goldstein, 1997).

The proteolytic activation of SREBPs is tightly regulated by sterols through the interaction with SREBP cleavage-activating protein (SCAP), an ER-membrane-bound escort protein of SREBPs. When sterols accumulate in the ER membranes, the SCAP/SREBP complex fails to exit the ER to the Golgi, and thereby the proteolytic processing of SREBPs is suppressed. SREBPs are key lipogenic transcription factors that govern the homeostasis of fat metabolism.

The prior art is deficient in the novel compositions and methods useful for the treatment of a variety of metabolic disorders. The present invention fulfills this longstanding need and desire in the art.

SUMMARY OF THE INVENTION

The present invention is directed to a compound having the general structure:

A-B-C

The A ring is a pyridine or a substituted pyridine, a piperidine or a substituted piperidine, a pyrrolidine or a substituted pyrrolidine, a thiazole or a substituted thiazole, a phenyl ring or a substituted phenyl ring. The B ring is a thioazole or a substituted thioazole, a piperazine or a substituted piperazine, a phenyl ring or a substituted phenyl ring. The C ring is a phenyl ring or a substituted phenyl ring, a pyridine or a substituted pyridine, a thioazole or a substituted thioazole.

The present invention is directed to a compound having the chemical structure

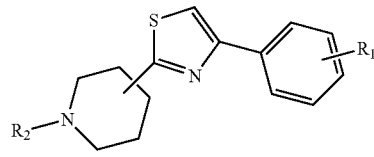

The $R_1$ substituents are H, halogen, —OH, —O—$C_{1-3}$ alkoxy, —OC(O)$R_3$; $R_3$ is $C_1$-$C_3$ alkyl or aryl, —OCH$_2$—C(O)O$R_4$; $R_4$ is H or $C_1$-$C_3$ alkyl, —NH$R_5$; $R_5$ is H, $C_1$-$C_4$ alkyl, alkylcyclopropane, benzyl, —NHC(O)$C_1$-$C_3$ amide, —NHC(O)O—$R_6$ carbamate; $R_6$ is tert-butyl or benzyl, —NH—SO$_2$—$R_7$ sulfonamide and $R_7$ is alkyl or aryl. The $R_2$ substituents may be alkyl or $R_8$OC(O)— and $R_8$ is $C_3$-$C_5$ alkyl or aryl.

The present invention directed further to a compound having the chemical structure

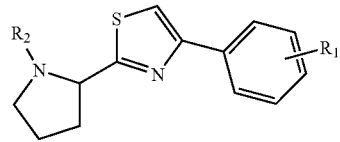

The $R_1$ substituents are H, halogen, —OH, —O—$C_{1-3}$ alkoxy, —OC(O)$R_3$; $R_3$ is $C_1$-$C_3$ alkyl or aryl, —OCH$_2$—C(O)O$R_4$; $R_4$ is H or $C_1$-$C_3$ alkyl, —NH$R_5$; $R_5$ is H, $C_1$-$C_4$ alkyl, alkylcyclopropane, benzyl, —NHC(O)$C_1$-$C_3$ amide, —NHC(O)O—$R_6$ carbamate; $R_6$ is tert-butyl or benzyl, —NH—SO$_2$—$R_7$ sulfonamide and $R_7$ is alkyl or aryl. The $R_2$ substituents may be alkyl or $R_8$OC(O)— and $R_8$ is $C_3$-$C_5$ alkyl or aryl.

The present invention directed further still to a compound having the chemical structure

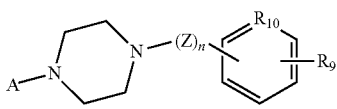

The $R_9$ is H, halogen, —OH, —O—$C_1$-$C_3$ alkoxy, —OC(O)$R_{11}$; $R_{11}$ is $C_1$-$C_3$ alkyl or aryl, —OCH$_2$—C(O)OR$_{12}$; $R_{12}$ is H or $C_1$-$C_3$ alkyl, —NHR$_{13}$; $R_{13}$ is H, $C_1$-$C_4$ alkyl, alkylcyclopropane, benzyl, —NHC(O)C$_{1-3}$amide, —NHC(O)O—R$_{14}$carbamate; $R_{14}$ is tert-butyl or benzyl, —NH—SO$_2$—R$_{15}$ sulfonamide; $R_{15}$ is alkyl or aryl or —SO$_2$—NH—R$_{16}$ sulfonamide and $R_{16}$ is alkyl or aryl. The $R_{10}$ is nitrogen or methylene. n is 0 or 1 and when n is 1, Z is —C=O. A may have the structure

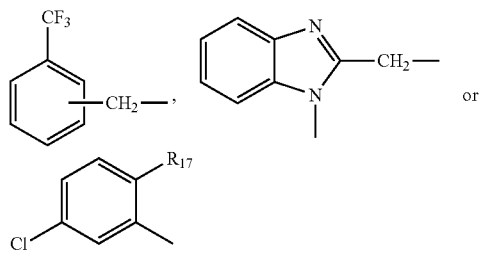

wherein $R_{17}$ is H or $C_1$-$C_3$ alkyl group.

In a preferred embodiment of the invention, there is a method for treating a metabolic disorder in an individual, comprising the step of administering to the individual a therapeutically effective amount of at least one compound having the chemical structure:

A-B-C or a pharmaceutically acceptable salt or a stereoisomer thereof or a combination thereof.

In one aspect the metabolic disorder comprises obesity, hyperlipemia, diabetes and complications of diabetes, fatty liver, hypertension, cancer or cardiovascular disease.

In a related embodiment, the individual is provided an additional therapy. The additional therapy comprises dietary therapy, physical therapy, behavior therapy, surgery, drug therapy, and a combination thereof. In some aspects, the metabolic disorder is diabetes and the additional therapy comprises dietary therapy, physical therapy, and drug therapy.

In another preferred embodiment a compound that is N-(4-(2-(2-propylpyridin-4-yl)thiazol-4-yl)phenyl)methanesulfonamide, tert-butyl-2-(4-(4-bromophenyl)thiazol-2-yl)pyrrolidine-1-carboxylate, benzyl 2-(4-(4-bromophenyl)thiazol-2-yl)pyrrolidine-1-carboxylate, 4-(4-bromophenyl)-2-(pyrrolidin-2-yl)thiazole, 4-(4-bromophenyl)-2-(1-propylpyrrolidin-2-yl)thiazole, tert-butyl 3-(4-(4-bromophenyl)thiazol-2-yl)piperidine-1-carboxylate, benzyl 3-(4-(4-bromophenyl)thiazol-2-yl)piperidine-1-carboxylate, 3-(4-(4-bromophenyl)thiazol-2-yl)-1-propylpiperidine, benzyl 4-(4-(4-bromophenyl)thiazol-2-yl)piperidine-1-carboxylate, benzyl (R)-2-(4-(4-(methylsulfonamido)phenyl)thiazol-2-yl)pyrrolidine-1-carboxylate, benzyl 3-(4-(4-(methylsulfonamido)phenyl)thiazol-2-yl)piperidine-1-carboxylate, benzyl 4-(4-(4-(methylsulfonamido)phenyl)thiazol-2-yl)piperidine-1-carboxylate, 4-(3-(pyridin-2-yl)-[1,2,4]triazolo[4,3-b]pyridazin-6-yl)-N-tosylbenzenamine, (4-(5-chloro-2-methylphenyl)piperazin-1-yl)(4-(tosylamino)phenyl)methanone, 4-(4-((1-methyl-1H-benzo[d]imidazole-2-yl)methyl)piperazin-1-yl)-N-tozylbenzenamine, 3-chloro-4-methyl-N-(6-(4-(3-(trifluoromethyl)benzyl)piperazin-1-yl)pyridin-3-yl)benzenesulfonamide, 4-chloro-N-(4-(4-((1-methyl-1H-benzo[d]imidazol-2-yl)methyl)piperazin-1-yl)phenyl)benzenesulfonamide, (Z)-4-(3-cyano-3-(4-(2,4-dimethyl phenyl)thiazol-2-yl)allyl)-N-(thiazol-2-yl) benzenesulfonamide, N-(3-(H-imidazo[1,2-a]pyridine-2-yl)phenyl)-4-methyl-2-phenylthiazole-5-carboxamide, N-(3-(benzo[d]thiazol-2-yl)phenyl)isonicotinamide, 3-(4-chlorophenyl)-4,5-dihydro-1-phenyl-5-(2-phenylthiazol-4-yl)-1H-pyrazole, N-(4-(6-methylbenzo[d]thiazol-2-yl)phenyl)-2-(N-m-tolylmethyl sulfonamido)acetamide, N-(4-(6-methylbenzo[d]thiazol-2-yl)phenyl)-2-(N-p-tolylmethyl sulfonamido)acetamide; a pharmaceutically acceptable salt; a stereoisomer thereof; and any combination thereof.

In certain embodiment of the invention, there is a method of inhibiting a member of a SREBP pathway in an individual, comprising the step of providing to the individual a therapeutically effective amount of at least one compound of the present invention. In one aspect, the member of a SREBP pathway is SREBP-1, SREBP-2, or both.

The present invention is also directed to a kit comprising the compound described herein and a container housing the compound.

The foregoing has outlined rather broadly the features and technical advantages of the present invention in order that the detailed description of the invention that follows may be better understood. Additional features and advantages of the invention will be described hereinafter, which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

(FIG. 1B) A summary of the RT-PCR and microarray data. ACL, ATP citrate lyase; HMG CoAR, 3-hydroxy-3-methyl-glutaryl-CoA reductase; LDLR, low-density lipoprotein receptor, MVD, mevalonate pyrophosphate decarboxylase; SCD, stearyl-CoA desaturase; INSIG1, insulin-induced gene 1; GAPDH, glyceraldehyde-3-phosphate dehydrogenase.

In FIG. 2C HEK293 cells were transfected with pCMV-SREBP-1c (1-436) and pSRE-Luc, and the transfected cells were treated with or without 20 mM fatostatin A in a medium containing lipid-free serum. Each value represents the average of three independent experiments.

FIGS. 3A-3H show effects of fatostatin A on SREBP-1 and -2. DU145 cells were treated with DMSO alone or fatostatin A (1 and 5 μM) for 6 hrs. The levels of precursor and mature forms of SREBP-1 (FIG. 3A) or SREBP-2 (FIG. 3B) were examined by western blots. Western blots of actin are shown in lower panel as a loading control. (FIGS. 3C-3H) Localization of SREBP-1 was examined by immunostaining. Cells were treated with DMSO alone (FIG. 3C-3E) or 5 μM of fatostatin A (FIGS. 3F-3H) and then stained with DAPI (FIG. 3C and FIG. 3F) or anti-SREBP-1 (FIG. 3D and FIG. 3G).

FIGS. 4A-4G show inhibition of the insulin-induced adipogenesis by siRNA knockdown of the SREBP-1. Two stably transfected clones of 3T3-L1 cells in which the expression of SREBP-1 were knocked down were established and induced to differentiate into adipocytes. The knockdown cells were not differentiated (FIG. 4D and FIG. 4F), whereas 3T3-L1 cells transfected with an empty vector (neo) were mostly differentiated into adipocytes (FIG. 4B). FIGS. 4A, 4C and 4E show the cells without the insulin induction. FIG. 4G is a Western blot analysis of the clones indicating the successful knockdown of SREBP-1.

In FIG. 5A two stably transfected clones of DU145 cells in which the expression of SREBP-1 were knocked down were established and grown in an MEM medium containing no serum, 2% fetal bovine serum (FBS), 2% fat-free fetal bovine serum, or 1 μg/mL of IGF1 for three days. The growth rates were measured by WST-1 assays. The knockdown cells failed to grow in the MEM medium containing no serum, 2% fat-free FBS, or 1 μg/mL of IGF1 but exhibited as much growth as control cells in the presence of serum. The experiments were performed in triplicate. FIG. 5B are Western blots showing the extents of SREBP-1 knockdown in clones 1 and 2.

FIG. 6C shows serum constituents of the treated and control mice. FIG. 6D is a representative western blot for SREBP-1 of the liver extracts from 2 different mice from the control and fatostatin A treated groups. The loaded amounts of proteins were normalized. FIG. 6E is a representative western blot showing FAS expression (top panel) and a coomassie stained gel for loading control (bottom) of liver extracts. FIGS. 6F-6G illustrate activities of FAS and ACC in liver extracts. Data are means+SD (n=5); *P<0.05.

FIG. 7A shows body weight before and after the treatment with fatostatin A and FIG. 7B shows the amounts of weight loss after treatment. FIG. 7C show the serum levels of glucose, cholesterol, and triglycerides (TG) in the treated and control mice. FIG. 7D shows FAS activity in liver extracts. FIG. 7E is a representative western blot analysis of the liver extracts of three mice each for control and treated groups. The loaded amounts of proteins were normalized. Data are means+SD (n=5); *P<0.05.

FIGS. 8A-8C show effect of fatostatin A on body weight and food consumption. Two groups of ob/ob male mice (n=5) were daily injected intraperitoneally with fatostatin A or 10% DMSO in PBS to control groups for four weeks. Mice were fed normal chow and on first day of the experiment and every day thereafter the weight of the mice and the amount of the food consumed were measured. FIG. 8A is a picture of representative control and fatostatin A treated mice. FIG. 8B shows the weight of each mouse within each group was measured daily. The average and variance of the weights are shown. In FIG. 8C food intake was measured every day and was expressed as cumulative food intake per mouse over the 28 days period.

FIGS. 9A-9H demonstrate serum constituents of control and fatostatin A treated ob/ob mice. Blood was collected from tail veins of overnight fasted mice, and serum was collected after separation from cells. Constituents were determined as described below. The data are shown as mean±SD, n=5 mice in each group.

FIGS. 10A-10D show effect of fatostatin on liver and adipose tissue of ob/ob mice. FIG. 10A shows livers of fatostatin A treated mice (left) and controls (right). FIG. 10B shows histological analyses of frozen sections of livers of the control and fatostatin A ob/ob mice stained with Oil Red-0 to detect lipid droplets and counter-stained with Mayer's hematoxylin. Livers of three different mice treated with fatostatin A, showing a dramatic decrease in red-stained droplets (top) and controls showing an abundance of red-stained lipid droplets compared to the treated mice (bottom). FIG. 10C shows epididymal fat pads isolated from fatostatin A treated ob/ob mice (left) and controls (right). FIG. 10D shows the average weight of livers and epididymal fat pads isolated from ob/ob controls and fatostatin A treated mice. The data are shown as mean±SD, n=5 mice in each group (*P<0.05).

FIG. 12A shows the activity of acetyl-CoA carboxylase (ACC) and FIG. 12B shows fatty acid synthase measured in liver extracts of ob/ob mice as described below. FIG. 12C is a Western Blot analysis of liver crude extracts, from three individual ob/ob mice, were separated by 4-12% NuPAGE MES gels and probed with different antibodies and detected with ECL. FIG. 12D shows the ratio of the intensity of the specific bands, of different lipogenic enzymes from fatostatin A against control mice after normalization to actin. The data are shown as mean±SD, n=5 mice in each group (†P=0.005; ‡P=0.002; *P<0.05)

FIGS. 14A-14F illustrates exemplary compounds 1-66 of the present invention.

FIG. 19A is a Western blot analysis showing effects of brefeldin A on CHO-K1 cells treated with EtOH alone, sterols (10 µg/ml cholesterol and 1 µg/ml 25-hydroxycholesterol), or 20 µM fatostatin. FIG. 19B is a Western blot analysis with anti-SCAP IgG-9D5 of cells grown in the absence or presence of 20 µM fatostatin or sterols (10 µg/mL cholesterol and 1 µg/mL 25-hydroxycholesterol). Numbers on the right denote the number of N-linked sugar chains present on protease-protected SCAP fragments.

FIGS. 20A-20D show the structures of dansyl fatostatin, fatostatin-polyproline linker-biotin conjugate and polyproline linker-biotin conjugate and cells treated with the same. FIG. 20A illustrates how the polyproline linker was inserted for better projection of the fatostatin molecule (Sato et al., 2007). In FIG. 20B CHO-K1 cells treated with dansyl fatostatin and ER-tracker red showing localization of dansyl fatostatin in the ER. Scale bar=10 µm. FIG. 20C illustrates the interaction of fatostatin with SCAP, shown by western blot analysis with anti-SCAP, anti-SREBP-1, anti-SREBP-2, and anti-ATF6 antibodies of proteins bound to Neutravidine-agarose beads saturated with biotinylated fatostatin in CHO-K1 membrane extract. FIG. 20D shows that for the competition assay, membrane extracts were preincubated with EtOH alone, cholesterol, or fatostatin.

FIGS. 25A-25D show that fatostatin reduces the expression levels and activities of lipogenic enzymes. Activity of acetyl-CoA carboxylase (ACC) (FIG. 25A) and fatty acid synthase (FAS) (FIG. 25B) were measured in liver extracts of ob/ob mice. Western Blot analysis of liver crude extracts was performed (FIG. 25C). Ratio of the intensity of the specific bands, of different lipogenic enzymes from fatostatin against control mice after normalization to actin are shown (FIG. 25D). The data are shown as mean±SD, n=5 mice in each group (†P=0.005; ‡P=0.002; *P<0.05)

DETAILED DESCRIPTION OF THE INVENTION

Figures 1A, 1B:
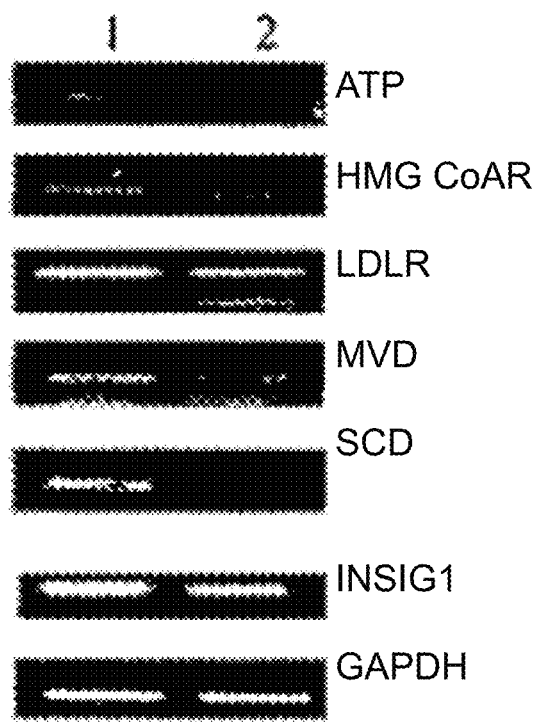
FIGS. 1A-1B show confirmation of the microarray results by RT-PCR. DU145 cells were treated with DMSO (lane 1) and 5 μM fatostatin A (lane 2) for 6 hrs (FIG. 1A). Total RNA was then extracted and subjected to RT-PCR.

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the invention may "consist essentially of" or "consist of" one or more sequences of the invention, for example. Some embodiments of the invention may consist of or consist essentially of one or more elements, method steps, and/or methods of the invention. It is contemplated that any method or composition described herein can be implemented with respect to any other method or composition described herein.

General Embodiments of the Invention

Metabolic disorders are treated and/or prevented with compounds of the present invention. For example, dysregulated biosynthesis of fatty acids and cholesterols and excessive intake of dietary fat are correlated with a number of medical complications including at least obesity, diabetes, hypertension, and cardiovascular diseases, and in certain aspects these conditions are treated and/or prevented with a compound of the invention. Epidemiological evidence indicates that metabolic diseases including obesity also promote the development of an aggressive form of cancers, including but not limited to prostate cancer.

Upon fat depletion, sterol regulatory element binding proteins (SREBPs) are proteolytically released from the membrane and translocated into the nucleus, where they activate the transcription of the genes involved in cholesterol and fatty acid biosynthesis. The present invention identifies a synthetic small molecule previously known to block both adipogenesis and cancer cell growth as a selective inhibitor of the SREBP activation and also provides analogs and derivatives of that molecule. The drug-like molecule fatostatin A impairs the proteolytic activation of SREBPs, thereby reducing the transcription of their responsive genes in cells. In mice, fatostatin A blocks the activation of SREBP-1 in the liver, reduces body weight, lowers the levels of blood cholesterol and glucose, and down-regulates lipogenic enzymes. Fatty acid synthase and acetyl-CoA carboxylase activities and their expression levels were decreased in the liver of the treated mice. Fatostatin A serves as a tool to understand cellular pathways and provides a consensus molecule as at least starting point for pharmacological intervention of metabolic diseases, in certain aspects.

Small molecules that modulate metabolism-related phenotypes serve as tools for dissecting the complex associations, in specific embodiments. Fatostatin A causes two distinct phenotypes in cultured mammalian cells: complete inhibition of the insulin-induced adipogenesis of 3T3-L1 mouse fibroblast cells; and selective repression of the serum-independent insulin-like growth factor 1 (IGF1)-dependent growth of DU145 human prostate cancer cells.

In certain aspects of the invention, fatostatin A selectively blocks the activation of SREBPs, a key lipogenic transcription factor that activates specific genes involved in cholesterol and fatty acid synthesis. The identification of fatostatin A as an inhibitor of SREBPs is consistent with its anti-adipogenic property, and indicates a role of SREBPs in the IGF1-dependent growth of prostate cancer.

The present invention concerns fatostatin A as a compound that blocks the activation of at least SREBP-1, for example as shown in experimental mice. Administration of fatostatin A into obese ob/ob mice led to weight loss and marked reduction of visceral fat.

Metabolic Disorders

The present invention concerns treatment and/or prevention of at least one symptom of a metabolic disorder. The metabolic disorder may be of any kind, so long as one of its symptoms is improved or prevented with a compound of the present invention. In particular, though, the metabolic disease is from one or more inborn errors of metabolism (which may be referred to as genetic disorders), such as inherited traits that are due to a defective metabolic enzyme (for example one having one or more mutations or disorders that involve mutations in regulatory proteins and in transport mechanisms).

Generally, metabolic disorders may be defined as disorders that affect energy production in a cell. Although most metabolic disorders are genetic, some may be acquired as a result of one or more factors, including diet, toxins, infections, and so forth. Genetic metabolic disorders may be caused by genetic defects that result in missing or improperly constructed enzymes necessary for some step in the metabolic process of the cell. The largest categories of metabolic disorders include the following: 1) glycogen storage diseases (also referred to as glycogenosis or dextrinosis), which include disorders that affect carbohydrate metabolism; 2) fatty oxidation disorders, which affect fat metabolism and metabolism of fat components; and 3) mitochondrial disorders, which affect mitochondria. Examples of glycogen storage diseases (GSD) include at least GSD type I (glucose-6-phosphatase deficiency; von Gierke's disease); GSD type II (acid maltase deficiency; Pompe's disease); GSD type III (glycogen debrancher deficiency; Cori's disease or Forbe's disease); GSD type IV (glycogen branching enzyme deficiency; Andersen disease); GSD type V (muscle glycogen phosphorylase deficiency; McArdle disease); GSD type VI (liver phosphorylase deficiency, Hers's disease); GSD type VII (muscle phosphofructokinase deficiency; Tarui's disease); GSD type IX (phosphorylase kinase deficiency); and GSD type XI (glucose transporter deficiency; Fanconi-Bickel disease).

Fatty acid metabolism deficiencies may be described as fatty oxidation disorders or as lipid storage disorders, in certain embodiments. They may involve one or more inborn errors of metabolism that result from enzyme deficiencies that affect the body's ability to oxidize fatty acids for the production of energy within muscles, liver, and other cell types, for example. Examples of fatty acid metabolism deficiencies include at least coenzyme A dehydrogenase deficiencies; other coenzyme A enzyme deficiencies; carnitine-related disorders; or lipid storage disorders. Examples of coenzyme A dehydrogenase deficiencies include at least very long-chain acyl-coenzyme A dehydrogenase deficiency (VL-CAD); long-chain 3-hydroxyacyl-coenzyme A dehydrogenase deficiency (LCHAD); medium-chain acyl-coenzyme A dehydrogenase deficiency (MCAD); short-chain acyl-coenzyme A dehydrogenase deficiency (SCAD); and short chain L-3-hydroxyacyl-coA dehydrogenase deficiency (SCHAD). Examples of other coenzyme A enzyme deficiencies include at least 2,4 Dienoyl-CoA reductase deficiency; 3-hydroxy-3-methylglutaryl-CoA lyase deficiency; and malonyl-CoA decarboxylase deficiency. Examples of carnitine-related deficiencies include at least primary carnitine deficiency; carnitine-acylcarnitine translocase deficiency; carnitine palmitoyltransferase I deficiency (CPT); and carnitine palmitoyltransferase II deficiency (CPT). Examples of lipid storage diseases include acid lipase diseases; Wolman disease; cholesteryl ester storage disease; Gaucher disease; Niemann-Pick disease; Fabry disease; Farber's disease; gangliosidoses; Krabbé disease; and metachromatic leukodystrophy. Other fatty acid metabolism disorders include at least mitochondrial trifunctional protein deficiency; electron transfer flavoprotein (ETF) dehydrogenase deficiency (GAII & MADD); Tangier disease; and acute fatty liver of pregnancy. Examples of mitochondrial diseases include at least progressive external ophthalmoplegia (PEO); Diabetes mellitus and deafness (DAD); Leber hereditary optic neuropathy (LHON) Mitochondrial encephalomyopathy, lactic acidosis, and stroke-like syndrome (MELAS); Myoclonic epilepsy and ragged-red fibers (MERRF); Leigh syndrome; subacute sclerosing encephalopathy; Neuropathy, ataxia, retinitis pigmentosa, and ptosis (NARP); Kearns-Sayre syndrome (KSS); Myoneurogenic gastrointestinal encephalopathy (MNGIE). In particular aspects of the invention, the metabolic disorder is, or has as one of its complications, one or more of the following: obesity, hyperlipemia, diabetes, fatty liver, hypertension, and cardiovascular disease.

Exemplary Compositions of the Invention

In a preferred embodiment, there is a method of treatment of metabolic disorders, the method of treatment comprising the administration of at least one compound, or pharmaceutically acceptable salts and stereoisomers thereof, having the general formula:

A-B-C where A, B, and C can be the same or different and each may be a 5-, 6-, or 7-membered ring or a fused bicyclic ring system, the ring being a heterocyclic ring or non-heterocyclic ring, a substituted ring or non-substituted ring, A, B and C are either directly connected or connected through an intervening atom chain or linker and said atom chain or linker is a saturated carbon chain or an unsaturated carbon chain with or without additional functional groups.

Preferably, the A ring is a 6-membered heterocyclic ring with one heteroatom. The A ring may be substituted. In preferred embodiments, the ring is a pyridine ring; more preferably, the nitrogen atom of the pyridine ring is in the 4-position or in the 2-position relative to the position of the B ring. Most preferably, the pyridine ring is substituted with a n-propyl group on a carbon positioned alpha to the nitrogen heteroatom. In other preferred embodiments, there is a 1-5 atom side chain, more preferably a 1-5 carbon side chain, on the A ring. In other illustrative and non-limiting embodiments, the A ring may be phenyl, pyrrole, thiophene, furan, pyrimidine, isoquinoline, quinoline, benzofuran, indole, oxazole, naphthyl, piperidine, pyrrolidine, imidazole, imidazol[1,2-a]pyridine, benzoimidazole, thiazole, or benzothiazole, for example.

In one aspect of the invention, the A ring is a piperidine ring. Preferably, the nitrogen atom of the piperidine ring is in the 4-position relative to the position of the B ring. In other related aspect, nitrogen atom of the piperidine ring is in the 3-position relative to the position of the B ring. The nitrogen atom of the piperidine may be further substituted and wherein the substitutions are selected from the group consisting of alkyl, sulfoxide, sulfone, alkyl or aryl sulfonate, sulfonic acid, and any combination thereof. For example, the substitution may be a propyl group, a tert-butyloxycarbonyl (BOC) or a benzyloxycarbonyl group.

In further aspect of the invention, the A ring is a pyrrolidine ring; preferably, the nitrogen atom of the pyrrolidine ring is in the 2-position relative to the position of the B ring. The nitrogen atom of the pyrrolidine may be further substituted and wherein the substitutions are selected from the group consisting of alkyl, sulfoxide, sulfone, alkyl or aryl sulfonate, sulfonic acid, and any combination thereof. For example, the substitution may be a propyl group, a tert-butyloxycarbonyl (BOC) or a benzyloxycarbonyl group.

Preferably, the B ring is a 5-membered ring with at least two heteroatoms. The B ring may be substituted. In preferred embodiments, the B ring is a thiazole ring. In other illustrative and non-limiting embodiments, the B ring may be oxazole, imidazol, isooxazole, imidazole, thiphene, furan, pyrimidine, pyrazole, isothiazole, thiazolopyridazine, aryl, or pyrazole, for example. The B ring may further be a 6-membered ring with two heteroatoms. For example, the B ring is a piperazine ring. Preferably, the C ring is a 6-membered ring, most preferably a phenyl ring. The C ring may be substituted. In preferred embodiments, the C ring is methyl substituted. In other illustrative and non-limiting embodiments, the C ring may be phenyl, pyridine, pyrrole, thiophene, furan, pyrimidine, isoquinoline, quinoline, benzofuran, indole, oxazole, or naphthyl, for example.

Exemplary compounds are provided in FIGS. 14A-14F. Referring to compound 1, the n-propyl substituted pyridine ring corresponds to the A ring of the general formula, the 2,4-substituted thiazole ring corresponds to the B ring of the general formula, and the methyl substituted phenyl ring corresponds to the C ring of the general formula. It should be understood that substitutions are permissible at any position in any of the A, B, and C rings and any substitutions may be the same or different from any other substitutions. Non-limiting examples of the substitutions, in addition to those shown in FIGS. 14A-14F, include the following groups: H (i.e., unsubstituted); hydroxy; $C_{1-10}$ alkyl; $C_{2-10}$ alkenyl; $C_{2-10}$ alkynyl; $C_{3-6}$ cycloalkyl; aryl; heteroaryl; wherein said alkyl, alkenyl, alkynyl, cycloalkyl, aryl and heteroaryl groups are optionally substituted with 1-5 groups selected from the group consisting of hydroxy, —(C=O)$R^a$; —(C=O)O$R^a$, —(C=O)H, —(C=O)OH, O(CH$_2$)$_n$COO$R^a$ wherein n=1-10 and wherein $R^a$ is a $C_{1-10}$ alkyl, $C_{2-10}$ alkenyl, $C_{2-10}$ alkynyl, or $C_{3-6}$ cycloalkyl, aryl, heteroaryl, fluoro, chloro, bromo, iodo, cyano, carboxy, amino, mono-substituted amino and di-substituted amino, mono-substituted amido and di-substituted amido and any combination thereof; —(C=O)$R^a$; —(C=O)O$R^a$, —(C=O)H; —(C=O)OH; —O(CH$_2$)$_n$COO$R^a$ wherein n=1-10 and wherein $R^a$ is a $C_{1-10}$ alkyl, $C_{2-10}$ alkenyl, $C_{2-10}$ alkynyl, or $C_{3-6}$ cycloalkyl, aryl or heteroaryl fluoro, chloro, bromo, iodo; cyano; carboxy; amino; amido; mono- and di-substituted amino having a substitution selected from the group consisting of $C_{1-10}$ alkyl, $C_{2-10}$ alkenyl, $C_{2-10}$ alkynyl, $C_{3-6}$ cycloalkyl, aryl, heteroaryl, sulfoxides, sulfones, sulfonates, alkyl sulfonates, sulfonic acids and any combination thereof; wherein said alkyl, alkenyl, alkynyl, cycloalkyl, aryl and heteroaryl are optionally substituted with 1-5 groups selected from the group consisting of hydroxy, —(C=O)$R^a$, —(C=O)O$R^a$, —(C=O)H, —(C=O)OH, —O(CH$_2$)$_n$COO$R^a$ wherein n=1-10 and wherein $R^a$ is a $C_{1-10}$ alkyl, $C_{2-10}$ alkenyl, $C_{2-10}$ alkynyl, or $C_{3-6}$ cycloalkyl, aryl and heteroaryl; fluoro; chloro; bromo; iodo; cyano; carboxy; amino; mono- and di-substituted amino with one or more of $C_{1-10}$ alkyl, $C_{2-10}$ alkenyl, $C_{2-10}$ alkynyl groups, and any combination thereof; and, mono- and di-substituted amido having a substitution selected from the group consisting of $C_{1-10}$ alkyl, $C_{2-10}$ alkenyl, $C_{2-10}$ alkynyl, $C_{3-6}$ cycloalkyl, aryl, heteroaryl, sulfoxides, sulfones, sulfonates, alkyl sulfonates, sulfonic acids, sulfonates, alkyl sulfonates, sulfonic acids and any combination thereof; wherein said alkyl, alkenyl, alkynyl, cycloalkyl, aryl and heteroaryl are optionally substituted with 1-5 groups selected from the group consisting of hydroxyl; —(C=O)$R^a$; —(C=O)O$R^a$, —(C=O)H; —(C=O)OH, —O(CH$_2$)$_n$COO$R^a$ wherein n=1-10 and wherein $R^a$ is a $C_{1-10}$ alkyl, $C_{2-10}$ alkenyl, $C_{2-10}$ alkynyl, or $C_{3-6}$ cycloalkyl, aryl or heteroaryl; fluoro; chloro; bromo; iodo; cyano; carboxy; amino; mono- and di-substituted amino with one or more of $C_{1-10}$ alkyl, $C_{2-10}$ alkenyl, $C_{2-10}$ alkynyl groups, and any combination thereof.

In the present invention, there is one compound, or pharmaceutically acceptable salt or stereoisomer thereof, having the general formula: A-B-C, wherein A, B, and C are the same or different and wherein each comprises a 5-, 6-, or 7-membered ring or a fused bicyclic ring system, the ring being a heterocyclic ring or non-heterocyclic ring, a substituted ring, or non-substituted ring, wherein A, B and C are either directly connected or connected through an intervening atom chain or linker and wherein said atom chain or linker is a saturated carbon chain or an unsaturated carbon chain with or without additional functional groups, wherein any one, any two, or all three of A, B, and C are unsubstituted or have one or more substitutions, and wherein any substitution may be the same or different from any other substitution, and wherein the substitutions are consisting of: a) hydroxy, b) C1-10 alkyl, c) C2-10 alkenyl, d) C2-10 alkynyl, e) C3-6 cycloalkyl, f) aryl, g) heteroaryl wherein said substitutions in b), c), d), e), f), and/or g) are optionally further substituted with 1-5 groups consisting of: 1) hydroxy, 2) —(C=O)$R^a$, 3) —(C=O)O$R^a$, 4) —(C=O)H, 5) —(C=O)OH, 6) —O(CH$_2$)$_n$COO$R^a$ wherein n=1-10, 7) halo, 8) cyano, 9) carboxy, 10) amino, 11) mono-substituted amino, 12) di-substituted amino, 13) amido, 14) mono-substituted amido; 15) di-substituted amido, and any combination thereof, wherein in 2), 3), or 6) $R^a$ is a C1-10 alkyl, C2-10 alkenyl, C2-10 alkynyl, C3-6 cycloalkyl, aryl, or heteroaryl, h) —(C=O)$R^a$, i) —(C=O)O$R^a$, j) —(C=O)H, k) —(C=O)OH; l) —O(CH$_2$)$_n$COO$R^a$ wherein n=1-10, wherein in h), i), or l), $R^a$ is a $C_{1-10}$ alkyl, $C_{2-10}$ alkenyl, $C_{2-10}$ alkynyl, $C_{3-6}$ cycloalkyl, aryl or heteroaryl, m) halo, n) cyano, o) carboxy, p) amino, q) mono-substituted amino, r) di-substituted amino, s) amido, t) mono-substituted amido, and u) di-substituted amido wherein one or more of said mono-substituted amino, di-substituted amino, mono-substituted amido, and di-substituted amido have a substitution selected from the group consisting of C1-10 alkyl, C2-10 alkenyl, C2-10 alkynyl, C3-6 cycloalkyl, aryl, heteroaryl, sulfoxide, sulfone, sulfonate, alkyl sulfonate, sulfonic acid, and any combination thereof, wherein in u) said alkyl, alkenyl, alkynyl, cycloalkyl, aryl or heteroaryl are optionally further substituted with 1-5 groups selected from the group consisting of: i) hydroxy, ii) —(C=O)$R^a$, iii) —(C=O)O$R^a$, iv) —(C=O)H, v) —(C=O)OH, vi) —O(CH$_2$)$_n$COO$R^a$ wherein n=1-10, wherein in ii), iii), or vi)

R$^a$ is a C$_{1-10}$ alkyl, C$_{2-10}$ alkenyl, C$_{2-10}$ alkynyl, C$_{3-6}$ cycloalkyl, aryl or heteroaryl, vii) halo, viii) cyano, ix) carboxy, x) amino, xi) mono-substituted amino, xii) di-substituted amino, xiii) amido; xiv) mono-substituted amido, xv) di-substituted amido, and any combination thereof.

Preferably, A is a pyridine or a substituted pyridine, a piperidine or a substituted piperidine, a pyrrolidine or a substituted pyrrolidine, a thiazole or a substituted thiazole, a phenyl ring or a substituted phenyl ring; B is a thioazole or a substituted thioazole, a piperazine or a substituted piperazine, a phenyl ring or a substituted phenyl ring; and C is a phenyl ring or a substituted phenyl ring, a pyridine or a substituted pyridine, a thioazole or a substituted thioazole.

The present invention is directed to a compound having the general structure

The R$_1$ substituents are H, halogen, —OH, —O—C$_{1-3}$ alkoxy, —OC(O)R$_3$; R$_3$ is C$_1$-C$_3$ alkyl or aryl, —OCH$_2$—C(O)OR$_4$; R$_4$ is H or C$_1$-C$_3$ alkyl, —NHR$_5$; R$_5$ is H, C$_1$-C$_4$ alkyl, alkylcyclopropane, benzyl, —NHC(O)C$_{1-3}$ amide, —NHC(O)O—R$_6$ carbamate; R$_6$ is tert-butyl or benzyl, —NH—SO$_2$—R$_7$ sulfonamide and R$_7$ is alkyl or aryl. The R$_2$ substituents may be alkyl or R$_8$OC(O)— and R$_8$ is C$_3$-C$_5$ alkyl or aryl.

The present invention is directed further to a compound having the general structure

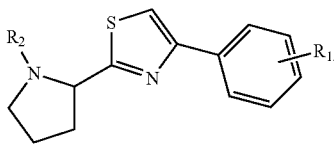

The R$_1$ substituents are H, halogen, —OH, —O—C$_{1-3}$ alkoxy, —OC(O)R$_3$; R$_3$ is C$_1$-C$_3$ alkyl or aryl, —OCH$_2$—C(O)OR$_4$; R$_4$ is H or C$_1$-C$_3$ alkyl, —NHR$_5$; R$_5$ is H, C$_1$-C$_4$ alkyl, alkylcyclopropane, benzyl, —NHC(O)C$_{1-3}$ amide, —NHC(O)O—R$_6$ carbamate; R$_6$ is tert-butyl or benzyl, —NH—SO$_2$—R$_7$ sulfonamide and R$_7$ is alkyl or aryl. The R$_2$ substituents may be alkyl or R$_8$OC(O)— and R$_8$ is C$_3$-C$_5$ alkyl or aryl.

The present invention is directed further still to a compound having the general structure

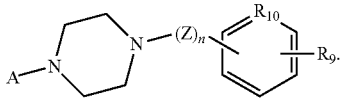

The R$_9$ is H, halogen, —OH, —O—C$_1$-C$_3$ alkoxy, —OC(O)R$_{11}$; R$_{11}$ is C$_1$-C$_3$ alkyl or aryl, —OCH$_2$—C(O)OR$_{12}$; R$_{12}$ is H or C$_1$-C$_3$ alkyl, —NHR$_{13}$; R$_{13}$ is H, C$_1$-C$_4$ alkyl, alkylcyclopropane, benzyl, —NHC(O)C$_{1-3}$amide, —NHC(O)O—R$_{14}$carbamate; R$_{14}$ is tert-butyl or fluorenylmethyl, —NH—SO$_2$—R$_{15}$ sulfonamide; R$_{15}$ is alkyl or aryl or —SO$_2$—NH—R$_{18}$ sulfonamide; R$_{16}$ is alkyl or aryl. The R$_{10}$ is nitrogen or methylene. n is 0 or 1 and when n is 1, Z is —C═O. A may have the structure

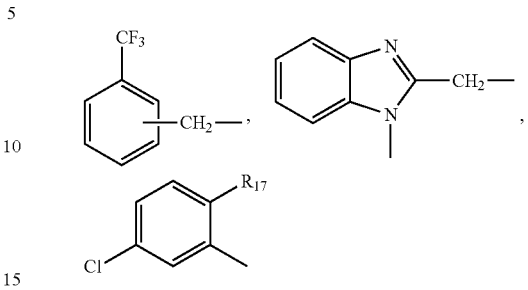

wherein R$_{17}$ is H or C$_1$-C$_3$ alkyl group.

Examples of specific compounds include 2-propyl-4-(4-p-tolylthiazol-2-yl)pyridine; 4-(4-(4-bromophenyl)thiazol-2-yl)-2-propylpyridine; 4-(4-phenylthiazol-2-yl)-2-propylpyridine; 4-(4-(4-chlorophenyl)thiazol-2-yl)-2-propylpyridine; 4-(4-(4-ethylphenyl)thiazol-2-yl)pyridine; 4-(4-p-tolylthiazol-2-yl)pyridine; 4-(4-(4-methoxyphenyl)thiazol-2-yl)pyridine; 4-(2-(2-propylpyridin-4-yl)thiazol-4-yl)phenyl benzoate; 4-(2-(2-propylpyridin-4-yl)thiazol-4-yl)phenol; methyl 2-(4-(2-(2-propylpyridin-4-yl)thiazol-4-yl)phenoxy)acetate; 2-(4-(2-(2-propylpyridin-4-yl)thiazol-4-yl)phenoxy)acetic acid; 4-(4-chlorophenyl)-2-(3,4-dimethoxyphenyl)thiazole; 4-(4-(3,4-dichlorophenyl)thiazol-2-yl)-2-propylpyridine; 4-(4-(4-fluorophenyl)thiazol-2-yl)-2-propylpyridine; 4-(4-(2,4-difluorophenyl)thiazol-2-yl)-2-propylpyridine; 4-(2-(2-propylpyridin-4-yl)thiazol-4-yl)benzenamine; N-isopropyl-4-(2-(2-propylpyridin-4-yl)thiazol-4-yl)benzenamine; N-(4-(2-(2-propylpyridin-4-yl)thiazol-4-yl)phenyl)acetamide; N-benzyl-4-(2-(2-propylpyridin-4-yl)thiazol-4-yl)benzenamine; N-(cyclopropylmethyl)-4-(2-(2-propylpyridin-4-yl)thiazol-4-yl)benzenamine; 4-(4-bromophenyl)-2-(2-propylpyridin-4-yl)thiazole-5-carboxylic acid; methyl 4-(4-bromophenyl)-2-(2-propylpyridin-4-yl)thiazole-5-carboxylate; 4-(4-(4-methoxyphenyl)thiazol-2-yl)-2-propylpyridine; 4-(4-(3-methoxyphenyl)thiazol-2-yl)-2-propylpyridine; 4-(4-(2-methoxyphenyl)thiazol-2-yl)-2-propylpyridine; 2-phenyl-4-p-tolylthiazole; 3-(2-(2-propylpyridin-4-yl)thiazol-4-yl)phenol; 2-(2-(2-propylpyridin-4-yl)thiazol-4-yl)phenol; 4-(4-bromophenyl)-N-isopropyl-2-(2-propylpyridin-4-yl) thiazole-5-carboxamide; 4-(4-(4-chlorophenyl)thiazol-2-yl)pyridine; 4-(4-(4-chlorophenyl)thiazol-2-yl)-2-ethylpyridine; 4-(4-chlorophenyl)-2-phenylthiazole; 2-propyl-4-(4-(thiophen-2-yl)thiazol-2-yl)pyridine; 4-(4'-methyl[1,1-biphenyl]-4-yl)-2-propyl)pyridine; 2-(2-propylpyridin-4-yl)-4-p-tolylthiazole-5-carboxylic acid; 2-ethyl-4-(4-p-tolylthiazol-2-yl)pyridine; 4-phenyl-2-(2-propylpyridin-4-yl)thiazole-5-carboxylic acid; methyl 2-(2-propylpyridin-4-yl)-4-p-tolylthiazole-5-carboxylate; tert-butyl 4-(2-(2-propylpyridin-4-yl)thiazol-4-yl)phenylcarbamate; N-cyclohexyl-4-(2-(2-propylpyridin-4-yl)thiazol-4-yl)benzenamine; 4-(2-(2-propylpyridin-4-yl)thiazol-4-yl)-N-tosylbenzenamine; N-(4-(2-(2-propylpyridin-4-yl)thiazol-4-yl)phenyl)-8-quinolinesulfonamide; N-(4-(2-(2-propylpyridin-4-yl)thiazol-4-yl)phenyl)-2-thiophenesulfonamide, 2-propyl-4-(4-p-tolylthiazol-2-yl)pyridine; 4-(4-(4-bromophenyl)thiazol-2-yl)-2-propylpyridine, N-isopropyl-4-(2-(2-propylpyridin-4-yl)thiazol-4-yl)benzenamine, and N-(4-(2-(2-propylpyridin-4-yl)thiazol-4-yl)phenyl) methanesulfonamide.

Preferred compounds are N-(4-(2-(2-propylpyridin-4-yl)thiazol-4-yl)phenyl)methanesulfonamide, tert-butyl 2-(4-(4-bromophenyl)thiazol-2-yl)pyrrolidine-1-carboxylate, benzyl 2-(4-(4-bromophenyl)thiazol-2-yl)pyrrolidine-1-carboxylate, 4-(4-bromophenyl)-2-(pyrrolidin-2-yl)thiazole, 4-(4-bromophenyl)-2-(1-propylpyrrolidin-2-yl)thiazole, tert-butyl 3-(4-(4-bromophenyl)thiazol-2-yl)piperidine-1-carboxylate, benzyl 3-(4-(4-bromophenyl)thiazol-2-yl)piperidine-1-carboxylate, 3-(4-(4-bromophenyl)thiazol-2-yl)-1-propylpiperidine, benzyl 4-(4-(4-bromophenyl)thiazol-2-yl)piperidine-1-carboxylate, benzyl (R)-2-(4-(4-(methylsulfonamido)phenyl)thiazol-2-yl)pyrrolidine-1-carboxylate, benzyl 3-(4-(4-(methylsulfonamido)phenyl)thiazol-2-yl)piperidine-1-carboxylate, benzyl 4-(4-(4-(methylsulfonamido)phenyl)thiazol-2-yl)piperidine-1-carboxylate, 4-(3-(pyridin-2-yl)-[1,2,4]triazolo[4,3-b]pyridazin-6-yl)-N-tosylbenzenamine, (4-(5-chloro-2-methylphenyl)piperazin-1-yl)(4-(tosylamino)phenyl)methanone, 4-(4-((1-methyl-1H-benzo[d]imidazole-2-yl)methyl)piperazin-1-yl)-N-tozylbenzenamine, 3-chloro-4-methyl-N-(6-(4-(3-(trifluoromethyl)benzyl)piperazin-1-yl)pyridin-3-yl)benzenesulfonamide, 4-chloro-N-(4-(4-((1-methyl-1H-benzo[d]imidazol-2-yl)methyl)piperazin-1-yl)phenyl)benzenesulfonamide, (Z)-4-(3-cyano-3-(4-(2,4-dimethylphenyl)thiazol-2-yl)allyl)-N-(thiazol-2-yl)benzenesulfonamide, N-(3-(H-imidazo[1,2-a]pyridine-2-yl)phenyl)-4-methyl-2-phenylthiazole-5carboxamide, N-(3-(benzo[d]thiazol-2-yl)phenyl)isonicotinamide, 3-(4-chlorophenyl)-4,5-dihydro-1-phenyl-5-(2-phenylthiazol-4-yl)-1H-pyrazole, N-(4-(6-methylbenzo[d]thiazol-2-yl)phenyl)-2-(N-m-tolylmethylsulfonamido)acetamide, N-(4-(6-methylbenzo[d]thiazol-2-yl)phenyl)-2-(N-p-tolylmethylsulfonamido)acetamide; a pharmaceutically acceptable salt; a stereoisomer thereof; and any combination thereof.

The term "alkyl" as used herein refers to a substituting univalent group derived by conceptual removal of one hydrogen atom from a straight or branched-chain acyclic saturated hydrocarbon (i.e., —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, etc.).

The term "alkenyl" as used herein refers to a substituting univalent group derived by conceptual removal of one hydrogen atom from a straight or branched-chain acyclic unsaturated hydrocarbon containing at least one carbon-carbon double bond (i.e., —CH═CH$_2$, —CH═CHCH$_3$, —C═C(CH$_3$)$_2$, —CH$_2$CH═CH$_2$, etc.).

The term "alkynyl" as used herein refers to a substituting univalent group derived by conceptual removal of one hydrogen atom from a straight or branched-chain acyclic unsaturated hydrocarbon containing at least one carbon-carbon triple bond (i.e., —C≡CH, —C≡CCH$_3$, —C≡CCH(CH$_3$)$_2$, —CH$_2$C≡CH, etc.).

The term "aryloxy" as used herein refers to an aryl group with a bridging oxygen atom, such as phenoxy (—OC$_6$H$_5$), or benzoxy (—OCH$_2$C$_6$H$_5$). "Arylamino means an aryl group with a bridging amine function such as —NHCH$_2$C$_6$H$_5$. "Arylamido" means an aryl group with a bridging amide group such as —(C═O)NHCH$_2$C$_6$H$_5$.

The term "alkylidene" as used herein refers to a substituting bivalent group derived from a straight or branched-chain acyclic saturated hydrocarbon by conceptual removal of two hydrogen atoms from the same carbon atom (i.e., ═CH$_2$, ═CHCH$_3$, ═C(CH$_3$)$_2$, etc.).

The term "cycloalkyl" as used herein refers to a substituting univalent group derived by conceptual removal of one hydrogen atom from a saturated monocyclic hydrocarbon (i.e., cyclopropyl, cyclobutyl, cyclopentyl, cyclohexyl, or cycloheptyl).

The term "aryl" as used herein refers to a substituting univalent group derived by conceptual removal of one hydrogen atom from a monocyclic or bicyclic aromatic hydrocarbon. Examples of aryl groups are phenyl, indenyl, and naphthyl.

The term "heteroaryl" as used herein refers to a substituting univalent group derived by the conceptual removal of one hydrogen atom from a monocyclic or bicyclic aromatic ring system containing 1, 2, 3, or 4 heteroatoms selected from N, O, or S. Examples of heteroaryl groups include, but are not limited to, pyrrolyl, furyl, thienyl, imidazolyl, pyrazolyl, oxazolyl, isoxazolyl, thiazolyl, pyridyl, pyrimidinyl, pyrazinyl, benzimidazolyl, indolyl, and purinyl. Heteroaryl substituents can be attached at a carbon atom or through the heteroatom. Examples of monocyclic heteroaryl groups include pyrrolyl, furyl, thienyl, pyrazolyl, oxazolyl, isoxazolyl, thiazolyl, and pyridyl. Examples of bicyclic heteroaryl groups include pyrimidinyl, pyrazinyl, benzimidazolyl, indolyl, and purinyl. Individual rings may have 5 or 6 atoms. Thus, this includes a 4-membered monocyclic heteroaryl group and a 5-membered monocyclic heteroaryl group. It also includes a bicyclic heteroaryl group having one 5-membered ring and one 6-membered ring, and a bicyclic heteroaryl group having two 6-membered rings.

The term "halo" includes iodo, bromo, chloro and fluoro.

The term "substituted" shall be deemed to include multiple degrees of substitution by a substitutent. A substitution occurs where a valence on a chemical group or moiety is satisfied by an atom or functional group other than hydrogen. In cases of multiple substitutions, the substituted compound can be independently substituted by one or more of the disclosed or claimed substituent moieties, singly or plurally. By independently substituted, it is meant that the (two or more) substituents can be the same or different.

The term "pharmaceutically acceptable salt" refers herein to a salt of a compound that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-napthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The term "stereoisomer" means an isomeric molecule whose atomic connectivity is the same as one or more other molecules but whose atomic arrangement in space is different. This definition includes enantiomers, diastereomers, cis-isomers, trans-isomers, conformational isomers.

The term "unsubstituted" means all that valences on a chemical group or moiety are satisfied by hydrogen.

The term "saturated carbon chain" as used herein refers to a straight or branched-chain acyclic saturated hydrocarbon (i.e., —$CH_3$, —$CH_2$—, —$CH_2CH_3$, —$CH_2CH_2$— —$CH_2CH_2CH_3$, —$CH_2CH_2CH_2$, —$CH_2CH_2CH_2CH_3$, —$CH_2CH_2CH_2CH_3$—, —$CH_2CH(CH_3)_2$, —$C(CH_3)_3$, etc.).

The term "unsaturated carbon chain" as used herein refers to a straight or branched-chain acyclic unsaturated hydrocarbon containing at least one carbon-carbon double bond (i.e., —$CH=CH_2$, —$CH=CH$—, —$CH=CHCH_3$, —$C=C(CH_3)_2$, —$CH_2CH=CH_2$, —$CH_2CH=CH$— etc.) or at least one carbon-carbon triple bond (i.e., —$C\equiv CH$, —$C\equiv C$—, —$C\equiv CCH_3$, —$C\equiv CCH$—, —$C\equiv CCH(CH_3)_2$, —$CH_2C\equiv CH$, etc.).

The present invention also includes protected derivatives of compounds disclosed herein. For example, when compounds of the present invention contain groups such as hydroxyl or carbonyl, these groups can be protected with a suitable protecting group. A list of suitable protective groups can be found in T. W. Greene, Protective Groups in Organic Synthesis, John Wiley & Sons, Inc. 1981, the disclosure of which is incorporated herein by reference in its entirety. The protected derivatives of compounds of the present invention can be prepared by methods well known in the art.

The compounds of the present invention may have asymmetric centers, chiral axes, and chiral planes, and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure may be depicted.

SREBPs

In a specific embodiment of the invention, a composition of the invention targets one or more members of a sterol regulatory element binding protein (SREBP) pathway. The pathway relates to the proteolytic release of a membrane-bound transcription factor, SREBP, in specific aspects, which facilitates transport from the cytoplasm to the nucleus. There, SREBP binds elements referred to as the sterol regulatory elements (SREs) present in regulatory regions of the genes that encode enzymes associated with production of lipids. Upon binding of the SREBP to DNA, transcription of the target gene is modulated, such as upregulated.

Pharmaceutical Preparations

Pharmaceutical compositions of the present invention comprise an effective amount of one or more compositions of the invention (and additional agent, where appropriate) dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one fatostatin A analog or derivative or additional active ingredient will be known to those of skill in the art in light of the present disclosure, as exemplified by Remington's Pharmaceutical Sciences, 18th Ed. Mack Printing Company, 1990. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the pharmaceutical compositions is contemplated.

The fatostatin A analog or derivative may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation, e.g., aerosol inhalation, injection, infusion, continuous infusion, localized perfusion bathing target cells directly, via a catheter, via a lavage, in cremes, in lipid compositions, e.g., liposomes, or by other method or any combination of the forgoing as would be known to one of ordinary skill in the art (see, for example, Remington's Pharmaceutical Sciences, 18th Ed. Mack Printing Company, 1990).

The fatostatin A analog or derivative may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens, e.g., methylparabens, and propylparabens, chlorobutanol, phenol, sorbic acid, thimerosal or combinations thereof. In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include fatostatin A analog or derivative, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the fatostatin A analog or derivative may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Alimentary Compositions and Formulations

In preferred embodiments of the present invention, the fatostatin A analog or derivative is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579; and 5,792,451). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Parenteral Compositions and Formulations

In further embodiments, the fatostatin A analog or derivative may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,537,514, 6,613,308, 5,466,468, 5,543,158; 5,641,515; and 5,399,363.

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

Miscellaneous Pharmaceutical Compositions and Formulations

In other preferred embodiments of the invention, the active compound fatostatin A analog or derivative may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and laurocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212. Likewise, the delivery of drugs using intranasal microparticle resins (Takenaga et al., 1998) and lysophosphatidyl-glycerol compounds (U.S. Pat. No. 5,725,871) are also well-known in the pharmaceutical arts. Likewise, transmucosal drug delivery in the form of a polytetrafluoroethylene support matrix is described in U.S. Pat. No. 5,780,045.

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Combination Therapy

In order to increase the effectiveness of a composition of the invention, an additional therapy may be delivered to an individual having a metabolic disorder. For example, an individual that is obese may be administered a composition of the invention in addition to another therapy for obesity. Additional obesity therapies include dietary therapy, physical therapy (exercise), drug therapy, surgery, and behavioral therapy, for example. Exemplary drug therapies include, for example, Xenical Orlistat®, Phentermine, and Sibutramine (Meridia®). Exemplary surgeries include liposuction and gastric bypass, for example.

For individuals with diabetes, for example, exemplary additional compounds for therapy include one or more of the following: Actos (pioglitizone); ACTOSPlus Met; Amaryl (glimepiride); Avandaryl (Avandia+Glimiperide); Avandia (rosiglitazone); Avandamet (rosiglitazone maleate and metformin hydrochloride); Byettap; Duetact (pioglitazone HCl and glimepiride); Galvus (Vildagliptin); Glipizide (Sulfonlyurea); Glucophage (metformin); Glimepiride; Glucovance (glyburide/metformin); Glucotrol XL (glipizide extended release); Glyburide; Glyset (miglitol) glucosidase inhibitor; Januvia (sitagliptin phosphate); Metaglip (glipizide+metformin); Metformin-biguanide; Prandin (repaglinide); Precose (acarbose); Rezulin (troglitazone); Starlix (nateglinide). Other therapies for diabetes include an improvement in diet and exercise.

Exemplary Measurement of Metabolic Disorder Treatments

In particular aspects of the invention, an individual is given one or more compositions of the present invention and the individual is assessed for an improvement in at least one symptom of the metabolic disorder. For example, in particular embodiments when the metabolic disorder is obesity, an improvement in obesity may be determined during and/or following treatment with one or more compositions of the invention. An improvement in obesity may be measured by any standard means, but in particular aspects the improvement in obesity is measured by weight measurement, body mass index (BMI) measurement, and/or body part size measurement (such as waist measurement), for example. Exemplary methods for calculating BMI includes dividing a person's body weight in kilograms by their height in meters squared (weight [kg] height $[m]^2$). A BMI of 30 or more is considered obese and a BMI between 25 to 29.9 is considered overweight. In other aspects of the invention, an individual with diabetes is tested for an improvement following administration to the individual of the therapy of the invention. In one specific embodiment, the monitoring of diabetes occurs by blood test. For example, the blood test may measure the chemical A1C. The higher the blood sugar, the higher the A1C level will be. In some cases, cholesterol (including HDL and/or LDL cholesterol) and/or triglycerides are measured, such as by standard means in the art. In specific cases, a fasting lipoprotein profile is performed, such as by standard means in the art.

Kits of the Invention

Any of the compositions described herein may be comprised in a kit. In a non-limiting example, the kit comprises a composition suitable for treatment and/or prevention of one or more metabolic disorders. In other embodiments of the invention, the kit comprises one or more apparatuses to obtain a sample from an individual. Such an apparatus may be one or more of a swab, such as a cotton swab, toothpick, scalpel, spatula, syringe, and so forth, for example. In another embodiment, an additional compound is provided in the kit, such as an additional compound for treatment and/or prevention of a metabolic disorder. Any compositions that are provided in the kits may be packaged either in aqueous media or in lyophilized form, for example. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Fatostatin A Reduces the Expression of SREBP-Responsive Genes

Gene expression profile comparison of the drug-treated and untreated cells might reveal specific molecular pathways affected by fatostatin A. DU145 cells were treated with fatostatin A or DMSO alone, and extracted mRNA samples were analyzed by Affimetrix DNA microarrays mapping 33,000 genes (Table 1).

TABLE 1

Genes known or likely to be controlled by SREBPs were regulated by Fatostatin A showed in Microarray result

| Gene Code | Decreased fold | Name of genes |
| --- | --- | --- |
| Genes known to be controlled by SREBP | | |
| NM_000527.2 | 0.574349 | low density lipoprotein receptor (LDLR) |
| NM000859.1 | 0.5 | 3-hydroxy-3-methylglutaryl-Coenzyme A reductase (HMG CoA R) |
| NM 0002130.1 | 0.353553 | 3-hydroxy-3-methylglutaryl-Coenzyme A synthase 1 (HMG CoA S) |
| NM_001096.1 | 0.574349 | ATP citrate lyase |
| NM_000664.1 | 0.574349 | acetyl-Coenzyme A carboxylase alpha |
| NM_005063.1 | 0.574349 | stearoyl-CoA desaturase (SCD) |
| NM_002004.1 | 0.659754 | farnesyl pyrophosphate syntlietase |
| AK000162 | 0.535887 | acetyl-CoA synthetase |
| NM_000431.1 | 0.5 | me valonate kinase (MVK) |
| NM002461.1 | 0.329877 | mevalonate decarboxylase (MVD) |
| NM 003129.2 | 0.5 | squalene epoxidase |
| Genes relevant to sterol/fat synthesis | | |
| NM_022977.1 | 0.707107 | fatty-acid-Coenzyme A ligase long chain 4 |
| NM_004457.2 | 0.707107 | fatty-acid-Coenzyme A ligase long chain 3 |
| NM005931.1 | 0.659754 | fatty acid desaturase 1 |
| NM0019312 | 0.659754 | dihydrolipoamide S-acetyltransferase |
| AF167438 | 0.659754 | Homo sapiens androgen-regulated short-chain dehydrogenaseneductase 1 |
| NM006579.1 | 0.615572 | emopamil-bindingprotein (sterol isomerase) |
| D63807.1 | 0.615572 | lanosterol synthase |
| BC000408.1 | 0.574349 | acetyl-Coenzyme A acetyltransferase 2 |
| NM_004462.1 | 0.535887 | farnesyl-diphosphate farnesyltransferase 1 |
| D85181.1 | 0.5 | sterol-C5-desaturase |
| NM_01637I.I | 0.466517 | hydroxysteroid (17-beta) dehydrogenase 7 |
| NM 005542.1 | 0.329877 | Insulin induced gene 1 (INSIG1) |

The results showed that 55% of the genes downregulated (<0.7 fold) by fatostatin A are those known or likely to be controlled by sterol regulatory element binding protein (SREBP), including LDL receptor, HMG-CoA reductase, and fatty acid synthase (Horton et al., 2003). The downregulation of the representative SREBP-responsive genes were confirmed by RT-PCR experiments (FIGS. 1A-1B). These results indicated that fatostatin A is a selective inhibitor of the SREBP pathway.

Figures 2A, 2B, 2C:
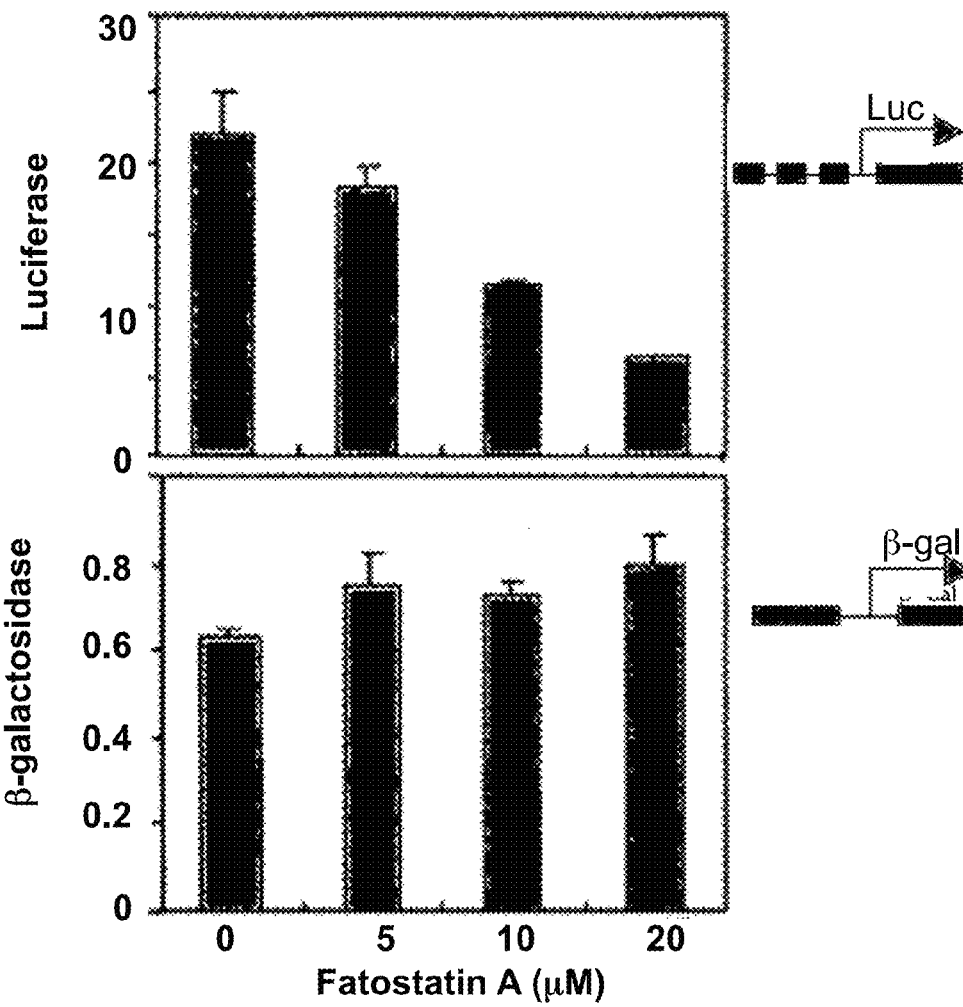
FIGS. 2A-2C show that fatostatin A suppresses the ability of endogenous SREBPs to activate a reporter gene. HEK293 cells were co-transfected with an SRE-1-driven luciferase reporter (pSRE-Luc) (FIG. 2A) and a β-gal reporter controlled under an actin promoter (FIG. 2B). The transfected cells were treated by varied concentrations of fatostatin A or DMSO alone in a medium containing lipid-free serum. After 20-hr incubation, luciferase activity was measured, and the data were normalized by β-galactosidase activity.

To show that fatostatin A impairs the function of SREBPs, the ability of endogenous SREBPs to activate transcription of an SREBP-responsive reporter gene was measured in the presence or absence of fatostatin A in HEK293 cells (FIGS. 2A-2B). Fatostatin A decreased in a concentration dependent manner the activation of the reporter gene in which the expression of luciferase is controlled by three repeats of sterol regulatory elements. In contrast, fatostatin A failed to impair the ability of an exogenously expressed mature form of SREBP-1 (amino acids 1-500) to activate the reporter gene activity (FIG. 2C). These results indicate that fatostatin A selectively blocks the activation process of SREBPs in cells.

Example 2

Fatostatin A Blocks the Proteolytic Activation of SREBPS

To examine whether fatostatin A affects the proteolytic activation of SREBPs, whole cell lysates of DU145 cells treated with fatostatin A were analyzed by western blots with an antibody against the NH2 terminus of SREBP-1 (FIG. 3A). The treatment of fatostatin A decreased the amounts of the 68 KDa mature form of SREBP-1 in a dose-dependent manner, while the amounts of the 125 KDa precursor form increased. Similar results were obtained for SREBP-2 with an antibody against its COOH terminus (FIG. 3B). These results indicate that fatostatin A directly or indirectly impairs the proteolytic activation of both SREBP isoforms.

The inhibition of the proteolytic activation of SREBPs would impair the nuclear translocation of SREBPs. Effects of fatostatin A on the subcellular localization of SREBP-1 were analyzed by immunofluorescence microscopy with an antibody against the NH2 terminus of SREBP-1. When cells were treated with DMSO alone, SREBP-1 was localized almost exclusively in the nucleus in a serum-free (fat free) medium (FIGS. 3C-3E). In contrast, when the cells were incubated with fatostatin A, the immunofluorescence of SREBP-1 decreased in the nucleus and reciprocally increased outside of the nucleus (FIGS. 3F-3H), indicating that fatostatin A inhibits the nuclear localization of SREBP-1.

Example 3

Validation of the Fatostatin Phenotypes by Knocking Down SREBP-1

Fatostatin A causes two phenotypes in cultured cells: (i) inhibition of the insulin-induced adipogenesis of 3T3-L1 cells and (ii) repression of the serum-independent growth of DU145 prostate cancer cells. The first phenotype is in complete agreement with the conclusion that fatostatin A is a blocker of SREBP-1 because of the known role of SREBP-1 in lipogenesis (Tontonoz et al., 1993). To confirm that under the cell-culture condition, the expression of SREBP-1 in 3T3-L1 cells was silenced by transfecting an expression vector of a small interfering RNA (siRNA) specific for SREBP-1 (FIG. 4G), and the effects of the silencing on the insulin-induced adipogenesis were examined. As expected, the knockdown of the SREBP-1 expression completely blocked the oil droplet formation of 3T3-L1 cells (FIGS. 4D-4F, clones 1 and 2), whereas the control cells transfected with an empty vector (neo; FIG. 4A) showed as much fat accumulation as the parental 3T3-L1 cells (FIG. 4B). These results indicate that the fatostatin A-induced phenotype in 3T3-L1 cells is mediated by the inhibition of SREBP-1.

Figure 5A:
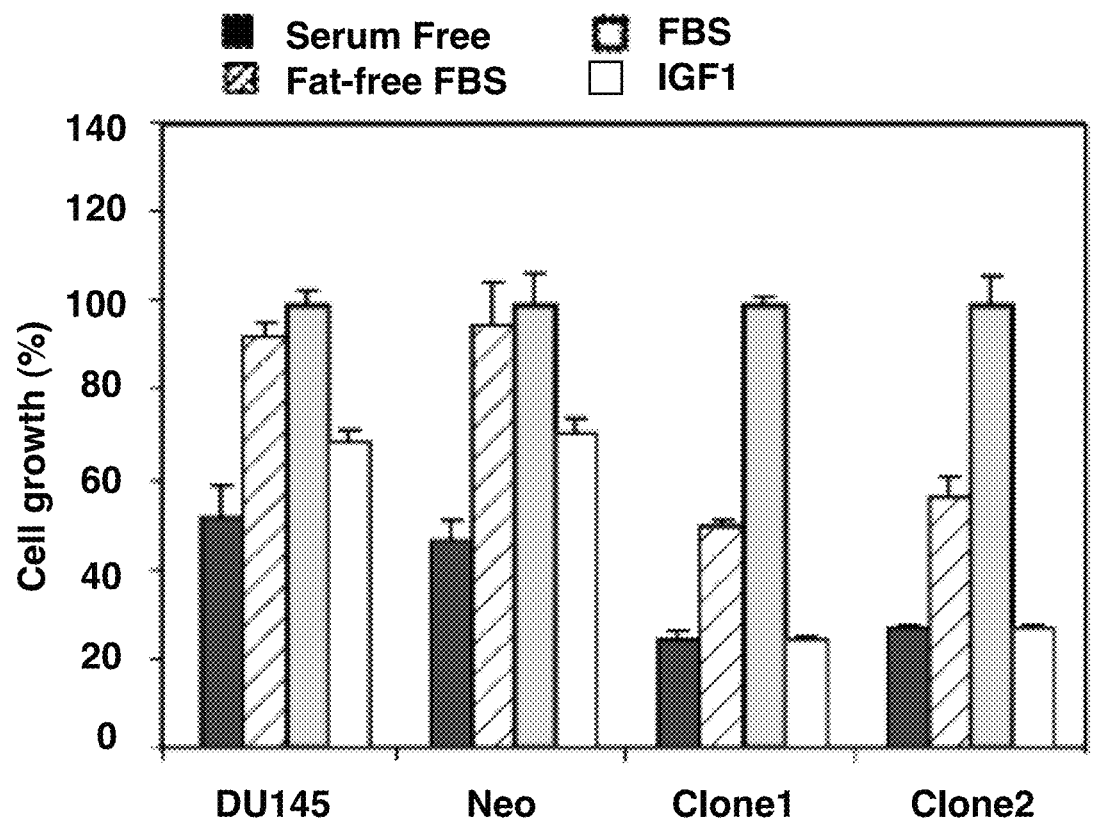
FIGS. 5A-5B demonstrate siRNA knockdown of SREBP-1 blocks the serum-independent growth of DU145 prostate cancer cell.
Figure 5B:
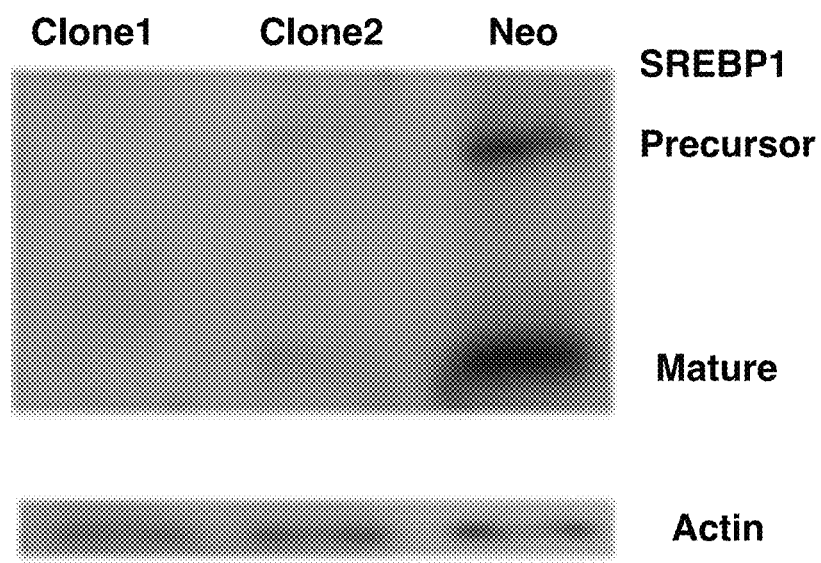

To test whether the inhibition of SREBP-1 by fatostatin A mediates the repression of serum-independent growth of DU145 cells, the expression of SREBP-1 in DU145 cells was silenced similarly by transfecting an expression vector of the SREBP-1-specific siRNA (FIG. 5B). The control cells transfected with the empty vector (neo) grew in the presence of either serum or IGF1, just as the parental DU145 cells did. In contrast, the knockdown cells in which the expression of SREBP-1 is silenced (clones 1 and 2) displayed reduced serum-independent IGF1-driven growth whereas their serum-dependent growth had little effects (FIG. 5A).

The requirement of SREBP-1 in the serum-independent growth may be due to the lack of external fat sources in the serum-free medium. Without exogenous fatty acids present in the serum, cells need to synthesize fatty acids and cholesterol, the building blocks of membranes, to maintain the cell growth. To test the importance of fatty acids in the cell growth, the growth of the SREBP-1 knockdown cells was monitored in a fat-free serum medium (FIG. 5A). The SREBP-1 silencing impaired the cell growth in a fat-free medium as much as it did in the serum-free IGF1-containing medium. These results indicate that fatostatin A blocks the serum-independent growth of cancer cells through the inhibition of SREBP-1.

Example 4

Figure 6A:
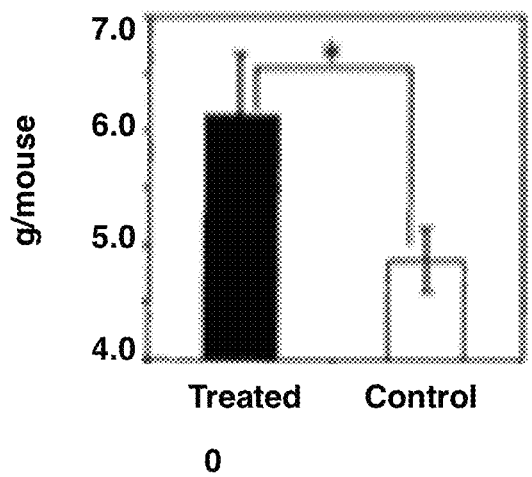
FIGS. 6A-6G demonstrate effects of fatostatin A on mice after fasting/refeeding fat free diet. Mice were injected with 30 mg/kg of fatostatin A intraperitoneally daily for the entire experiments starting one day before fasting for 48 hrs followed by feeding fat free diet for another 48 hrs. Loss of body weight (FIG. 6A) and food intake (FIG. 6B) were determined at the end of the 48-hr feeding.
Figure 6B:
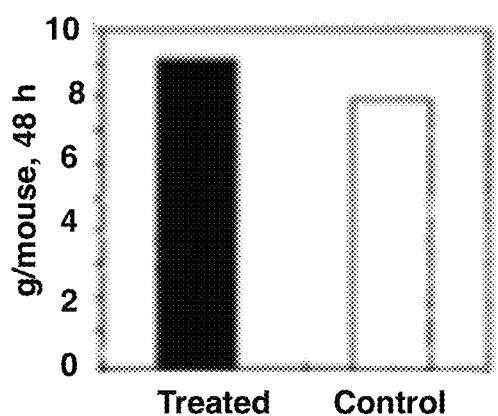
Figure 6C:
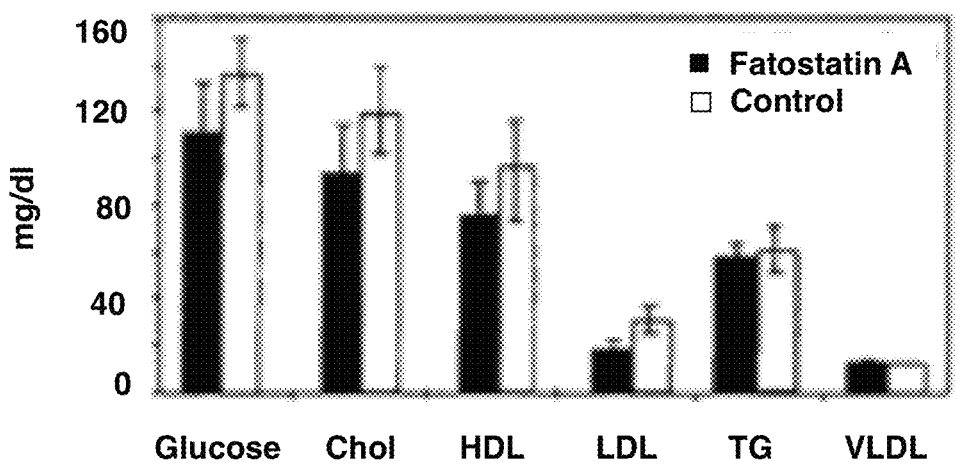

Fatostatin A Reduces Body Weight, Lowers Cholesterol and Glucose Levels, and Downregulates Lipogenic Enzymes in Mice The drug-like chemical structure of fatostatin A prompted the inventors to investigate its ability to inhibit SREBP-1 in the liver of whole animals. The effect of fatostatin A on hepatic SREBP-1 under lipogenic conditions of prolonged fasting (48 hours) followed by feeding fat free high carbohydrate diet for another 48 hours was examined. Mice were intraperitoneally injected with fatostatin A at 30 mg/kg/day for 5 days starting one day prior to the 48-hour fasting period. After 48 hours of fasting, the treated group lost more weight than the control group did ($6.12 \pm 0.6$ compared to $4.9 \pm 0.3$ gram/mouse; p=0.01.) (FIG. 6A). No reduction of food intake or obvious toxicity were observed during the treatment (FIG. 6B). Interestingly, after 48 hours of refeeding with fat free high carbohydrate diet, there was a trend of lowering glucose levels ($110 \pm 23$ compared to $137 \pm 14$ mg/dl; P=0.06 and cholesterol ($93 \pm 20$ compared to $120 \pm 19$ mg/dl; P=0.12) in the serum of fatostatin A-treated mice (FIG. 6C). Both HDL and LDL decreased in the treated mice group. However, the decrease in LDL levels appeared to be more significant ($16 \pm 5$ compared to $30 \pm 6$ mg/dl) (FIG. 6C).

Figure 6D:
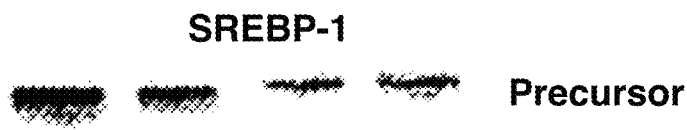
Figure 6E:
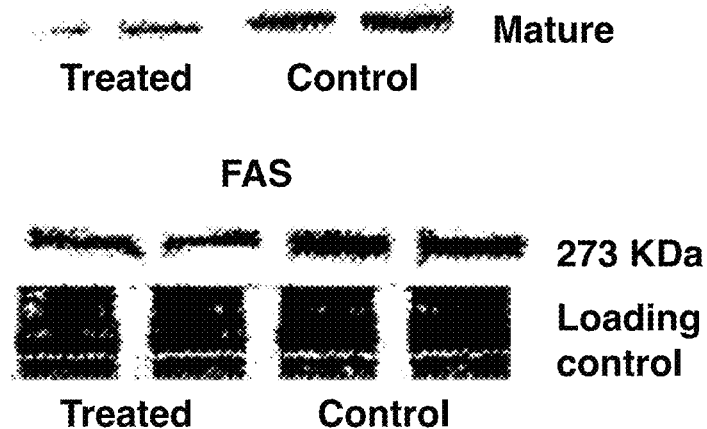
Figure 6F:
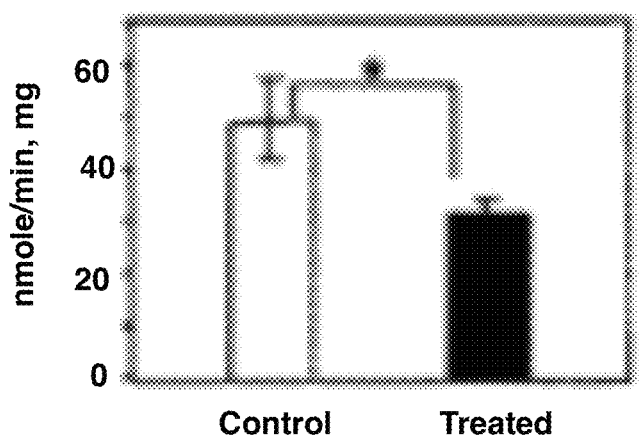
Figure 6G:
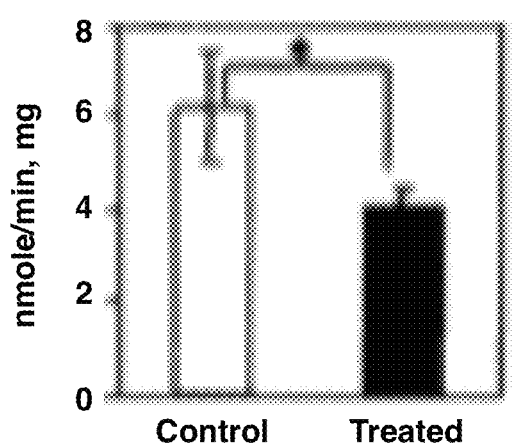

The expression levels of SREBP-1 in the liver extracts were examined by western blots. Consistent with the cell culture results, the liver extracts from the mice treated with fatostatin A displayed decreased amounts of the 68 KDa mature form of SREBP-1 and increased amounts of the 125 KDa precursor form (FIG. 6D). The hepatic expression of fatty acid synthase (FAS), a representative of SREBP-1-responsive lipogenic enzymes (Boizard et al., 1998), was also determined after the treatment. Western blot analysis of liver extracts showed that expression levels of FAS was decreased up to 30% by the fatostatin A treatment (FIG. 6E). Consistent with the reduction of the expression, its enzymatic activity in the extracts was similarly decreased. The activity of acetyl-CoA carboxylase (ACC) (FIG. 6F), which is also regulated by SREBP-1, decreased in liver extracts as observed for FAS (FIG. 6G). These results indicate that fatostatin A blocks the activation of SREBP-1 in mouse liver just as found in the cultured cells.

Figure 7A:
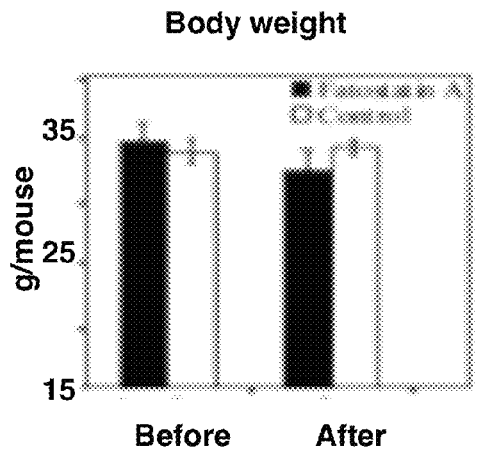
FIGS. 7A-7E show effects of two-week treatment of fatostatin A on mice. 5-6 month old mice were injected daily for two weeks either with 30 mg/kg fatostatin A or 10% DMSO.
Figure 7B:
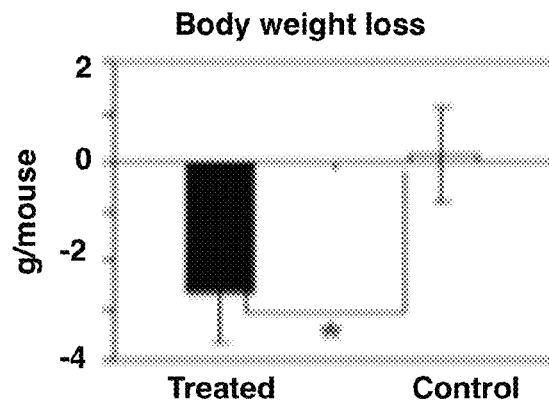
Figure 7C:
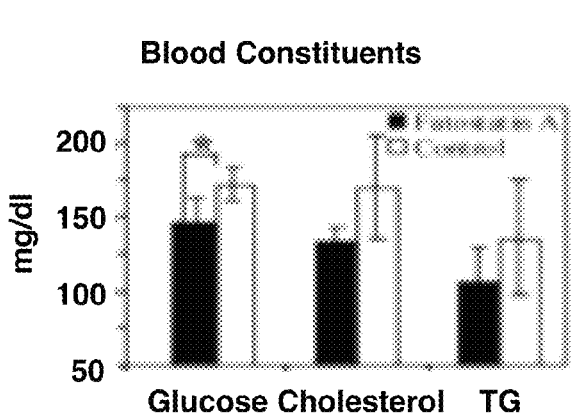
Figure 7D:
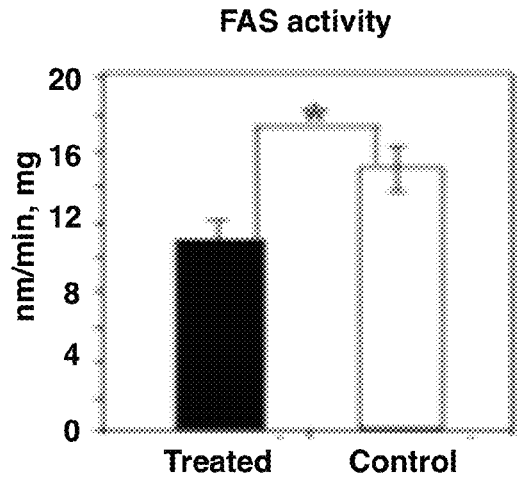
Figure 7E:
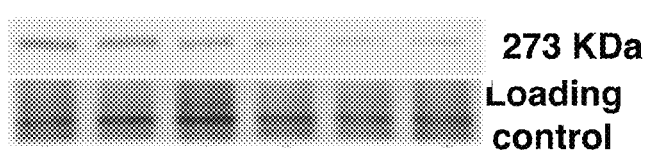

Longer treatment (two weeks) of another group of mice fed with normal diet resulted in 10% loss of body weight whereas the control group had no change of body weight (FIGS. 7A-7B). Food intake was similar between both groups (3.8 and 3.5 g/mouse/day for treated and control mice, respectively). Consistent with the results of mice fed under fasting/refeeding fat free diet, mice fed with normal diet exhibited significantly lower glucose levels and a trend of lower triglyceride (TG) and cholesterol levels in the blood (FIG. 7C). FAS activity and its protein level were also decreased about 30% (FIGS. 7D and 7E).

Example 5

Significance of the Present Invention

Bioactive small molecules have proven to be valuable tools for exploring complex cellular processes including metabolic pathways. A key regulator of lipid homeostasis and insulin action is a family of SREBP transcription factors (Brown and Goldstein, 1997). Small molecules that modulate the SREBP functions may find their use in the treatment of metabolic diseases and may serve as tools for further molecular understanding of the diseases. Our cell-based and animal data suggest that fatostatin A impairs the expression of lipogenic genes through downregulating the amounts of the mature SREBP-1 form in the nucleus. To the knowledge of the inventors, fatostatin A represents the first non-sterol-like synthetic molecule that inhibits the proteolytic activation of SREBPs both in cultured cells and mouse liver.

Small molecules that activate SREBP-1 and -2 were been reported (Grand-Perret et al., 2001). These LDL-lowering molecules upregulate the expression of LDL receptor by stimulating the proteolytic activation of SREBPs. Although the molecular mechanism of the action has not been elucidated, data suggested that SCAP is a primary target of the molecules. Unlike these molecules, fatostain A inhibits the activation of SREBPs and downregulates the expression of SREBP-responsive genes including the gene of LDL receptor (Table 1).

The animal data of fatostatin A are consistent with the cell culture results. In liver extracts of mice treated with fatostatin A under refeeding fat free diet, there was a significantly lower level of mature SREBP-1 form and a higher level of the precursor form. On the other hand and as expected, the level of the mature form was higher than the precursor form in liver extracts of the control group (Horton et al., 1998). Interestingly, it seems that the there was no change in the overall amount of the combined forms, and the only difference is at the distribution between the nuclear (mature) and the cytosolic forms (precursor). These data indicate that fatostatin A may not alter the expression level of SREBP-1, rather enhances the cleavage process of the precursor resulting in a decrease in its amount and an increase in the mature and active form. The importance of the SREBP-1 cleavage in fat synthesis has been shown by the experiments using mice deficient in SCAP: the livers of the mice failed to induce the expression of ACC and FAS under refeeding conditions (Liang et al., 2002).

In order to assess the physiological significance of the reduced level of the nuclear SREBP-1, the levels and activities of ACC and FAS were determined. Their activities in liver extracts were downregulated in response to fatostatin A treatment. These results are consistent with the role of SREBP-1 as a regulator of the fatty acid synthesis pathway (Shimano, 2000). Shimano et al. showed that the levels of FAS and ACC were not induced when SREBP-1$^{-/-}$ mice were fed with high carbohydrate diet (Shimano et al., 1997), confirming the role of SREBP-1 in regulating the expression of the lipogenic enzymes.

An interesting observation in the fatostatin A treated mice compared to control is a reduction of body weight and blood glucose. One possibility for the reduction in body weight is due to a lower lipogenesis rate, as a result of the downregulation of lipogenic enzymes such as ACC and FAS. In addition, the reduction in malonyl-CoA, the product of ACC and a potent inhibitor of carnitine palmitoyl transferase, may result in enhanced fatty acid oxidation and fat burning. In a specific embodiment of the invention, inhibition of SREBP-1 cleavage by fatostatin A downregulates lipogenic enzymes, enhances fatty acid oxidation, reduces weight, and increases insulin sensitivity resulting in lowering glucose.

Example 6

Materials

Lipid-depleted serum was prepared as described (Goldstein et al., 1983). Fat-free FBS was obtained from Fisher.

Rabbit anti-SREBP-1 (sc-8984) and goat anti-actin (sc-1616) polyclonal antibody were purchased from Santa Cruz Biotechnology. Mouse anti-SREBP-2 polyclonal antibody and mouse anti-FAS antibody were obtained from BD Biosciences. Anti-goat IgG HRP and anti-rabbit IgG HRP were obtained from Promega. ProLong Gold antifade reagent with DAPI was obtained from Molecular Probes Invitrogen Detection Technologies. Anti-rabbit IgG FITC was obtained from Chemicon International. Dexamethasone (DEX) and 1-methyl-3-isobutylxanthin (MIX) were obtained from Sigma.

Preparation of Fatostatin A

A mixture of 2-bromo-4'-methylacetophenone (1.22 g, 5.70 mmol) and prothionamide (1.03 g, 5.70 mmol) in ethanol (20 ml) was heated at 70° C. with stirring for 0.5 hour, and then cooled to 0° C. A yellow precipitate formed was filtered, washed with cold ethanol, and dried to give fatostatin A HBr salt (1.78 g, 83%) as yellow needles: $^1$H NMR (DMSO-$d_6$, 600 MHz) $d_H$ 8.88 (d, J=6.2 Hz, 1H), 8.54 (s, 1H), 8.46 (d, J=1.4 Hz, 1H), 8.36 (dd, J=1.4, 6.2 Hz, 1H), 7.99 (d, J=7.6 Hz, 2H), 7.31 (d, J=7.6 Hz, 2H), 3.03 (t, J=7.6 Hz, 2H), 2.35 (s, 3H), 1.80 (m, 2H), 0.96 (t, J=7.6, 3H); HRMS (FAB) exact mass calcd for $C_{18}H_{18}N_2S+H$ requires m/z 295.1269. found m/z 295.1269.

Cell Culture

DU145 human androgen-independent prostate cancer cells (ATCC) were maintained in an Eagle's minimum essential medium containing 2 mM L-glutamine, 1.0 mM sodium pyruvate, 0.1 mM nonessential amino acids, and 1.5 g/L sodium bicarbonate with 10% fetal bovine serum, 100 units/mL penicillin, and 100 µg/mL streptomycin sulfate at 37° C. under 5% $CO_2$. 3T3-L1 fibroblasts cells (ATCC) were maintained in a Dulbecco's modified Eagle's medium containing 5.5 mM glucose, 10% fetal bovine serum, 50 µg/mL gentamycin, 0.5 mM glutamine, and 0.5 µg/mL fungizone at 37° C. Human embryonic kidney 293 cells (ATCC) were maintained in a Dulbecco's modified Eagle's medium with 10% fetal bovine serum, 100 units/mL penicillin, and 100 µg/mL streptomycin sulfate at 37° C. under 5% $CO_2$.

Oligonucleotide Microarray Analysis

DU145 prostate cancer cells were treated with 5 mM of fatostatin A or DMSO alone in the presence of 1 µg/mL of IGF1 for 6 hrs in a serum free medium, total RNA was extracted in a TRI reagent (Molecular Research Center) and further isolated by RNeasy Mini Kit (Qiagen). Purified mRNA was analyzed in Baylor College of Medicine Microarray Core Facility by Affymetrix Human Genome U133 Plus 2.0 Array consisting of almost 45,000 probe sets representing more than 39,000 transcripts derived from approximately 33,000 well-substantiated human genes (Affymetrix, Inc.).

Luciferase Reporter Assay

On day 0, HEK293 cells were plated out in triplicate at a density of $5 \times 10^3$/well onto a 96-well plate in a Dulbecco's modified Eagle's medium with 10% fetal bovine serum, 100 units/mL penicillin, and 100 µg/mL streptomycin sulfate. On day 2, the cells were transiently co-transfected with the following plasmids by using Lipofectamine reagent (Invitrogen): 0.4 µg/well pSRE-Luc (an SRE-1-driven luciferase reporter construct; Hua et al., 1995 J Biol Chem 270, 29422-7), and 0.1 µg/well a b-gal reporter in which the expression of β-gal is controlled by an actin promoter in a final volume of 150 mL. After incubation for 5 hrs at 37° C., the cells were washed with phosphate-buffered saline and then incubated in 100 µl of Dulbecco's modified Eagle's medium with 10% lipid-depleted serum, 100 units/4 penicillin, and 100 µg/mL streptomycin sulfate in the absence or presence of fatostatin A. After 20 hrs of incubation, the cells in each well were lysed with 20 µL of 1× Reporter Lysis Buffer (Promega), and aliquots were used for measurement of luciferase (10 µL) and β-galactosidase (10 µL) activities. For luciferase assay, photon production was detected as counts per second in a Wallac 1420 ARVOsx multilabel counter (PerkinElmer). For β-galactosidase assays, hydrolysis of O-nitrophenyl-β-D-galactosidase was measured after incubation for 0.5 h at 37° C. by a microplate reader at the wave length of 405 nm (Tecan). The luciferase activity (counts per second) was normalized by the activity of β-galactosidase (OD units). For overexpression of the N-terminal matured form of SREBP-1c, pCMV-SREBP-1c (1-436) was co-transfected with pSRE-Luc. pSRE-Luc and pCMV-SREBP-1c (1-436) were provided by J. L. Goldstein (University of Texas Southwestern Medical Center).

RT-PCR Experiments

Total RNA was extracted from DU145 cells in TRI reagent (Molecular Research Center) and isolated with an RNeasy Mini Kit (Qiagen). The RNA sample was subjected to RT-PCR by using the Access RT-PCR System (Promega). RT-PCR reactions contained total RNA, 1 µM of each primer, 0.2 mM dNTP, 1 mM $MgSO_4$, AMV reverse transcriptase (2 units), and Tfl DNA polymerase (2 units) in a final volume of 25 µL. The primer pairs used are as follows: 5'-TCA GAC CGG GAC TGC TTG GAC GGC TCA GTC-3' (SEQ ID NO: 1) and 5'-CCA CTT AGG CAG TGG AAC TCG AAG GCC G-3' (SEQ ID NO: 2) for Low density lipoprotein receptor (LDLR); 5'-GCC TGC TTG ATA ATA TAT AAA C-3' (SEQ ID NO: 3) and 5'-CAC TTG AAT TGA GCT TTA G-3' (SEQ ID NO: 4) for stearoyl-CoA desaturase (SCD); 5'-AAG AAA AAG TGT CAG ACA GCT GG-3' (SEQ ID NO: 5) and 5'-TGG ACT GAA GGG GTG TTA GC-3' (SEQ ID NO: 6) for ATP citrate lyase (ACL); 5'-GCC CGA CAG TTC TGA ACT GGA ACA-3' (SEQ ID NO: 7) and 5'-GAA CCT GAG ACC TCT CTG AAA GAG-3' (SEQ ID NO: 8) for 3-hydroxy-3-methylglutaryl-CoA reductase (HMG CoA R); 5'-CTG CCT GAC TGC CTC AGC-3' (SEQ ID NO: 9) and 5'-ACC TCT CCT GAC ACC TGG G-3' (SEQ ID NO: 10) for mevalonate kinase (MVD); 5'-AAG ACT TCA GGG TAA GTC ATC A-3' (SEQ ID NO: 11) and 5'-CGT GTA TAA TGG TGT CTA TCA G-3' (SEQ ID NO: 12) for insulin induced gene 1 (INSIG1). The amplification conditions are as follows: 1 cycle at 94° C. for 4 min, then denatured at 94° C. for 40 s, annealed at 50° C. for 40 s, and extended at 68° C. for 2 min with 22 cycles for SCD and HMG CoA R, annealed at 58° C. with 24 cycles for LDLR and INSIG1, or annealed at 60° C. with 24 cycles for ATP citrate lyase (ACL), annealed at 55° C. with 30 cycles for MVD. The amplified DNAs were analyzed by an agarose gel and quantified with the Scion-image (version 4.02) software.

Western Blotting

DU145 prostate cancer cells were seeded on a 6-well plate at a density of $2 \times 10^5$ cells/well in a serum-free MEM incubated at 37° C. for overnight. The cells were then treated with DMSO or fatostatin A (1 or 5 mM) in presence of IGF1 (1 µg/mL). After 6 hrs of incubation, the cells were harvested in PBS and lysated in an SDS buffer. The samples were separated on a 10% SDS-PAGE gel and blotted by using rabbit anti-SREBP-1 and anti-SREBP-2 antibodies. The specific bands were visualized by using enhanced chemiluminescent (ECL) detection reagents (Amersham).

Immunofluorescence Experiments

DU145 prostate cancer cells were seeded on coverslips for overnight in a serum-free MEM, and then treated with 5 mM of fatostatin A or DMSO alone in a serum-free MEM containing IGF1 (1 µg/mL). After 6 hrs of incubation, the cells were fixed for 20 min in methanol at −20° C. and blocked for 1 hr in a PBS containing 5% milk and 0.1% Tween 20. The samples were incubated with rabbit polyclonal anti- SREBP-1 (Santa Cruz: sc-8984) and then fluorescein isothiocyanate-conjugated anti-rabbit IgG antibody (Chemicon Inc). The coverslips were visualized under a Nikon TE200 fluorescence microscope at ×400 magnification with appropriate filters for fluorescence detection.

siRNA Knockdown of SREBPs

Complimentary oligonucleotides derived from the sequence of the SREBP-1 gene (512-531), 5'-GAT CCC CGC CAC ATT GAG CTC CTC TCT TCA AGA GAG AGA GGA GCT CAA TGT GGC TTT TTG GAAA-3' (SEQ ID NO: 13), and 5'-AGC TTT TCC AAA AAG CCA CAT TGA GCT CCT CTC TCT CTT GAA GGA GGA GCT CAA TGT GGC GGG-3' (SEQ ID NO: 14), were inserted into a pSUPER vector (OligoEngine). The resulting plasmid was transfected into 3T3-L1 or DU145 cells with Fugene 6 (Roche). To establish stably transfected clones, neomycin-derivative G418 (Gibco) was used at a concentration of 500 μg/mL, and stable transformants were established. The expression levels of the SREBP-1 were evaluated by western blots. For adipogenesis experiments, 3T3-L1 cells were seeded onto a 96-well plate in a DMEM with 10% fetal bovine serum and incubated for another two days to complete confluence. On day 0, the medium was switched to the induction medium: DMEM containing 10% fetal bovine serum, 5 μg/mL of insulin, 0.5 mM 1-methyl-3-isobutylxanthin (MIX), and 1 μM dexamethazone (DEX). On day 2, the induction medium was removed and switched to a DMEM medium containing 10% fetal bovine serum and 5 μg/mL of insulin. On day 10, adipose oil droplets were stained with Oil-Red O. For cell growth experiments, DU145 cells were seeded onto 96-well plates at density of 2,000 cells/well in an MEM without serum or with 1 μg/mL of IGF1, 2% fat-free fetal bovine serum, or 2% fetal bovine serum. The cell growth was estimated by WST-1 assays after 3 days. The experiments were performed in triplicate.

Animal Studies with Fatostatin A

Male mice (129Sv background) were housed under controlled conditions (12-hr light/dark cycle; 25° C.) in the Animal Care Center at Baylor College of Medicine and had ad libitum access to standard laboratory chow (Purina Mills) and water. Fatostatin A was administered intraperitoneally (30 mg/kg; 150 μL) to 5-6 month old male mice (129Sv background) using two different protocols. First protocol involves fasting the mice for 48 hrs, followed by refeeding fat free diet for another 48 hrs. This treatment induces both activities and levels of lipogenic enzymes such as ACC and FAS in addition to SREBPs. The administration of fatostatin A or 10% DMSO in PBS to control groups (n=5) started 24 hrs before the fasting and continued daily until the end of the experiment.

In the second protocol, two groups of male mice (n=5) were treated daily for two weeks with either 30 mg/kg fatostatin A or 10% DMSO in PBS. Food intake and body weight were measured daily. At the end of the experiments, the mice were briefly fasted for 4-5 hrs, and their blood was withdrawn for determination of serum constituents. The mice were then sacrificed, and their livers were quickly removed and ground to powder in liquid nitrogen. The powdered tissues were suspended in 10 ml of PBS containing 0.1 mM PMSF, 5 mM benzamidine, and 5 mg/mL protease inhibitor cocktail (Roche), homogenized using Polytron (3×30 Sec, at a high speed), and sonicated briefly to degrade DNA. The extracts were clarified by centrifugation at 16,000×g for 20 min. The samples were then subjected to western blot analysis using commercially available antibodies against FAS and SREBP-1. FAS and ACC activities were determined as described earlier (Mao et al., 2006).

Example 7

Fatostatin A Prevents Fatty Liver, Reduces Hyperglycemia and Induces Weight Loss in ob/ob Mice Despite the efforts to unravel the networks that regulate food intake and energy balance, it is not fully understood how obesity causes these disease. The effect of fatostatin A on male ob mice was investigated, specifically its effect to prevent weight increase by reducing white adipose size, diabetic conditions and fatty liver. As mentioned earlier, fatostatin A is an inhibitor of the master control of transcription by inhibiting the action of SREBP-1. Normal mice treated with fatostatin A lost weight and had lower levels of glucose and cholesterol. Fatostatin A reduced the active mature form of SREBP-1 in the liver of treated mice compared to controls.

SREBP-1 and -2 play related but distinct roles in biosynthesis of fatty acids and cholesterol. SREBP-1 preferentially activate the genes required for fatty acid synthesis, and SREBP-2 favors cholesterogenesis. Since fatostatin A blocks the activation of SREBP-1 and perhaps SREBP-2, in specific embodiments of the invention administration of fatostatin A into obese ob/ob mice transiently modulates the biosynthesis of both fatty acids and cholesterol and reveals interesting phenotypes in the obese mice.

The Effect of Fatostatin A on Body Weight and Food Intake

The study employed 4-5 week old male ob/ob mice of average weight of about 23 g/mouse. Fatostatin A (30 mg/kg/day) was delivered intraperitoneally daily, and body weight and food intake were measured. As shown in FIGS. 8A-8B, the increase in body weight of the treated mice was significantly lower than the controls. At the end of first week of treatment ob control mice injected with DMSO gained on average of 4.82 g/mouse (from 23.58±0.62 to 28.40±1.45), whereas the fatostatin treated group gained about 3.37 g/mouse (23.08±1.53 to 26.45±1.2 g/mouse), (p=0.03). After 28 days of treatment the fatostatin A treated group weighed about 12% less than the controls weeks (32.1±1.4 compared to 36.2±2.2 g/mouse for the fatostatin) (P=0.02). The accumulative food intake was similar in both groups FIG. 8C). On average, in the treated group, food intake was not significantly different from the controls being 5.4±1.5 compared to 5.9±1.4 g/mouse. day respectively.

Effect of Fatostatin A on Glucose and Lipids Profile in the Blood

One of the most distinct phenotypes in ob/ob mice is hyperglycemia as a result of insulin resistance conditions. To determine the effect of the fatostatin A on blood glucose and lipids, the serum levels of glucose, triglycerides, and cholesterol were analyzed in ob/ob mice fed with standard diet.

As shown in FIGS. 9A-9H, the glucose levels after over night fasting, in serum from treated animals were about 70% lower than the controls; 153.2±30.5 and 429.4±87 mg/dl respectively (P=0.003). The glucose levels in the serum of treated animals became comparable to that of wt mice with functional ob gene, whereas the control mice that were given DMSO were hyperglycemic as expected. Interestingly, ketone bodies (R-hydroxy butyrate) increased about seven fold in the treated animals compared to the controls; 3.62±1.41 and 0.5±0.37 mg/dl respectively (P=0.004). The high levels of ketone bodies in fatostatin A animals shows a significant increase in fatty acid oxidation in livers in which the main product is ketone bodies that is secreted in the blood. Also, blood constituents that increased in the treated mice were none esterified free fatty acids (NEFA) measured in the serum, which was about 70% higher than that of the controls;

1.93±0.26 and 0.7±0.2 mEq/l (P=0.028). This increase in NEFA levels may be due to increased lipolysis from adipose tissue due to an increase in demand for fatty acid oxidation. FFA is known to be associated with insulin resistance in animals and human (Chalkley et al., 1998; Boden et al., 1994). However, despite the elevated levels of FFA in serum of fatostatin A treated ob/ob mice, the glucose level was significantly lower than the controls indicating an improvement in insulin sensitivity, possibly due to improved insulin signaling. In addition, it was recently shown that as a consequence of increased fatty acid oxidation in mouse tissues (liver, adipose and muscle) of mutant acetyl-CoA carboxylase mouse ($Acc2^{-/-}$ mutant mouse), it resulted in higher ketone bodies in the blood and increased NEFA as a result of increased lipolysis in adipocytes (Abu-Elheiga et al., 2001; Abue-Elheiga et al., 2003; Oh et al., 2005). The level of triglycerides (TG) in the serum increased about 30% in treated mice compared to controls, 115±11, and 79±12 respectively (P=0.006), indicating that fatostatin A increases secretion and mobilization of TG from the liver. The serum level of total cholesterol showed a lower trend in fatostatin treated animals being 183±16 compared to 219±18 mg/dl (P=0.06). However there was a significant decrease of about 35% in LDL (31±3 compared to 48±8; P=0.02) and a lesser decrease in HDL of about 22% (144±11 and 183±12; P=0.02). Since there was more decrease in LDL level than that of HDL in serum of fatostatin A treated mice, this shows a desirable outcome for the treatment with fatostatin A. The level of VLDL, which transports triglycerides, phospholipids, and cholesterol and is calculated based on TG levels, increased about 50% (23.1±2.3 compared to 15.8±2.4 mg/dl).

Fatostatin A Reduces the Size of Epididymal Fat and Ameliorates Fatty Liver

Figure 10C:
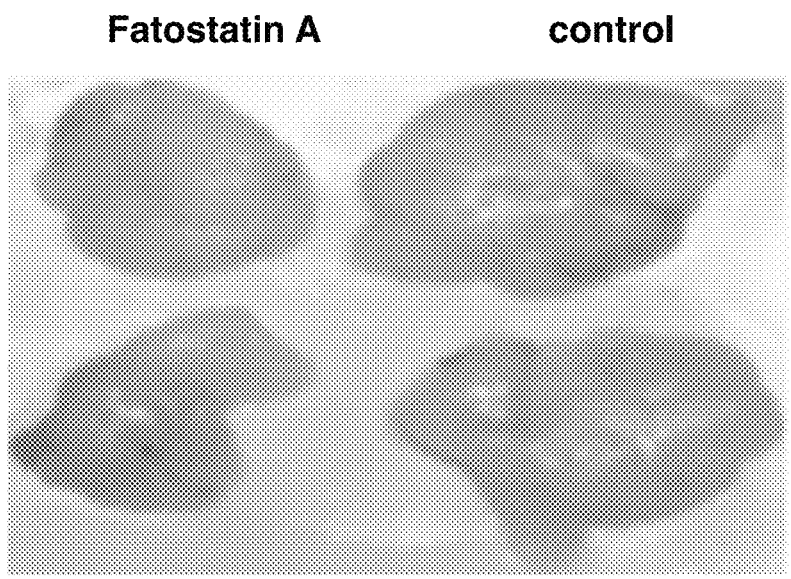
Figure 10D:
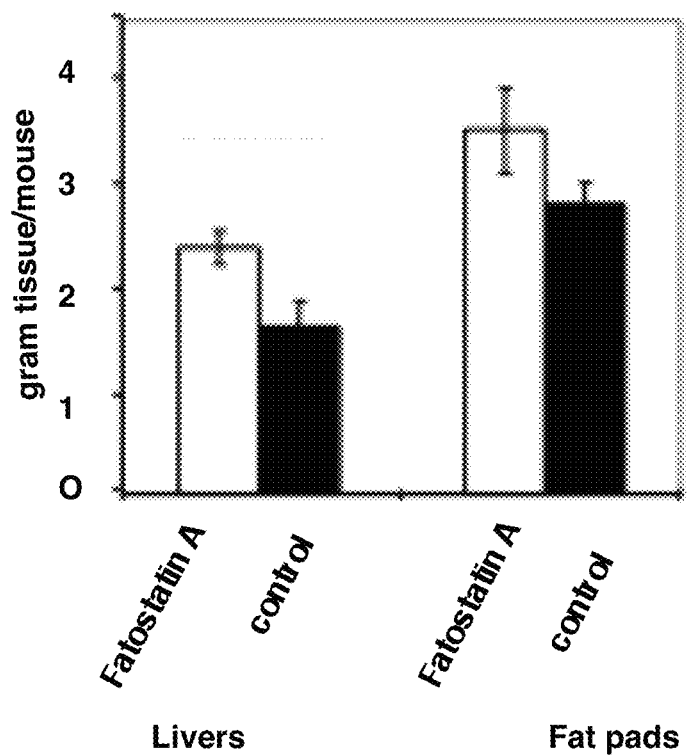

Because of uncontrolled food intake, ob/ob mice become morbidly obese and accumulate excessive levels of fat in fat tissues and in different organs, such as liver-causing non-alcoholic fatty liver conditions and insulin resistance (Hookman and Barkin, 2003). At about 8-9 weeks of age control untreated mice showed enlarged liver size and accumulated fat, as evident from pale color, compared to those treated with fatostatin A (FIG. 10A). The average weight of livers of fatostatin A treated mice was about 32% less than that of the controls (1.59±0.2 compared to 2.34±0.15; P=0.06) (FIG. 10D). Liver sections of control mice stained with oil red for lipid droplets, contained abundant lipid droplets while those of the fatostatin A treated mice were devoid of lipid droplets, which are mainly triglycerides (FIG. 10B). It has been shown that transgenic mice over expressing SREBP 1 developed fatty liver (Horton et al., 2003). However, in ob/ob mice lacking SREBP-1 ($lep^{ob/ob}$×Srebp $1^{-/-}$), fatty liver conditions were significantly improved, suggesting that SREBP 1 is a major player for the development of fatty liver in ob/ob mice (Yahagi et al., 2002).

Figure 11A:
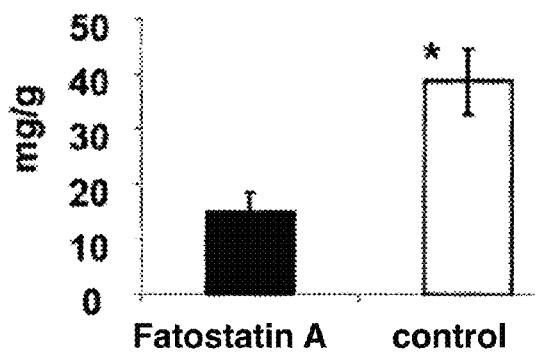
FIGS. 11A-11B shows triglycerides (FIG. 11A) and cholesterol (FIG. 11B) levels in livers of controls and fatostatin A treated ob/ob mice. Lipids were extracted from livers and triglycerides and cholesterol were quantified as described below. The data are shown as mean±SD, n=5 mice in each group (*P=0.0004; †P=0.03).
Figure 11B:
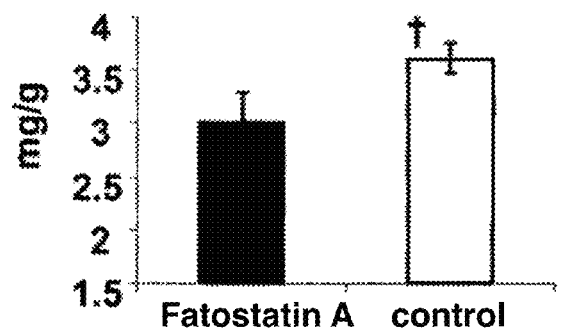

At the end of four weeks of fatostatin A treatment the treated mice weighed less than the controls. By examining the epididymal fat pads, which is the major white fat tissue, it was found that the fatostatin A treated mice has significantly smaller fat pads (FIG. 10C). The average weight of the fat pads was about 20% less than the controls (2.7±0.1 compared to 3.6±0.2; P=0.02) (FIG. 10D). The smaller fat pads may be due to decrease in storage of lipids and/or decrease in lipogenesis and enhanced fatty acid oxidation in the adipose. Previous studies with $Acc2^{-/-}$ mutant mice showed that the absence of ACC2 also resulted in less fat in livers, smaller epididymal fat pads and enhanced oxidation of fatty acids in different tissues including liver (Abu-Elheiga et al., 2001; Abu-Elheiga et al., 2003; Oh et al., 2005). It was indicated therein that enhanced fatty acid oxidation, due to lack of inhibition by ACC2-produced malonyl-CoA, on carnitine palmitoyltransferase, the mice become highly insulin sensitive and protected against diet-inducing obesity and diabetes. In specific aspects, down regulation of ACC enzymes by fatostatin A increases fatty acid oxidation and inhibits fatty acid synthesis in different tissues such as liver, adipose and muscle, for example. The TG and cholesterol levels were determined in livers of fatostatin A treated ob/ob mice and compared to ob/b controls. As shown in FIG. 11A, the TG levels in livers of treated mice were reduced by about 65% (14.8±3.7 and 38.7±6.0 mg/gram liver respectively; P=0.0004). The cholesterol levels in liver were also reduced by fatostatin A by more than 20% (2.8±0.5 and 3.6±0.1; P=0.03) (FIG. 11B). These results further confirm the Oil Red O staining and indicate that fatty liver in ob/ob mice, which is in part caused by increased hepatic lipogenesis, can be completely prevented by treatment with fatostatin A. The reduction of these lipids in liver of treated ob/ob mice is due to significant inhibition of lipogenic enzymes needed to synthesize TG and cholesterol or their precursors, in specific aspects of the invention. In addition, due to increased demand for fatty acid oxidation by different mice tissues, including the liver there is an increase in lipase liver activity and also enhanced mobilization of these lipids from liver to the circulation for utilization by different fatty acid oxidizing tissues such as heart and muscles. In specific aspects, this is related to the higher level of TG in blood of fatostatin A treated ob/ob mice.

Fatostatin A Downregulates Lipogenic Enzymes in ob/b Mice Liver

Figure 12A:
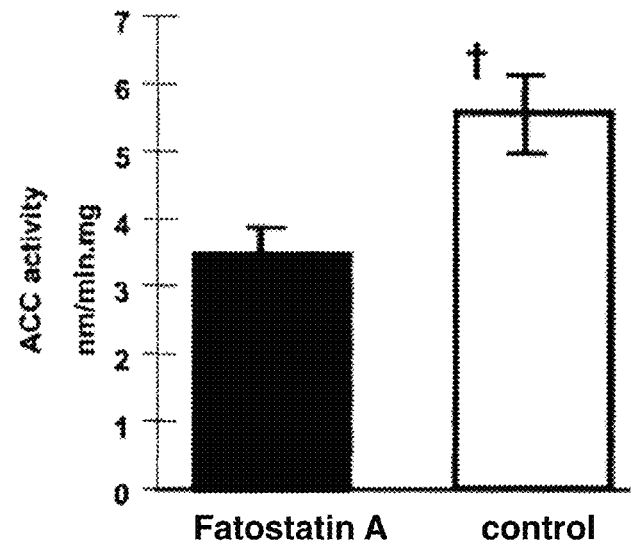
FIGS. 12A-12D demonstrate that fatostatin A reduces the expression levels and activities of lipogenic enzymes.
Figure 12B:
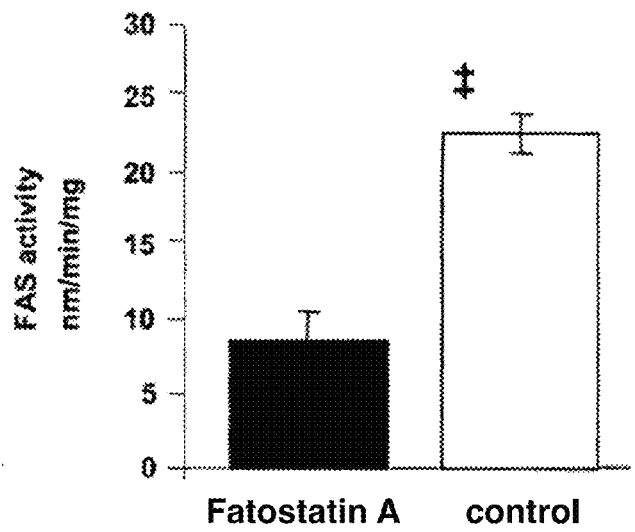
Figure 12C:
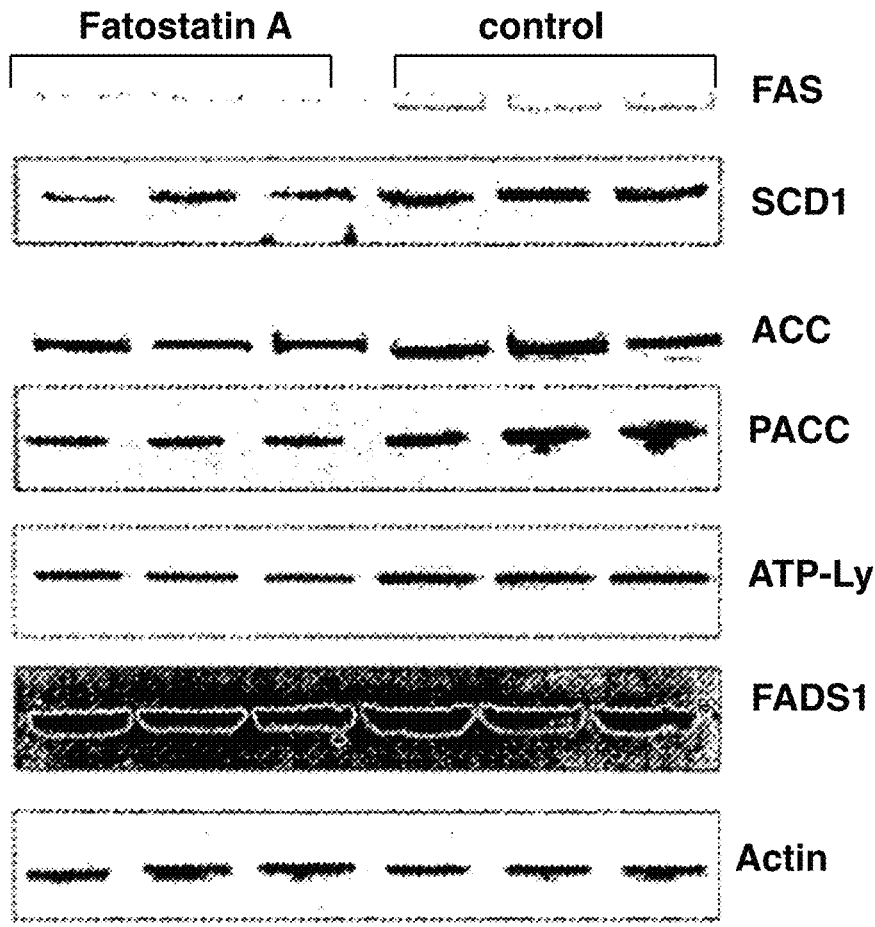

Enzymes in lipogenic pathways are regulated by transcription factors, such as PPAR and SREBPs. The effect of fatostatin A on lipogenic enzymes levels and activities in treated ob/ob mice was examined. The activity of acetyl-CoA carboxylase (ACC), which carries out the rate-limiting step in fatty acid synthesis, was determined. ACC catalyzes the carboxylation of acetyl-CoA to yield malonyl-CoA, the building block for fatty acid synthesis, which is carried out by another multifunctional enzyme, fatty acid synthase (FAS). In addition to the role of malonyl-CoA in fatty acid synthesis, it plays an important role in of fatty acid oxidation by inhibiting carnitine palmitoyl transferase 1 (CPT 1). The lipogenic enzymes are significantly induced in ob/ob mice, partly explaining the morbidly obese phenotype of these mice. The activity of ACC in liver extracts of fatostatin A treated mice decreased by about 40% (3.44±0.44 compared to 5.55±0.57 n mol/min·mg) (FIG. 12A). Fatty acid synthase activity was also significantly downregulated in liver extracts of fatostatin A treated ob/ob mice. FAS activity was reduced by more than 70% in the treated mice (8.64±1.91 compare to 22.6±1.37 n mol/min·mg) (FIG. 12B). The decrease in both ACC and FAS activities is due to reduction in the expression levels for both enzymes, as shown by western blot analysis for both enzymes (FIG. 12C). Their product fatty acids, C14:0 and C16:0, are significantly lower (about 50%) in the livers of fatostatin treated ob/ob mice than the in the livers of untreated control mice (Table 2).

Figure 12D:
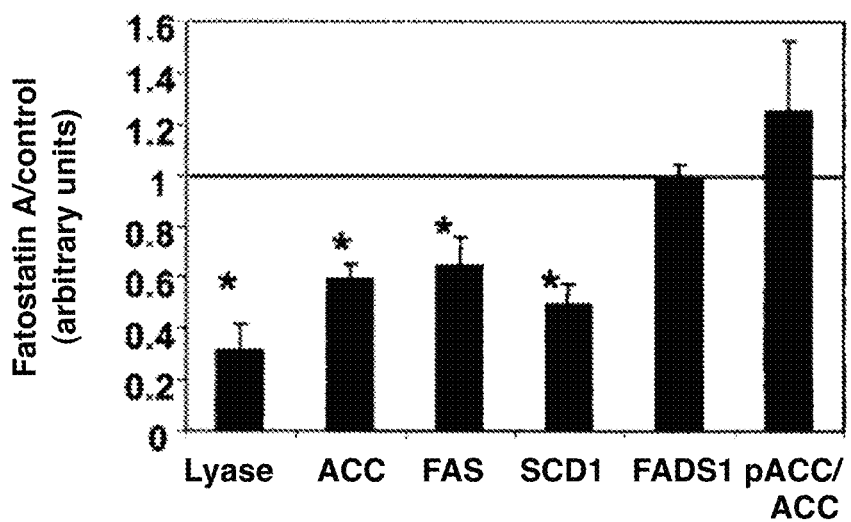

ACC is acutely regulated by phosphorylation/dephosphorylation mechanism, resulting in inhibition and activation of the enzyme, respectively. As shown in FIG. 12C, the level of phosphor-ACC was higher in the control group, however because the expression level of ACC is also higher and to the same level, this suggests that fatostatin A, does not alter the specific phosphorylation level (P-ACC/ACC protein). These results indicate that the downregulation of ACC activity is solely due to decreased levels of the enzyme and not to a decrease in the phosphorylation status (FIGS. 12C-12D). It was shown previously that in liver there are two ACC isoforms; ACC1 (the dominant isoform in liver) and ACC2 (dominant isoform in muscle) which play distinct roles in regulating lipid synthesis and oxidation, respectively. The reduction in ACC and FAS activities indicate that lipogenesis is reduced, whereas fat burning is significantly enhanced in liver of fatostatin A treated mice, which is consistent with the seven fold increase in ketone bodies in blood of ob/ob fatostatin A treated mice as shown in FIGS. 9A-9H. The level of two key enzymes in fatty acid metabolism, which are also under transcription regulation of SREBP-1, ATP citrate lyase (ACL) and Steroyl-CoA desaturase 1 (SCD1), was determined. The protein level of ACL that converts cytosolic citrate into acetyl-CoA, which is the substrate for ACC to yield malonyl-CoA for fatty acid synthesis, was reduced about 70% in liver extracts of fatostatin A mice. This downregulation in ACL level further amplify the effect of fatostatin A on the reduction in the lipogenic process in lipogenic tissues such a liver. SCD1 catalyzes the rate-limiting step in the biosynthesis of monounsaturated fatty acids, by introducing a Cis double bond in Δ9 position of fatty acyl-CoA, such as palmitoyl-CoA and stearoyl-CoA. The products, palmitoleoyl-CoA (16:1) and oleoyl-CoA (18:1) are important components of triglycerides and cholesterol esters and deletion of SCD1 in mice including ob/ob mice resulted in increased metabolic rate, reduced adiposity, preventing fatty liver and protecting against diabetes induced by diet. As shown in FIG. 12D, the protein level of SCD1 was reduced about 50% in liver extracts of fatostatin A treated mice compared to the controls. This was confirmed by the reduction by about 70% of the monounsaturated fatty acids C16:1, C18:1 and C20:1 as well as the reduction by about 50% of the desaturation of their elongated products (C18:2)N-6, (C18:3)N-6, (C20:2)N-6, and (C20-3)N-6 (Table 2). This effect on the reduction in SCD1 is an important factor in weight reduction and decreases TG level in liver and protection against fatty liver, in specific embodiments of the invention. Interestingly, the protein level of FADS 1 or Δ5 Desaturase did not change as a result of fatostatin A treatment.

Liver samples (100 mg) obtained from fatostatin A-treated ob/ob mice and non-treated control mice and stored at −80° C. until analyzed for fatty acid contents. The fatty acids were extracted according to Folch's protocol and quantitatively analyzed using gas chromatography-mass spectrometry (GC-SM). As shown in the above table, there is about 50% reduction of C14:0 and C16:0, the products of the de novo fatty acid synthesis, and about 70% reduction of monounsaturated fatty acids C16:1, C18:1 and C20:1 and their elongation-desaturation products (C18:2)N-6, (C18:3)N-6, (C20:2)N-6, (C20-3)N-6 and (C20:5)N-3. Myristate (C14:0) and palmitate (C16:0), the products of FAS, were reduced by about 50% ($P<0.05$). There was no change in C18 levels, which is derived not only from de novo fatty acid synthesis by FAS, but also from food and chain elongation system. Interestingly there was a strong trend in lowering the C20:0 by about 15% ($P+0.059$) and an increase of 30% in C24:0 ($P=0.05$). In parallel to the significant decreases in long-chain saturated fatty acids, results show that there were significant reductions of about 70% in the levels of monounsaturated fatty acids C16:1, C18:1 and C20:1 ($P<0.004$). Also, the levels of polyunsaturated long-chain fatty acids (18:2)N-6, (18:3)N-6, (20:2)N-6, (20:3)N-6 and (20:5)N-3 were reduced 30-60%. These reductions are the result of down regulation of key enzymes in the lipogenic pathways (FAS, ACC and SCD, ACL) at transcription and translation. These results help explain the effect of fatostatin A in ameliorating fatty liver conditions by reducing the triglyceride levels made in the liver.

Downregulation of mRNA Levels of Lipogenic Enzymes

Figure 13:
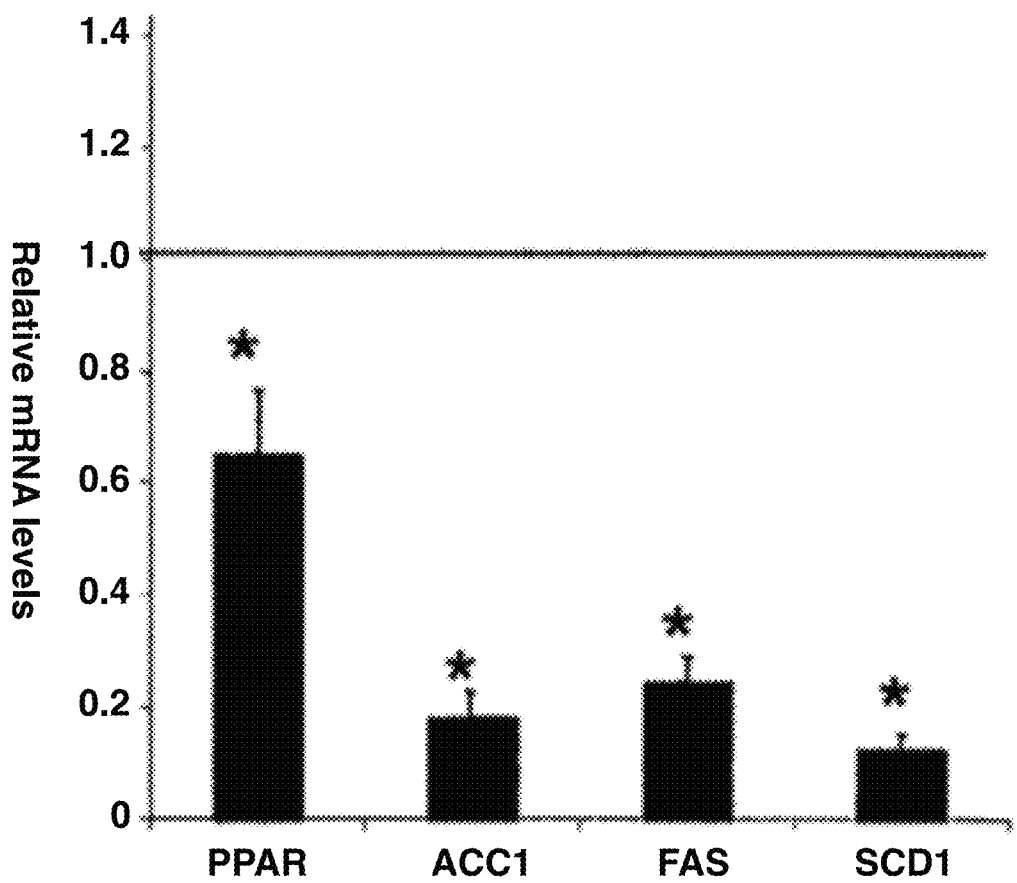
FIG. 13 shows transcript levels of liver lipogenic enzymes in control relative to fatostatin A ob/ob mice. mRNA levels for each gene was normalized to actin. RNA was isolated from control and fatostatin A treated mice (n=5) and measured by real-time quantitative RT-PCR. *P<0.05 vs. control.
Figure 14A:
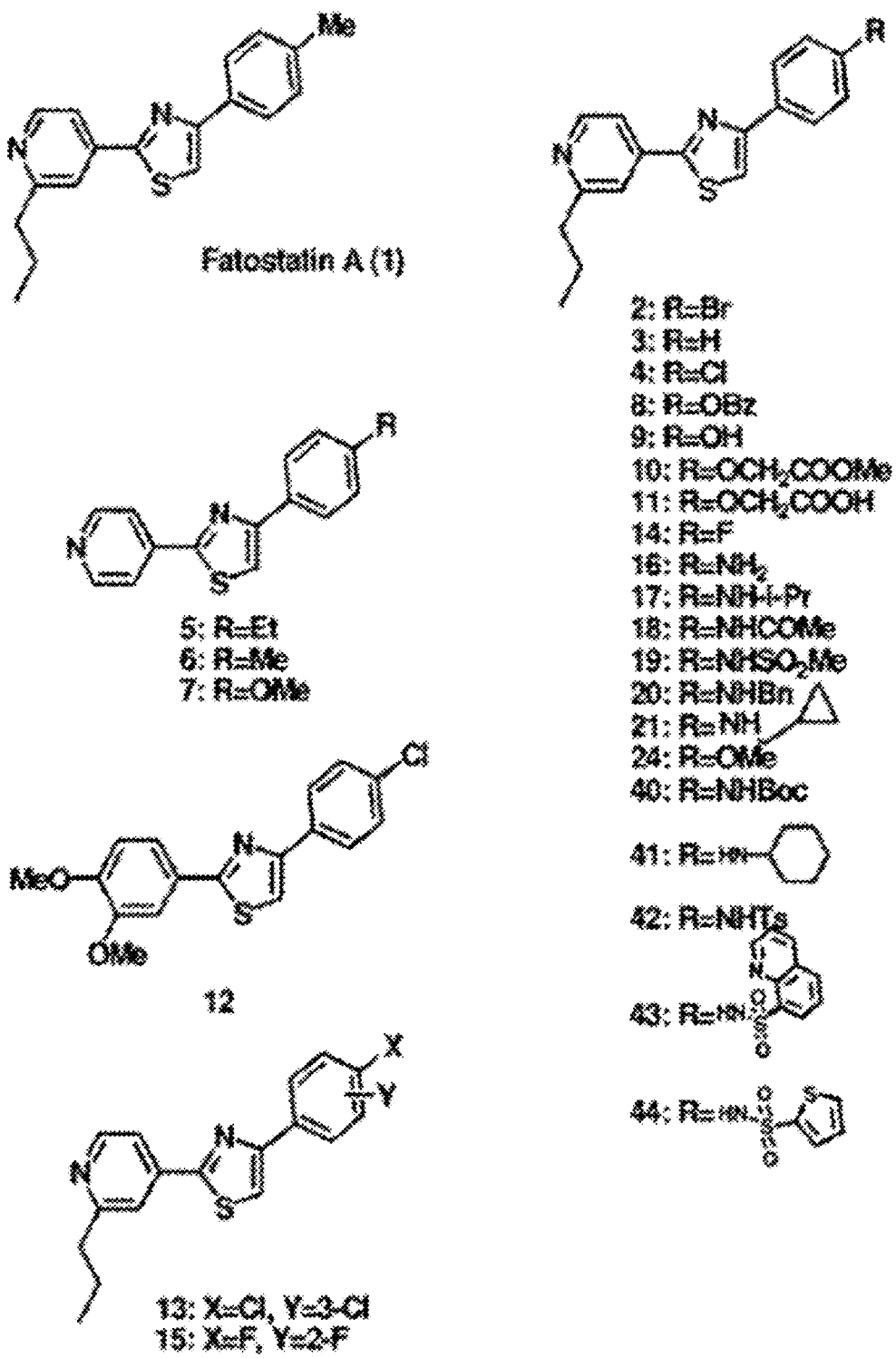
Figure 14B:
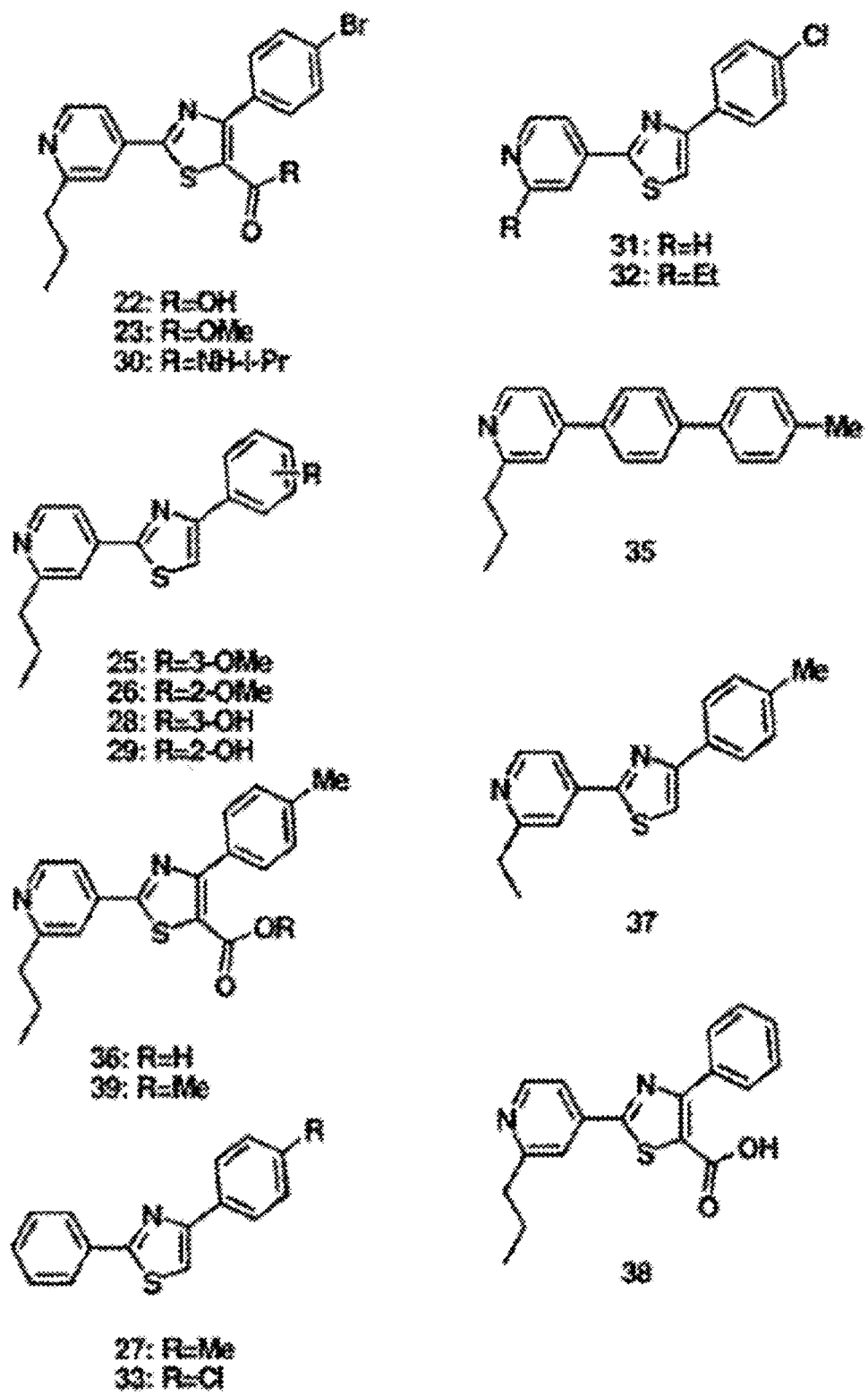
Figure 14D:
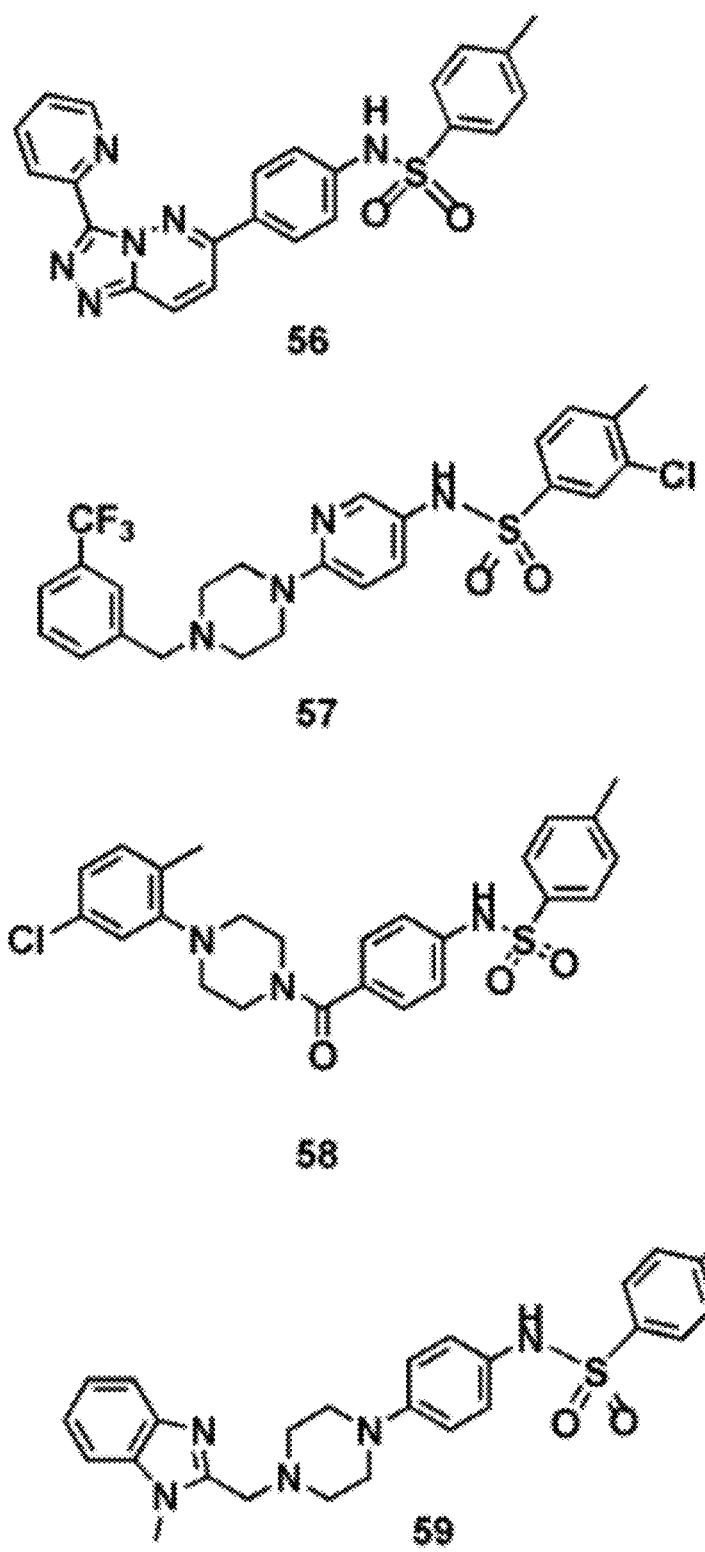
Figure 14E:
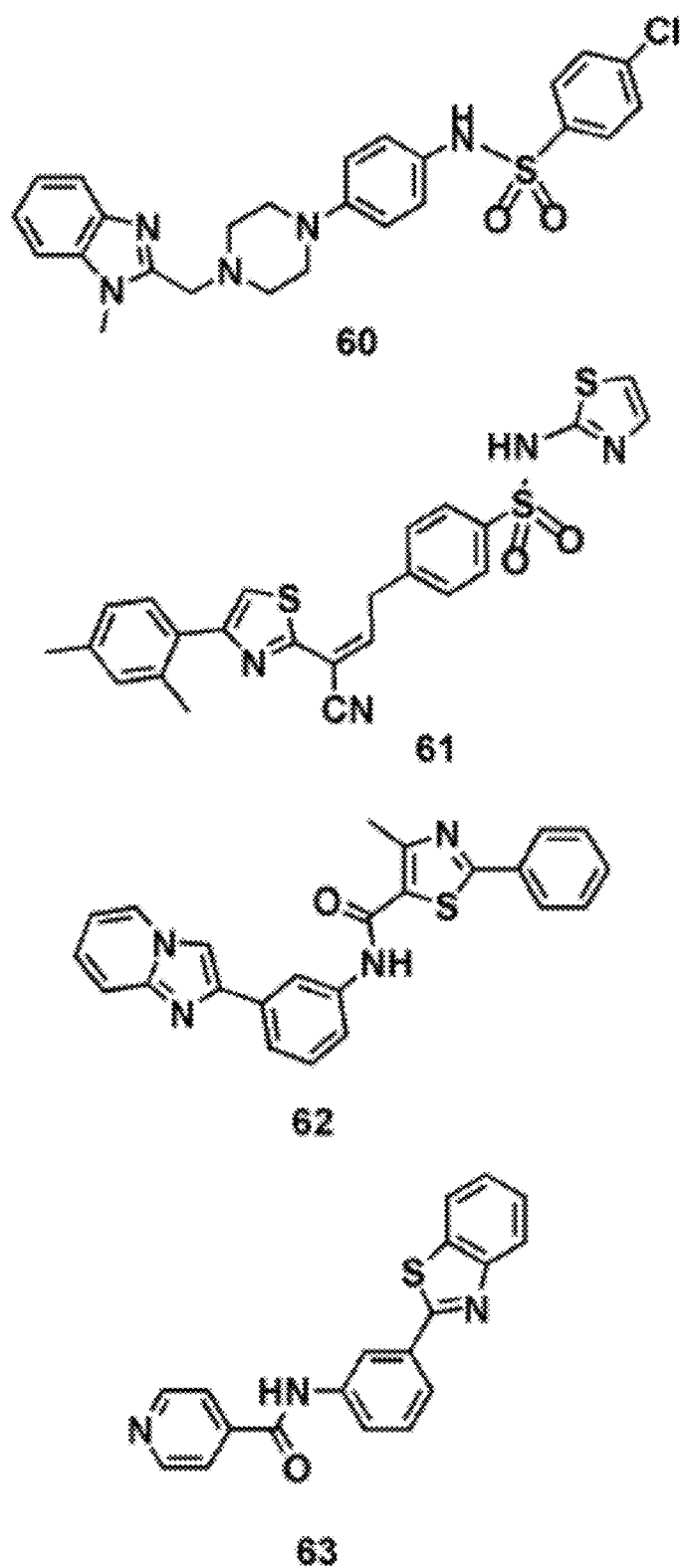

The decrease in protein levels can be attributed to a transcriptional or translational regulation. Real time PCR was used to determined the levels of mRNA levels of representatives of lipogenic genes ACC1, FAS and SCD1 in addition to the lipogenic transcription factor PPAR γ. There was about 80% reduction in the mRNA levels of ACC1, FAS and SCD1 (FIG. 13). These results are consistent with lower levels of enzyme proteins and activities, and strongly indicate that fatostatin A lowers lipogenesis by inhibiting the maturation of SREBP-1. The down regulation of lipogenic enzyme involves

TABLE 2

Gas Chromatography-Mass Spectrometry (GC-MS) Analyses Of Fatty Acids in the Livers of OB/OB Treated Mice and Their Untreated Control

| Fatty Acid | Fatostatin A μmole/gram liver | Control μmole/gram liver | Ratio treated:control | P value |
|---|---|---|---|---|
| (14:0) | 1224.567 ± 508.88 | 2378.586 ± 329.454 | 0.51483 | 0.047781 |
| (16:0) | 37143.23 ± 3656.16 | 85044.75 ± 5716.175 | 0.436749 | 0.001619 |
| (18:0) | 15067.14 ± 916.48 | 14129.2 ± 272.7029 | 1.066383 | 0.260833 |
| (20:0) | 164.3537 ± 22.89 | 192.9773 ± 16.46977 | 0.851674 | 0.059842 |
| (22:0) | 116.1305 ± 25.97 | 91.74762 ± 12.60782 | 1.26576 | 0.2499 |
| (24:0) | 157.8261 ± 7.02 | 120.6449 ± 19.37201 | 1.308188 | 0.052305 |
| (16:1) | 11429.29 ± 227.5 | 34787.26 ± 4482.311 | 0.328548 | 0.005542 |
| (18:1) | 44471.72 ± 8840.37 | 152218.4 ± 12872.57 | 0.292157 | 0.001621 |
| (20:1) | 593.7212 ± 119.68 | 1829.537 ± 230.8927 | 0.32452 | 0.00368 |
| (22:1) | 94.94588 ± 14.91 | 109.0117 ± 11.47413 | 0.870969 | 0.379216 |
| (24:1) | 397.92 ± 216.3 | 234.2073 ± 26.9417 | 1.699008 | 0.214302 |
| (18:2)N-6 | 29673.93 ± 2456.22 | 46513.4 ± 2825.032 | 0.637965 | 0.00455 |
| (18:3)N-6 | 237.1671 ± 40.5 | 560.4358 ± 61.89641 | 0.423183 | 0.00546 |
| (20:2)N-6 | 426.6694 ± 63.52 | 914.0388 ± 90.59441 | 0.466796 | 0.001424 |
| (20:3)N-6 | 1630.394 ± 193.18 | 2589.236 ± 154.791 | 0.629682 | 0.008568 |
| (20:4)N-6 | 8747.289 ± 781.41 | 7772.095 ± 110.7878 | 1.125474 | 0.171108 |
| (22:4)N-6 | 280.2708 ± 46.1 | 292.2569 ± 11.81504 | 0.958988 | 0.810355 |
| (22:5)N-6 | 172.9715 ± 64.89 | 146.5646 ± 14.54166 | 1.180173 | 0.879433 |
| (18:3)N-3 | 4416.975 ± 643.658 | 3625.879 ± 220.5747 | 1.21818 | 0.703923 |
| (20:5)N-3 | 2145.643 ± 265.17 | 3067.856 ± 299.7701 | 0.699395 | 0.04467 |
| (22:5)N-3 | 1720.424 ± 221.16 | 2338.451 ± 234.2185 | 0.735711 | 0.092988 |
| (22:6)N-3 | 9223.38 ± 700.31 | 8718.014 ± 532.5817 | 1.057968 | 0.448218 | one of its main transcription factors, PPAR γ, in specific embodiments. The mRNA level of this transcription factor was reduced by about 40% in extracts of fatostatin A treated mice (FIG. 13). Since, ob/ob mice treated with fatostatin A reduced hyperglycemia and prevented fatty liver, this indicates that PPAR γ in liver is one of several factors that may affect these pathological conditions, in specific aspects. In summary, Fatostatin A through its action on SREBP-1 ameliorated fatty liver by reducing hepatic TG storage, reduced adiposity and lowered hyperglycemia in treated ob/ob mice. These studies indicate that fatostatin A and its analogs are useful agents against obesity, fatty liver and diabetes, for example.

Four- to 5-week old homozygous male obese (ob/ob) mice (C57BL/6J, The Jackson Laboratory, Bar Harbor, Me.) were housed under controlled conditions (12-hr light/dark cycle; 25° C.). The animals were housed 5 per cage and had ad libitum access to standard laboratory chow (Purina Mills, Richmond Ind.) and water for one week after their arrival. On first day of the experiment and every day thereafter the weight of the mice and the amount of the food consumed were measured. The weight of mice and food remaining were measured daily between 3-5 p.m. before the ip injection of fatostatin A (30 mg/kg; 150 µL). The administration of Fatostatin A or 10% DMSO in PBS to control groups (n=5) continued daily for four weeks till the end of the study.

After 28 days of daily injection of fatostatin A mice were fasted overnight and blood was withdrawn and Whole blood glucose and 3-hydroxybutyrate were measured with a Glucometer Precision Xtra (Abbott). For determination of serum constituents. Glucose, triglyceride and cholesterol measurements were done by the Comparative Pathology Laboratory (Baylor College of Medicine). Serum non-esterified fatty acids (NEFA) were measured by using NEFA C kit (Wako Chemicals, Richmond, Va.).

Mice were sacrificed and weights of livers, and Epididymal fat pads were determined. Frozen sections of Liver slices from individual animals were stained with Oil Red O to visualize the fat droplets (TG) in liver slices as described earlier (Abu-Elheiga et al., 2001). The remaining liver tissues were frozen in liquid nitrogen and kept at −80° C. for further analysis.

Liver triglyceride and cholesterol contents were carried out as described in the reference (Chandler, et al., 2003) using Cholesterol E Kit (Wako) and Infinity Triglyceride Kit (Thermo Electron, Melbourne, Australia), adapted for colorimetric analysis in 96-well plate format.

Enzymatic Activities and Western Blot Analyses

A portion of the frozen liver was ground to powder in liquid nitrogen. The powdered tissues were suspended in 10 ml of PBS containing 0.1 mM PMSF, 5 mM benzamidine, and 5 mg/ml protease inhibitor cocktail (Roche), and homogenized using Polytron (3×30 Sec, at high speed) and sonicated briefly to degrade DNA. The extracts were clarified by centrifugation at 16,000×g for 20 min. Protein concentrations in the supernatant were determined, and subjected to western blot analysis using commercially available antibodies against the following enzymes: FAS (BD Biosciences), citrate lyase SCD1, FADS1, ACC and phospho-ACC antibodies. The proteins were visualized using Amersham ECL Plus™ Western Blotting Detection Reagents. The intensity of the specific bands of proteins of interest were scanned and normalized against beta-actin for quantifications. FAS and ACC activities from the liver extracts were determined as described earlier (Mao et al., 2006).

Quantitative Real Time PCR

Total RNA was prepared from mouse tissues using TRIzol reagent (Invitrogen). Equal amounts of RNA from 5 mice were pooled and treated with DNase I (Turbo DNA-free, Ambion, Inc.). First stranded cDNA was synthesized from 2 µg of DNase I-treated total RNA with random hexamer primer using Superscript II RNase H-reverse transcriptase (Invitrogen). The real time PCR contained, in a final volume of 20 µl, 10 ng of reverse transcribed total RNA, 0.5 µM forward and reverse primers, and 10 µl of 2× master mix from DyNAmo HS SYBR Green qPCR kit (Finnzymes). PCR was carried out in 96-well plate using DNA Engine Opticon System (MJ Research, Inc). All reactions were done in triplicate and the relative amounts of mRNAs were calculated using the comparative C(t) method. The cycle threshold C(t) was calculated using the Opticon Monitor software 2.02 (MJ Research). Mouse β-actin mRNA was used as the internal control. Data were expressed as the mean±SD. Difference between two groups was assessed using the unpaired two-tailed Student t-test.

Example 8

Identification of Target Molecules of Fatostatin A and Analogs or Derivatives Thereof In certain aspects of the invention, one or more targets of fatostatin A or its analog or derivative is identified. Although any suitable method may be employed for such identification, in specific embodiments the fatostatin A or analog or derivative thereof, is labeled. Exemplary labels include biotin, for example.

Example 9

Exemplary Compounds and Modifications Thereof

Figure 15:
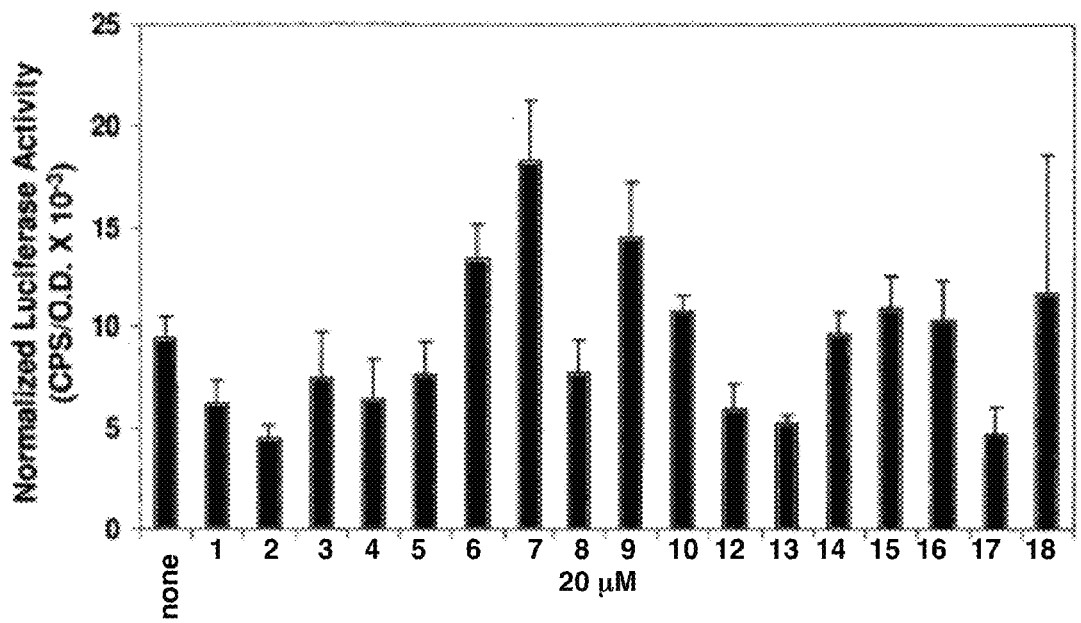
FIG. 15 demonstrates a standard luciferase reporter gene assay with exemplary analogues 2-18.
Figure 16:
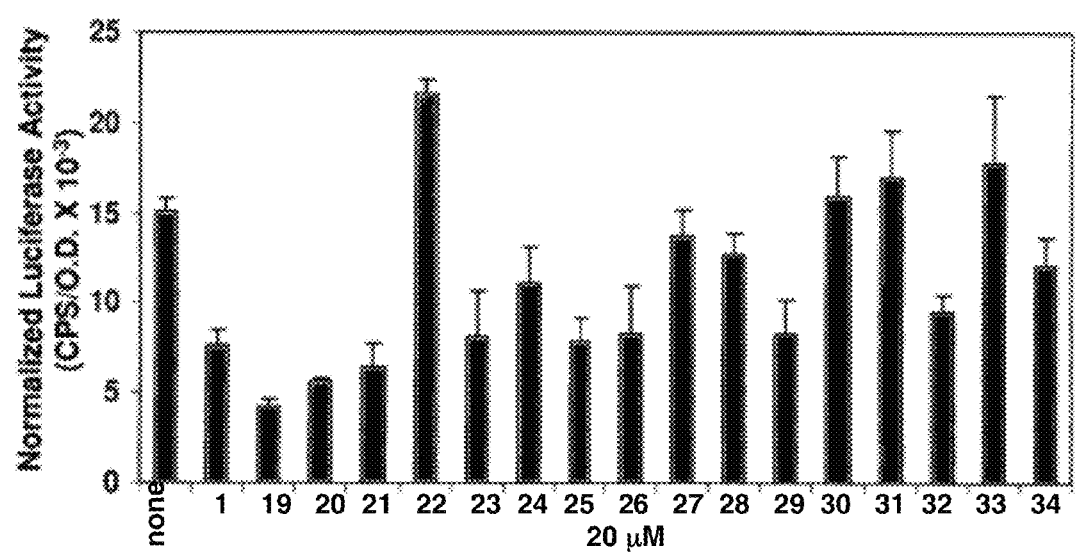
FIG. 16 shows a standard luciferase reporter gene assay with exemplary analogues 19-34.
Figure 17:
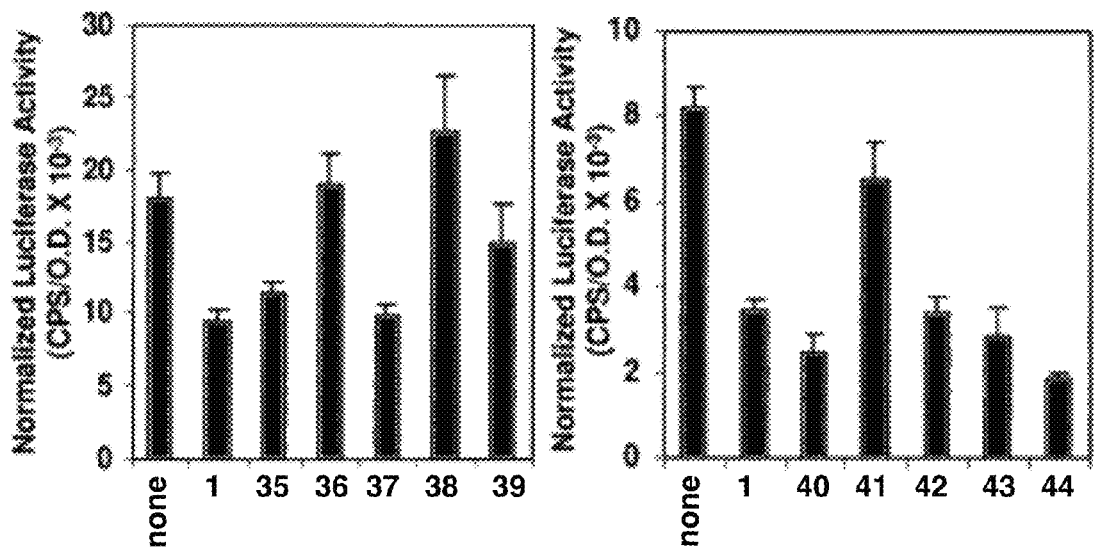
FIG. 17 provides a standard luciferase reporter gene assay with exemplary analogues 35-44.

FIGS. 14A-14F illustrate exemplary compounds of the invention, and their given names are provided in Table 3 and Table 4. FIGS. 15-17 demonstrate exemplary luciferase reporter gene assays for these exemplary compounds at 20 mM by the same method shown in FIG. 2A. The adipogenesis assay was performed as described (Choi et al., 2003). The analogues that completely inhibited the formation of oil droplets in cells were scored to be adipogenesis-inhibiting analogues.

TABLE 3

Exemplary Compounds of the Invention

| Name | entry | Luc/Gal | STDEV | Inhibition of adipogenesis |
|---|---|---|---|---|
| | none | 9.4426 | 1.0577 | |
| 2-propyl-4-(4-p-tolylthiazol-2-yl)pyridine | 1 | 6.2297 | 1.1014 | + |
| 4-(4-(4-bromophenyl)thiazol-2-yl)-2-propylpyridine | 2 | 4.5130 | 0.6176 | − |
| 4-(4-phenylthiazol-2-yl)-2-propylpyridine | 3 | 7.4643 | 2.2215 | − |

TABLE 3-continued

Exemplary Compounds of the Invention

| Name | entry | Luc/Gal | STDEV | Inhibition of adipogenesis |
|---|---|---|---|---|
| 4-(4-(4-chlorophenyl)thiazol-2-yl)-2-propylpyridine | 4 | 6.3808 | 2.0425 | − |
| 4-(4-ethylphenyl)thiazol-2-yl)pyridine | 5 | 7.6190 | 1.6221 | − |
| 4-(4-p-tolylthiazol-2-yl)pyridine | 6 | 13.4689 | 1.6735 | − |
| 4-(4-(4-methoxyphenyl)thiazol-2-yl)pyridine | 7 | 18.3174 | 2.9172 | − |
| 4-(2-(2-propylpyridin-4-yl)thiazol-4-yl)phenyl benzoate | 8 | 7.7585 | 1.6193 | + |
| 4-(2-(2-propylpyridin-4-yl)thiazol-4-yl)phenol | 9 | 14.5234 | 2.7276 | + |
| methyl 2-(4-(2-(2-propylpyridin-4-yl)thiazol-4-yl)phenoxy)acetate | 10 | 10.7717 | 0.8662 | − |
| 4-(4-chlorophenyl)-2-(3,4-dimethoxyphenyl)thiazole | 12 | 5.9214 | 1.2693 | − |
| 4-(4-(3,4-dichlorophenyl)thiazol-2-yl)-2-propylpyridine | 13 | 5.2391 | 0.4021 | − |
| 4-(4-(4-fluorophenyl)thiazol-2-yl)-2-propylpyridine | 14 | 9.6605 | 0.9824 | − |
| 4-(4-(2,4-difluorophenyl)thiazol-2-yl)-2-propylpyridine | 15 | 10.8383 | 1.7661 | − |
| 4-(2-(2-propylpyridin-4-yl)thiazol-4-yl)benzenamine | 16 | 10.3338 | 2.0763 | + |
| N-isopropyl-4-(2-(2-propylpyridin-4-yl)thiazol-4-yl)benzenamine | 17 | 4.7079 | 1.2781 | + |
| N-(4-(2-(2-propylpyridin-4-yl)thiazol-4-yl)phenyl)acetamide | 18 | 11.7685 | 6.8358 | + |
|  | None | 15.0759 | 0.8305 |  |
| 2-propyl-4-(4-p-tolylthiazol-2-yl)pyridine | 1 | 7.5537 | 0.9784 | + |
| N-(4-(2-(2-propylpyridin-4-yl)thiazol-4-yl)phenyl)methanesulfonamide | 19 | 4.1981 | 0.4653 | + |
| N-benzyl-4-(2-(2-propylpyridin-4-yl)thiazol-4-yl)benzenamine | 20 | 5.6748 | 0.0613 | + |
| N-(cyclopropylmethyl)-4-(2-(2-propylpyridin-4-yl)thiazol-4-yl)benzenamine | 21 | 6.4378 | 1.2736 | + |
| 4-(4-bromophenyl)-2-(2-propylpyridin-4-yl)thiazole-5-carboxylic acid | 22 | 21.5911 | 0.8383 | − |
| methyl 4-(4-bromophenyl)-2-(2-propylpyridin-4-yl)thiazole-5-carboxylate | 23 | 8.1137 | 2.5369 | + |
| 4-(4-(4-methoxyphenyl)thiazol-2-yl)-2-propylpyridine | 24 | 11.0367 | 2.1112 | − |
| 4-(4-(3-methoxyphenyl)thiazol-2-yl)-2-propylpyridine | 25 | 7.8536 | 1.2799 | − |
| 4-(4-(2-methoxyphenyl)thiazol-2-yl)-2-propylpyridine | 26 | 8.3046 | 2.6780 | + |
| 2-phenyl-4-p-tolylthiazole | 27 | 13.8222 | 1.3938 | − |
| 3-(2-(2-propylpyridin-4-yl)thiazol-4-yl)phenol | 28 | 12.7791 | 1.1429 | − |
| 2-(2-(2-propylpyridin-4-yl)thiazol-4-yl)phenol | 29 | 8.2379 | 1.9501 | − |
| 4-(4-bromophenyl)-N-isopropyl-2-(2-propylpyridin-4-yl)thiazole-5-carboxamide | 30 | 16.0226 | 2.1917 | − |
| 4-(4-(4-chlorophenyl)thiazol-2-yl)pyridine | 31 | 16.9971 | 2.6512 | − |
| 4-(4-(4-chlorophenyl)thiazol-2-yl)-2-ethylpyridine | 32 | 9.5798 | 0.8524 | − |
| 4-(4-chlorophenyl)-2-phenylthiazole | 33 | 17.8175 | 3.7158 | − |
| 2-propyl-4-(4-(thiophen-2-yl)thiazol-2-yl)pyridine | 34 | 12.1593 | 1.5587 | + |
| 2-phenyl-4-p-tolylthiazole | 27 | 13.8222 | 1.3938 | − |
|  | None | 18 | 2 |  |
| 2-propyl-4-(4-p-tolylthiazol-2-yl)pyridine | 1 | 9.413845 | 0.840651 | + |
| 4-(4'-methyl[1,1'-biphenyl]-4-yl)-2-propyl)pyridine | 35 | 11.3586 | 0.881475 | + |
| 2-(2-propylpyridin-4-yl)-4-p-tolylthiazole-5-carboxylic acid | 36 | 18.98889 | 2.082093 |  |
| 2-ethyl-4-(4-p-tolylthiazol-2-yl)pyridine | 37 | 9.869906 | 0.71108 |  |
| 4-phenyl-2-(2-propylpyridin-4-yl)thiazole-5-carboxylic acid | 38 | 22.65811 | 3.898667 |  |
| methyl 2-(2-propylpyridin-4-yl)-4-p-tolylthiazole-5-carboxylate | 39 | 14.92978 | 2.600443 |  |
|  | None | 8.2181 | 0.5097 |  |
| 2-propyl-4-(4-p-tolylthiazol-2-yl)pyridine | 1 | 3.4437 | 0.2720 |  |
| tert-butyl 4-(2-(2-propylpyridin-4-yl)thiazol-4-yl)phenylcarbamate | 40 | 2.4390 | 0.4730 |  |
| N-cyclohexyl-4-(2-(2-propylpyridin-4-yl)thiazol-4-yl)benzenamine | 41 | 6.5229 | 0.8638 |  |
| 4-(2-(2-propylpyridin-4-yl)thiazol-4-yl)-N-tosylbenzenamine | 42 | 3.3957 | 0.3619 |  |
| N-(4-(2-(2-propylpyridin-4-yl)thiazol-4-yl)phenyl)-8-quinolinesulfonamide | 43 | 2.8506 | 0.6396 |  |

TABLE 3-continued

Exemplary Compounds of the Invention

| Name | entry | Luc/Gal | STDEV | Inhibition of adipogenesis |
|---|---|---|---|---|
| N-(4-(2-(2-propylpyridin-4-yl)thiazol-4-yl)phenyl)-2-thiophenesulfonamide | 44 | 1.8538 | 0.1240 | |

TABLE 4

| Name | Compound |
|---|---|
| 4-(4-bromophenyl)-2-(pyrrolidin-2-yl)thiazole | 45 |
| 4-(4-bromophenyl)-2-(1-propylpyrrolidin-2-yl)thiazole | 46 |
| tert-butyl 2-(4-(4-bromophenyl)thiazol-2-yl)pyrrolidine-1-carboxylate | 47 |
| benzyl 2-(4-(4-bromophenyl)thiazol-2-yl)pyrrolidine-1-carboxylate | 48 |
| 3-(4-(4-bromophenyl)thiazol-2-yl)-1-propylpiperidine | 49 |
| tert-butyl 3-(4-(4-bromophenyl)thiazol-2-yl)piperidine-1-carboxylate | 50 |
| benzyl 3-(4-(4-bromophenyl)thiazol-2-yl)piperidine-1-carboxylate | 51 |
| benzyl 4-(4-(4-bromophenyl)thiazol-2-yl)piperidine-1-carboxylate | 52 |
| benzyl (R)-2-(4-(4-(methylsulfonamido)phenyl)thiazol-2-yl)pyrrolidine-1-carboxylate | 53 |
| benzyl 3-(4-(4-(methylsulfonamido)phenyl)thiazol-2-yl)piperidine-1-carboxylate | 54 |
| benzyl 4-(4-(4-(methylsulfonamido)phenyl)thiazol-2-yl)piperidine-1-carboxylate | 55 |
| 4-(3-(pyridin-2-yl)-[1,2,4]triazolo[4,3-b]pyridazin-6-yl)-N-tosylbenzenamine | 56 |
| 3-chloro-4-methyl-N-(6-(4-(3-(trifluoromethyl)benzyl)piperazin-1-yl)pyridin-3-yl)benzenesulfonamide | 57 |
| (4-(5-chloro-2-methylphenyl)piperazin-1-yl)(4-(tosylamino)phenyl)methanone | 58 |
| 4-(4-((1-methyl-1H-benzo[d]imidazole-2-yl)methyl)piperazin-1-yl)-N-tosylbenzenamine | 59 |
| 4-chloro-N-(4-(4-((1-methyl-1H-benzo[d]imidazol-2-yl)methyl)piperazin-1-yl)phenyl)benzenesulfonamide | 60 |
| (Z)-4-(3-cyano-3-(4-(2,4-dimethylphenyl)thiazol-2-yl)allyl)-N-(thiazol-2-yl)benzenesulfonamide | 61 |
| N-(3-(H-imidazo[1,2-a]pyridine-2-yl)phenyl)-4-methyl-2-phenylthiazole-5-carboxamide | 62 |
| N-(3-(benzo[d]thiazol-2-yl)phenyl)isonicotinamide | 63 |
| 3-(4-chlorophenyl)-4,5-dihydro-1-phenyl-5-(2-phenylthiazol-4-yl)-1H-pyrazole | 64 |
| N-(4-(6-methylbenzo[d]thiazol-2-yl)phenyl)-2-(N-m-tolylmethylsulfonamido)acetamide | 65 |
| N-(4-(6-methylbenzo[d]thiazol-2-yl)phenyl)-2-(N-p-tolylmethylsulfonamido)acetamide | 66 |

Furthermore, a skilled artisan recognizes that it may be suitable to modify one or more aspects of an exemplary compound to assist in identifying other suitable compounds. For example, upon determination of suitability for a particular compound for treatment and/or prevention of one or more metabolic disorders, the compound may be modified to identify other related compounds for use for the same or a different metabolic disorder. Such alterations may occur in accordance with exemplary chemical groups as described herein, in specific embodiments.

Example 10

Blockage of Fat Synthesis by Inhibiting the Activation of SREBP

Upon fat depletion in a cell, sterol regulatory element binding proteins (SREBPs) are released proteolytically from the membrane and translocated into the nucleus, where they activate transcription of the genes involved in cholesterol and fatty acid biosynthesis. In the present invention, it is shown that a small synthetic molecule that blocks adipogenesis is a selective inhibitor of the SREBP activation. The diarylthiazole derivative, called fatostatin, impairs the proteolytic activation of SREBPs, thereby decreasing the transcription of lipogenic genes in cells. The molecular target of fatostatin appears to be SREBP cleavage-activating protein (SCAP). Fatostatin blocked increases in body weight, blood glucose, and hepatic fat accumulation in obese ob/ob mice, even under uncontrolled food intake.

As described herein, fatostatin inhibits the insulin-induced adipogenesis of 3T3-L1 cells and the serum-independent growth of DU145 cells (Choi et al., 2003). Gene expression profiles of drug-treated and untreated cells were compared to gain information about specific molecular pathways affected by fatostatin. DU145 cells were treated with fatostatin or DMSO alone, and the extracted mRNA samples were analyzed by Affymetrix DNA microarrays mapping 33,000 genes. Of those genes (all of which are available at the National Center for Biotechnology Information's GenBank database on the world wide web), transcription levels of 63 genes decreased at least 35% in response to fatostatin treatment (Table 5). Thirty-four of the affected genes were directly associated with fat or sterol synthesis, such as genes encoding biosynthetic enzymes, and 18 of the affected genes have been reported to be controlled by SREBPs (Horton et al., 2003). Downregulation of the affected SREBP-responsive genes was confirmed by RT-PCR experiments. The high occurrence of the SREBP-responsive genes and fat/cholesterol biosynthesis genes in the list of the downregulated genes implies that fatostatin acts on the SREBP pathway.

Table 5 shows the results of the microarray analysis. The 18 underlined genes have been reported to be controlled by SREBPs, the genes in bold are associated with fat or sterol synthesis.

TABLE 5

| | | | | | |
|---|---|---|---|---|---|
| P | D | 0.707107 | Hs.17414 | NM_00109 | ATP citrate lyase/FL = gb: NM_001096.1 |
| P | D | 0.707107 | Hs.11223 | NM_00589 | Isocitrate dehydrogenase 1 (NADP+), soluble/FL = gb: AF020038.1 gb: AF113917 |
| P | D | 0.707107 | Hs.268012 | D89053.1 | Fatty-acid-Coenzyme A ligase, long-chain 3/FL = gb: NM_004457.2 gbz: D89053.1 gb: AF116690.1 |
| P | D | 0.707107 | Hs.155976 | AI670819 | Cullin 4B/FL = gb: NM_003588.1 gb: AB014595.1 |
| P | D | 0.707107 | Hs.41693 | BG252490 | DNAJ (Hsp40) homolog, subfamily B, member 4/FL = gb: U40992.2 gb: NM_007034.2 |
| P | D | 0.707107 | Hs.14732 | AL049699 | <u>malic enzyme 1, NADP(+)-dependent, cytosolic/FL = gb: NM_002395.2</u> |
| P | D | 0.707107 | Hs.213289 | S70123.1 | <u>low density lipoprotein receptor (familial hypercholesterolemia)</u> |
| P | D | 0.707107 | Hs.6986 | AL565516 | human glucose transporter pseudogene |
| P | D | 0.659754 | Hs.75616 | NM_014676 | seladin-1/FL = gb: AF261758.1 gb: BC004375.1 gb: NM_014762.1 |
| P | D | 0.659754 | Hs.77393 | NM_00200 | <u>farnesyl diphosphate synthase (farnesyl pyrophosphate synthetase, dimethylally-transtransferase, geranyltranstransferase</u> |
| P | D | 0.659754 | Hs.132898 | NM_00593 | fatty acid desaturase 1 |
| P | D | 0.659754 | Hs.274398 | BC002654 | *Homo sapiens*, similar to tubulin, beta4, clone MGC: 4083, mRNA, complete cds |
| P | D | 0.659754 | | BC005838 | *Homo sapiens*, tubulin, beta5 |
| P | D | 0.659754 | Hs.115285 | BF978872 | dihydrolipoamide S-acetyltransferase (E2 component of pyruvate dehydrogenase complex) |
| P | D | 0.659754 | Hs.159154 | AL565749 | Tubulin, beta 4 |
| P | D | 0.659754 | Hs.179817 | AF167438 | *Homo sapiens* androgen-regulated short-chain dehydrogenasereductase 1 (ARSDR1) |
| P | D | 0.615572 | Hs.213289 | NM_00052 | <u>low density lipoprotein receptor (familial hypercholesterolemia)/FL = gb: NM_000527.2</u> |
| P | D | 0.615572 | Hs.75105 | NM_00657 | emopamil-binding protein (sterol isomerase) /FL = gb: NM_006579.1 |
| P | D | 0.615572 | Hs.74304 | NM_00270 | *Homo sapiens* periplakin (PPL) |
| A | D | 0.615572 | Hs.268515 | NM_00243 | meningioma (disrupted in balanced translocation) 1/FL = gb: D63807.1 |
| P | D | 0.615572 | UG = Hs.31 | AF096304 | *Homo sapiens* putative sterol reductanse SR-1 (TM7SF2) transmembrane 7 super family 2/FL = gb: AF096304.1 |
| P | D | 0.615572 | Hs.93199 | D63807.1 | lanosterol synthase (2,3-oxidosqualene-lanosterol cyclase)/FL = gb: D63807.1 |
| P | D | 0.574349 | Hs.119597 | AB032261 | <u>stearoyl-CoA desaturase (delta-9-desaturase)/FL = gb: AF097514.1 gb: NM_005063 gbL/ab932261.1</u> |
| P | D | 0.574349 | Hs.174140 | AI971281 | <u>ATP citrate lyase/FL = gb: NM_001096.1</u> |
| P | D | 0.574349 | Hs.171825 | NM_00367 | basic heliz-loop-helix domain containing, class B, 2/FL = gb: AB004066.1 gb: NM_003670.1 |
| P | D | 0.574349 | Hs.79103 | AW235051 | cytochrome b5 outer mitochondrial membrane precursor /FL = gb: BC004373.1 gb: NM_030579.1 |
| P | D | 0.574349 | Hs.11806 | NM_00136 | dehydrocholesterol reductase /FL = gb: BC000054.1 gb: AF034544.1 gb: AF067127.1 gb: AF096305 gb: NM_001360.1 |
| P | D | 0.574349 | Hs.3838 | NM_00662 | serum-inducible kinase/FL = gb: AF059617.1 gb: NM_006622.1 gb: AF223574.1 |
| P | D | 0.574349 | Hs.213289 | AI861942 | <u>low density lipoprotein receptor (familial hypercholesterolemia)/FL = gb: NM_000527.2</u> |
| P | D | 0.574349 | Hs.92199 | AW084510 | lanosterol synthase (2,3-oxidosqualene-lanosterol cyclase)/FL = gb: NM_002340.1 gb: NM_U22526.1 |
| P | D | 0.574349 | Hs.5920 | NM_00547 | UDP-N-acetylglucosamine-2-epimerase-N-acetylmannosamine kinase |
| P | D | 0.574349 | Hs.1524 | NM_00381 | tumor necrosis factor (ligand) superfamily, member9/FL = gb: NM_003811.1 gb: U03308.1 |
| P | D | 0.574349 | Hs.278544 | BC000408 | acetyl-Coenzyme A acetyltransferase 2 (acetoacetyl Coenzyme A thiolase) /FL = gb: BC000408.1 |
| P | D | 0.574349 | Hs.174140 | U18197.1 | <u>ATP citrate lyase /FL = gb: U18197.1</u> |
| P | D | 0.574349 | Hs.7232 | B3855983 | <u>acetyl-Coenzyme A carboxylase alpha /FL = gb: NM_000664.1 gb: U19822.1</u> |
| P | D | 0.535887 | Hs.226213 | NM_00078 | cytochrome P450, 51 (lanosterol 14-alpha-demthylase) /FL = gb: U23042.1 gb: NM_000786 gb: D55653.1 |
| A | D | 0.535887 | Hs.268490 | NM_00047 | nuclear receptor subfamily O, group B, member 1/FL = gb: NM_000475.2 |

TABLE 5-continued

| | | | | | |
|---|---|---|---|---|---|
| P | D | 0.535887 | Hs.48876 | :AA872727 | farnesyl-diphosphate farnesyltransferase /FL = gb: L06070.1 gb: L06105.1 gb: NM_004462.1 |
| P | D | 0.535887 | Hs.65270 | NM_00603 | lipase, endothelial/FL = gb: AF118767.1 gb: NM_006033.1 |
| | | 0.535887 | Hs.14779 | AK000162 | acetyl-CoA synthetase |
| | | 0.535887 | Hs.44499 | U59479.1 | pinin, desmosome associated protein/DEF = Human neutrophil protein mRNA, partial cds |
| P | D | 0.5 | Hs.154654 | AU144855 | cytochrome P450, subfamily I (dioxin-inducible), polypeptide 1 (glaucoma 3, primary infantile) |
| P | D | 0.5 | Hs.11899 | AL518627 | 3-hydroxy-3-methylglutaryl-Coenzyme A reductase/FL = gb: M11058.1 gb: NM_000859.1 |
| | | 0.5 | Hs.2178 | NM_00352 | H2B histone family, member Q/FL = gb: NM_003528.1 |
| P | D | 0.5 | Hs.130607 | NM_00043 | mevalonate kinase (mevalonic aciduria) /FL = gb: M88468.1 gbz: NM_000431.1 |
| P | D | 0.5 | Hs.284244 | NM_00200 | fibroblast growth factor 2 (basic) /FL = gb: M27968.1gb: NM_002006.1 |
| P | D | 0.5 | Hs.71465 | AF098865 | squalene epoxidase/FL = gb: D78130.1 gb: AF098865.1 gb: NM_003129.2 |
| P | D | 0.5 | Hs.288031 | D85181.1 | sterol-C5-desaturase (fungal ERG3, delta-5-desaturase)-like/FL = gb: D85181.1 |
| A | D | 0.5 | | L32662.1 | prostaglandin E2 receptor/DB_XREF = gi: 484163/FL = gb: L32662.1 |
| P | D | 0.5 | Hs.81412 | D80010.1 | lipin 1 |
| P | D | 0.466517 | Hs.11899 | NM_00085 | 3-hydroxy-3-methylglutaryl-Coenzyme A reductase/FL = gb: M11058.1 gb: NM_000859.1 |
| P | D | 0.466517 | Hs.79440 | NM_00654 | IGF-II mRNA-binding protein 3/FL = gb: U07188.1 gb: U76705.1 gb: AF117108.1 gb: NM_006547.1 |
| P | D | 0.466517 | Hs.75318 | AL575074 | tubulin, alpha 1 (testis specific) |
| P | D | 0.466517 | Hs.226213 | U40053 | cytochrome P450, 51 (lanosterol 14-alpha-demethylase) |
| P | D | 0.466517 | Hs.187579 | NM_01637 | hydroxysteroid (17-beta) dehydrogenase 7 /FL = gb: AF098786.2 gb: NM_016371.1 |
| P | D | 0.466517 | Hs.76038 | BC005247 | isopentenyl-diphosphate delta isomerase /FL = gb: BC005247.1 |
| P | D | 0.466517 | Hs.57698 | BC000245 | NAD(P) dependent steroid dehydrogenase-like; H105e3/FL = gb: BC000245.1 gb: U4710 gb: NM_015922.1 |
| P | D | 0.353553 | Hs.77910 | NM_00213 | 3-hydroxy-3-methylglutaryl-Coenzyme a synthase 1 (soluble) /FL = gb: BC000297.1 gb: L25798.1 gb: NM_015922.1 |
| P | D | 0.329877 | Hs.56205 | BE300521 | insulin induced gene 1/FL = gb: NM_005542.1 |
| P | D | 0.329877 | Hs.154654 | NM_00010 | cytochrome P450, subfamily I (dioxin-inducible), polypeptide 1 (glaucoma3, primary infantile) /FL = gb: NM_000104.2 gb: U0 |
| P | D | 0.329877 | Hs.3828 | AI189359 | mevalonate (diphospho) decarboxylase /FL = gb: U49260.1 gb: CB000011.1 gb: NM_002461.1 |

Figure 18A:
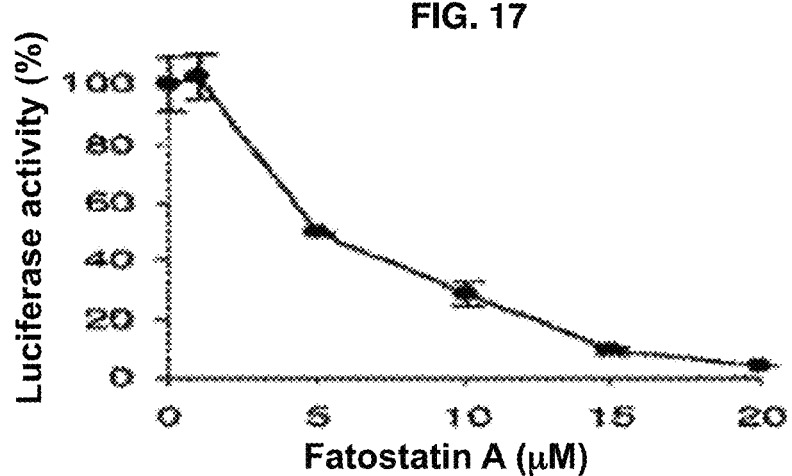
FIGS. 18A-18D show that fatostatin blocks the activation of SREBP. Suppression by fatostatin of the ability of endogenous SREBPs to activate a luciferase reporter gene in a medium containing lipid-free serum. CHO-K1 cells were transfected with an SRE-1-driven luciferase reporter (pSRE-Luc) (FIG. 18A). The transfected cells were treated by varied concentrations of fatostatin in a medium containing lipid-free serum. Effect of fatostatin on CHO-K1 cells co-transfected with pCMV-SREBP-1c(1-436) and pSRE-Luc in a medium containing lipid-free serum (FIG. 18B). PLAP-BP2 in transfected CHO-K1 cells remains membrane-bound unless it is cleaved by S1P in the Golgi and secreted into the culture medium (left). Treatment with fatostatin (20 µM) or sterols (10 µg/mL cholesterol and 1 µg/mL 25-hydroxycholesterol) affect cleavage of PLAP-BP2 compared to EtOH controls (FIG. 18C). Western blot analysis of CHO-K1 cells treated with fatostatin. P and N denote the uncleaved membrane precursor and cleaved nuclear forms of SREBP-2, respectively (FIG. 18D).
Figure 18B:
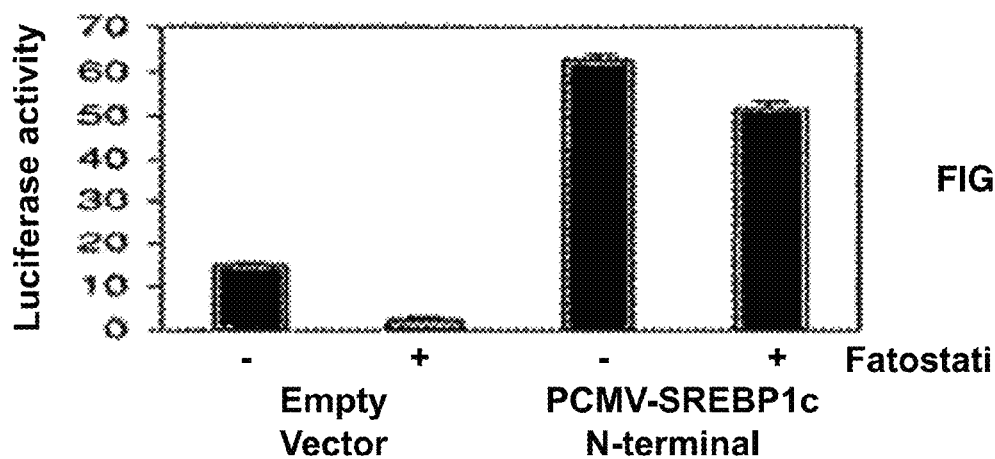

To confirm that fatostatin impairs the function of SREBPs, the ability of endogenous SREBPs to activate transcription of an SREBP-responsive reporter gene was measured in CHO-K1 cells in the presence or absence of fatostatin (FIG. 18A). Fatostatin decreased activation of the reporter gene, in which the expression of luciferase is controlled by sterol regulatory elements. Fatostatin had limited effect on the ability of an exogenously expressed, mature form of SREBP-1 (amino acids 1-436) to activate the reporter gene (FIG. 18B), indicating that fatostatin impairs the activation process of SREBPs.

Figure 18C:
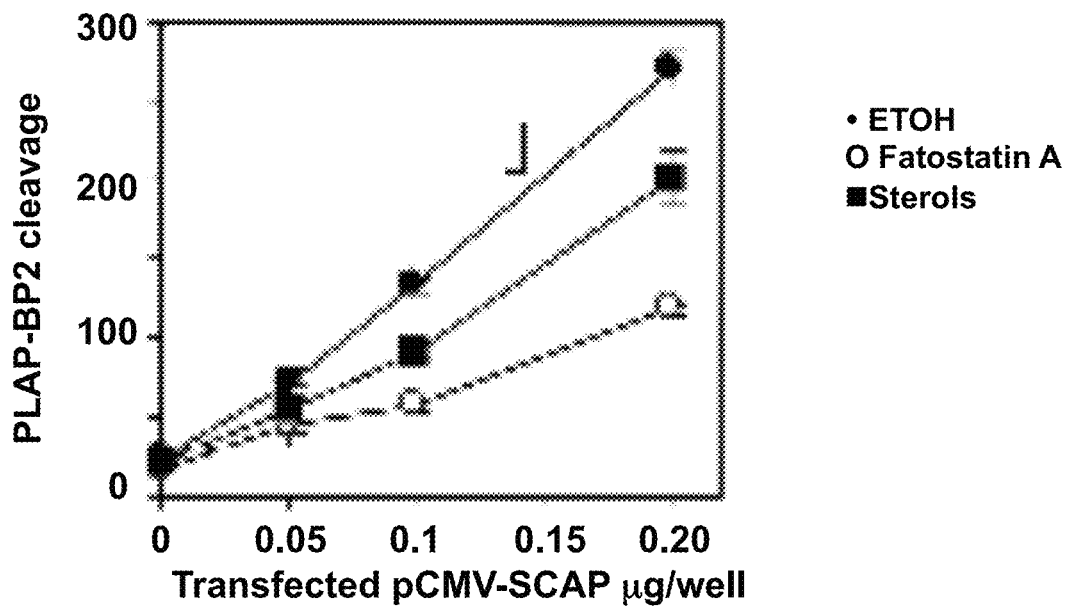
Figure 18D:
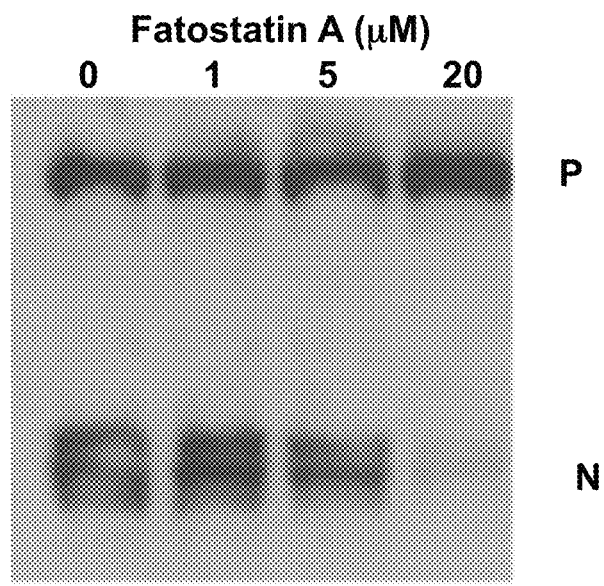
Figure 22:
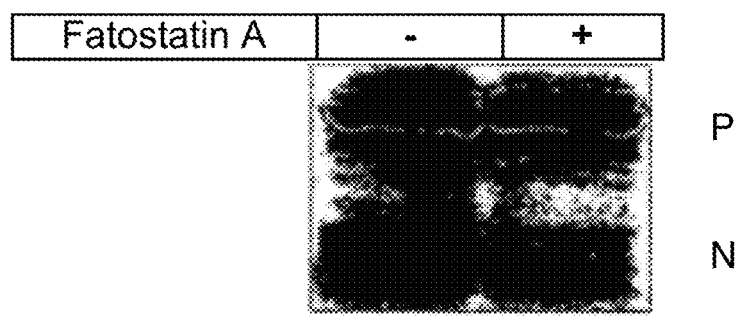
FIG. 22 demonstrates a western blot analysis of CHO-K1 cells treated with fatostatin. P and N denote the uncleaved membrane precursor and cleaved nuclear forms of SREBP-1, respectively.

To determine if fatostatin affects the ER-Golgi translocation and proteolytic processing of SREBPs, a reporter assay developed by Sakai et al. (1998) was used. PLAP-BP2 in transfected CHO-K1 cells remains membrane-bound unless it is cleaved by S1P in the Golgi and secreted into the culture medium. In the assay, a secreted alkaline phosphatase, fused with an SREBP-2 fragment lacking the NH2-terminal DNA-binding domain (PLAP-BP2513-1141), permits monitoring of translocation and processing through changes in the fluorescence of a fluorogenic phosphatase substrate (FIG. 18C). When cells were co-transfected with plasmids encoding PLAP-BP2513-1141 and SCAP, PLAP phosphatase was secreted, generating fluorescence signals. Secretion was similarly decreased by the addition of fatostatin or sterols (FIG. 18C). The fatostatin-mediated inhibition of SREBP activation was confirmed by western blot analysis of SREBPs. Treatment of the CHO-K1 cells with fatostatin decreased the amount of the 68 KDa mature form of SREBP-2, and increased the amount of the 125 KDa precursor form (FIG. 18D). Similar results were obtained for SREBP-1 (FIG. 22). These results collectively indicate that fatostatin blocks the activation process of both isoforms of SREBP.

Figure 19A:
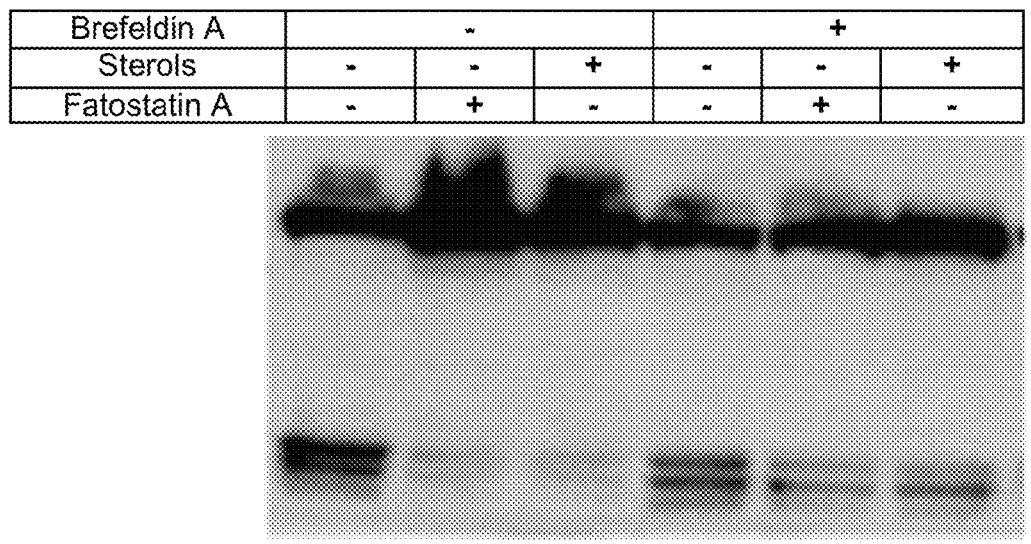
FIGS. 19A-19B show that fatostatin blocks the translocation of SREBPs from the ER to the Golgi.

The inventors considered that fatostatin impairs either the proteolytic cleavage of SREBPs in the Golgi apparatus or the ER-to-Golgi translocation of the SCAP/SREBP complex. Brefeldin A, a natural product that blocks anterograde movement of proteins from the ER to the Golgi, is known to render SREBPs unresponsive to sterols, and causes SREBPs to be constitutively processed in the ER by relocating S1P from the Golgi to the ER (DeBose-Boyd et al., 1999). In the presence of brefeldin A, fatostatin had no impact on the SREBP processing (FIG. 19A), suggesting that fatostatin does not block the proteolysis itself.

Figure 19B:
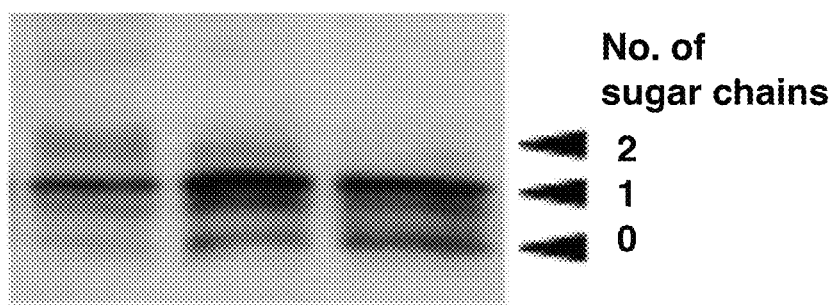

To determine whether fatostatin blocks the ER-to-Golgi translocation of the SCAP/SREBP complex, the inventors analyzed the extent of N-linked glycosylation of SCAP in the Golgi apparatus. SCAP contains a glycosylated luminal loop that is protected from proteolysis by trypsin and recognizes anti-SCAP IgG-9D5. The two oligosaccharides in the loop are sensitive to endoglycosidase H when SCAP resides in the ER. As SCAP is transported to the Golgi, its sugars become resistant to digestion by endoglycosidase H. The translocated SCAP has higher levels of glycosylation, and is more resistant to endoglycosidase H than ER-bound SCAP. Sterols prevent SCAP from becoming resistant to endoglycosidase H by inhibiting the ER-Golgi translocation (Nohturfft et al., 1998). Cells were grown in the absence or presence of fatostatin or sterols, and membrane fractions were treated successively with trypsin and endoglycosidase H. In cells grown without fatostatin and sterols, a tryptic fragment of SCAP was more resistant to endoglycosidase H and had one or two saccharide chains (FIG. 19B, lane 1). When cells were grown in the presence of fatostatin or sterols, the SCAP fragment was less resistant to endoglycosidase H, and had either zero or one saccharide chain (FIG. 19B, lanes 2 and 3). Thus fatostatin appears to inhibit the translocation of SCAP from the ER to the Golgi.

Figure 20B:
Figure 20C:
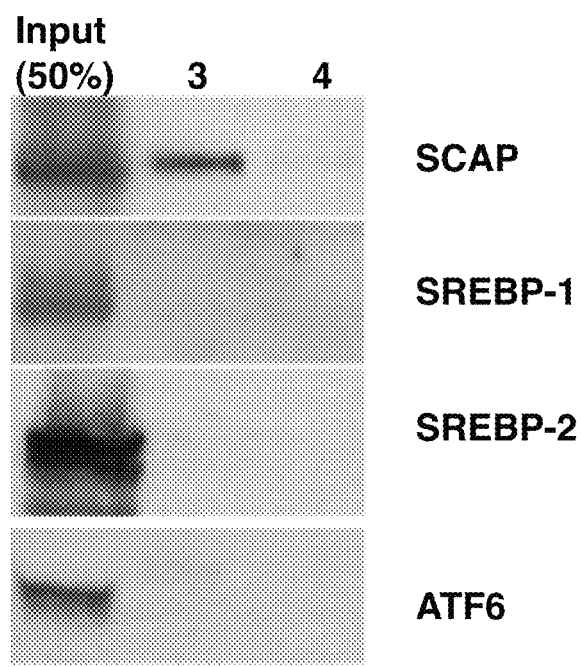
Figure 20D:
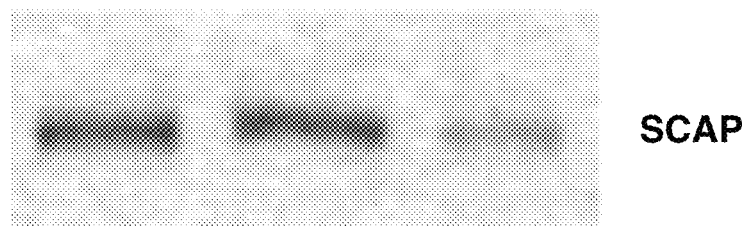
Figure 24:
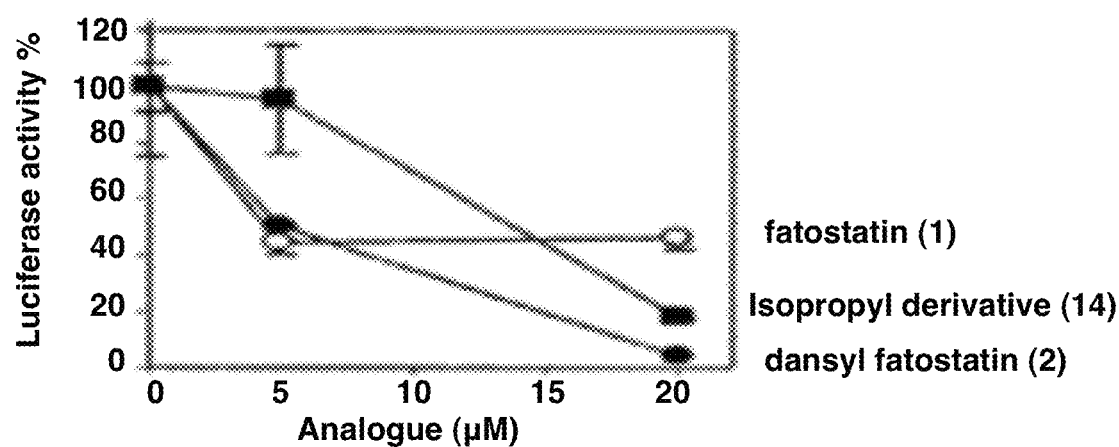
FIG. 24 shows suppression by fatostatin analogues of the ability of endogenous SREBPs to activate a luciferase reporter gene in a medium containing lipid-free serum. CHO-K1 cells were transfected with pSRE-Luc. The transfected cells were treated by varied concentrations of fatostatin, dansyl fatostatin or isopropylamine derivative in a medium containing lipid-free serum.

Studies of the structure-activity relationship of fatostatin indicated that the molecule retains or even increases biological activity when its toluene moiety is modified with a variety of alkyl or aryl sulfonamide groups. One fluorescent derivative, dansyl fatostatin (FIG. 20A), retained the ability to block SREBP activation (FIG. 24) and served as a microscopic probe. Confocal microscopic analyses revealed that the localization of dansyl fatostatin overlapped with that of ER-tracker red, a specific marker for ER (FIG. 20B). In contrast, the control dansyl molecule, which lacked fatostatin, failed to localize to any organelle. The selective ER localization implies that fatostatin binds to a protein in the ER; the most likely candidate is SCAP, the target of cholesterol for the control of SREBP (Radhakrishnan et al., 2004). To test this hypothesis, proteins bound to a fatostatin-polyproline linker-biotin conjugate (FIG. 20A) (Sato et al., 2007) were purified from cell lysates and analyzed by western blots with antibodies against SCAP, SREBP-1, SREBP-2, and ATF6, an unrelated ER-bound transcription factor (Ye et al., 2000). The results showed that fatostatin was bound to SCAP, but not to the other proteins (FIG. 20C). The binding was lost upon addition of excess fatostatin, but not excess cholesterol (FIG. 20D), raising the possibility that fatostatin may interact with SCAP at a site distinct from that of cholesterol.

Having established a key role of SREBPs in lipogenesis, the pharmacological effects of fatostatin on ob/ob mice, a mouse model of obesity with uncontrolled food intake, was then examined. Fatostatin was delivered intraperitoneally on a daily basis, and food intake and body weight were monitored. The average daily food intake by the treated mice was not significantly different from that of the controls (5.4+1.5 vs. 5.9+1.4 g/mouse/d, respectively, p>0.05), and no obvious toxicity was observed during the treatment. After 28 days of treatment with fatostatin, the treated mice weighed about 12% less than the untreated controls (32.1±1.4 and 36.22 g/mouse, respectively, p=0.02). One of the most distinct phenotypes in ob/ob mice is hyperglycemia resulting from insulin resistance. Examination of blood constituents revealed that the average glucose level of the treated mice was ~70% lower than that of the untreated mice (153.2±30.5 vs. 429.4±87 mg/dl, respectively, p=0.003), which is in the range of normal glucose levels. These results are consistent with the reported role of SREBP-1c in the pathogenesis of hepatic insulin resistance Ode et al., 2004).

Figure 21:
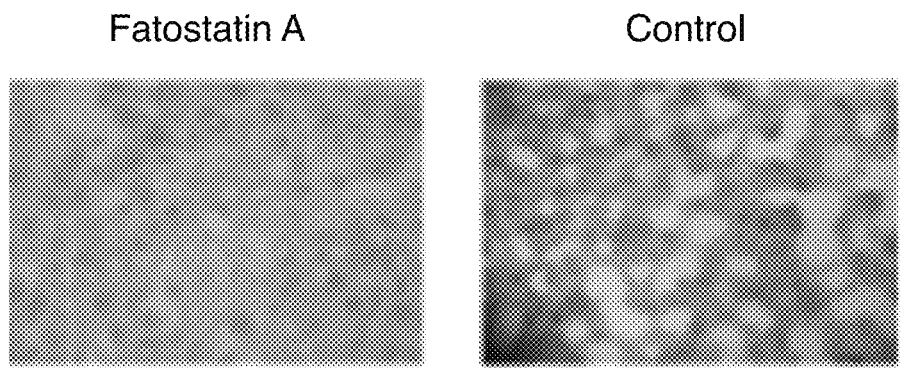
FIG. 21 show effects of fatostatin on liver and adipose tissue of ob/ob mice. Sections of the livers of fatostatin-treated and control mice showing red-stained lipid droplets.

Another phenotype of ob/ob mice is excessive accumulation of fat in organs, including non-alcoholic fatty liver. Enlarged and fatty livers were evident from their pale color in the untreated ob/ob mice, while livers of the mice treated with fatostatin appeared normal. Livers of the treated mice averaged ~32% less weight, and fat pads were smaller than those of the untreated mice. Oil red staining of the liver sections showed that the livers of the untreated ob/ob mice contained abundant lipid droplets, while livers of the treated mice contain lower levels of lipid accumulation (FIG. 21). The triglyceride and cholesterol levels in the livers of the treated mice were also reduced. The prevention of fatty liver in ob/ob mice by fatostatin is in agreement with the reported role of SREBP-1 in developing fatty liver: transgenic mice overexpressing SREBP-1 developed fatty livers (Horton et al., 2003), while ob/ob mice lacking SREBP-1 (lep$^{ob/ob}$×Srebp 1$^{-/-}$) had healthy livers (Yahagi et al., 2002).

The reduction of hepatic fat levels in the treated mice was thought to be due to decreased hepatic expression of SREBP-responsive lipogenic enzymes. Therefore, the effects of fatostatin were examined on the hepatic protein levels and enzymatic activities of representative SREBP-responsive lipogenic enzymes, including fatty acid synthase (FAS), acetyl-CoA carboxylase, stearoyl-CoA desaturase 1 (SCD1), and ATP citrate lyase (ACL). Biochemical analysis showed that protein levels and activities of the lipogenic enzymes were reduced in liver extracts of fatostatin-treated mice (FIGS. 25A-25C). Thus, fatostatin blocks the processing of SREBP-1 in liver, downregulates lipogenic enzymes, and reduces hepatic triglyceride storage. Fatostatin represents the first non-sterol-like synthetic molecule that inhibits the activation of SREBPs.

Luciferase reporter assay. On day 0, CHO-K1 cells were plated out onto a 96-well plate in medium A (a 1:1 mixture of Ham's F-12 medium and Dulbecco's modified Eagle's medium, with 5% fetal bovine serum, 100 units/mL penicillin, and 100 µg/mL streptomycin sulfate). On day 2, the cells were transiently co-transfected with pSRE-Luc (an SRE-1-driven luciferase reporter construct) (Hua et al., 1995) and pAc-β-gal (β-gal reporter in which the expression of β-gal is controlled by an actin promoter), using Lipofectamine reagent (Invitrogen). After incubation for 5 h, the cells were washed with phosphate-buffered saline (PBS), and then incubated, in the absence or presence of fatostatin, in medium B (a 1:1 mixture of Ham's F-12 medium and Dulbecco's modified Eagle's medium, with 5% lipid-depleted serum, 100 units/mL penicillin, 100 µg/mL streptomycin sulfate, 50 mM compactin, and 50 mM sodium mevalonate). After 20 h of incubation, the cells in each well were lysed, and aliquots were used to measure luciferase and β-galactosidase activities. Luciferase activity was normalized by the activity of β-galactosidase. For overexpression of the N-terminal matured form of SREBP-1c, pCMV-SREBP-1c(1-436) was co-transfected with pSRE-Luc and pAc-β-gal.

Western blot analysis of SREBP processing. On day 0, CHO-K1 cells were plated out onto a 100 mm dish of medium A. On day 2, the cells were washed with PBS, and then incubated in medium B in the absence or presence of fatostatin. On day 3, the cells were washed once with cold PBS, and then treated with buffer containing 10 mM Tris-HCl, pH 7.6, 100 mM NaCl, 1% (w/v) SDS, and protease inhibitor mixture (1 µg/ml pepstatin A, 10 µg/ml leupeptin, 200 µM phenylmethylsulfonyl fluoride). The protein concentration of each total cell extract was measured (BCA kit; Pierce), after which a 22-33 µg aliquot of cell extract was mixed with 0.25 volume of buffer (250 mM Tris-HCl, pH 6.8, 10% SDS, 25% glycerol, 0.2% (w/v) bromophenol blue, and 5% (v/v) 2-mercaptoethanol), heated for 7 min at 95° C. The samples were separated on a 10% SDS-PAGE gel and blotted using mouse monoclonal antibody against SREBP-2 (IgG-7D4) (Yang et al., 1995). The specific bands were visualized using enhanced chemiluminescent (ECL) detection reagents (Amersham).

Modification of SCAP oligosaccharides. Cell membrane fractions were prepared as described elsewhere herein. The membrane pellets were resuspended in 0.1 mL of buffer containing 10 mM Hepes•KOH (pH 7.4), 10 mM KCl, 1.5 mM MgCl$_2$, 1 mM sodium EDTA, and 100 mM NaCl. Aliquots of protein were then incubated in the absence or presence of 1 µg of trypsin, in a total volume of 58 µL, for 30 min at 30° C. Reactions were stopped by addition of 2 µL (400 units) of soybean trypsin inhibitor. For subsequent treatment with endoglycosidase H, individual samples received 10 µl of solution containing 3.5% (wt/vol) SDS and 7% (vol/vol) 2-mercaptoethanol. After heating at 100° C. for 10 min, each sample received sequential additions of 9 µl of 0.5 M sodium citrate (pH 5.5), 5 µL of solution containing 17' protease inhibitors (a concentration of 1×, corresponding to 10 µg/mL leupeptin, 5 µg/mL pepstatin A, and 2 µg/mL aprotinin), followed by 1 µL (5 units) of endoglycosidase H. The reactions were carried out overnight at 37° C. and stopped by the addition of 20 µL of buffer containing 0.25 M Tris•HCl (pH 6.8), 2% SDS, 10% (vol/vol) glycerol, 0.05% (wt/vol) bromophenol blue, and 4% 2-mercaptoethanol. The mixtures then were heated at 100° C. for 5 min and subjected to SDS/PAGE (12% gels).

Confocal microscopic analyses. CHO-K1 cells on a glass-bottom 96-well plate (Grainer) at ~70% confluency were incubated with 0.2 µM ER-tracker Red (Invitrogen) and 5 mM dansyl fatostatin for 1 h. Fluorescent images were captured and analyzed with a Carl Zeiss LSM 510 confocal microscope, equipped with a CSU10 spinning-disk confocal scanner (Yokogawa Electric Corporation) and an ORCA-CCD camera (Hamamatsu Photonics). Images were analyzed with IPLab software (Solution Systems).

Binding assay. Cell membrane fractions were prepared as described in Supplementary Methods. The membrane fraction was extracted with PBS containing 0.1% FOS-Choline 10 (Hampton Research). The extract was mixed with Neutravidine-agarose beads (10 µL) saturated with biotinylated fatostatin and incubated for 1 h. The bound proteins were washed four times with PBS containing 0.1% FOS-Choline 10, boiled in 25 µL of SDS sample buffer, and subjected to western blotting. For the competition assay, saturated amounts of cholesterol or fatostatin were added to the membrane extract before incubating with the beads.

Animal studies procedures. Four to five week-old homozygous male obese (ob/ob) mice (C57BL/6J, The Jackson Laboratory, Bar Harbor, Me.) were housed under controlled conditions (12 h light/dark cycle; 25° C.). The animals were housed 5 per cage, and had ad libitum access to standard laboratory chow (Purina Mills, Richmond, Ind.) and water for one week after their arrival. On first day of the experiment and every day thereafter, the weight of each mouse and the amount of food intake were measured between 3:00 and 5:00 p.m. Following weight measurements, treated mice received an ip injection of fatostatin (30 mg/kg; 150 µL), and control mice received 10% DMSO in PBS. Daily Injections were continued for four weeks, until the end of the study.

Blood constituents. After 28 days of daily injection of fatostatin mice were fasted for 5-6 h, whole blood glucose and 3-hydroxybutyrate were measured with a Glucometer Precision Xtra (Abbott). Measurements of the serum constituents, glucose, triglyceride, and cholesterol, were performed by the Comparative Pathology Laboratory (Baylor College of Medicine). Serum non-esterified fatty acids (NEFA) were measured using a NEFA C kit (Wako Chemicals, Richmond, Va.).

Liver analyses. Mice were sacrificed, and weights of livers and epididymal fat pads were determined. Frozen sections of liver slices from individual animals were stained with Oil Red O to visualize the fat droplets (triglycerides) in liver slices, as described (Abu-Elheiga et al., 2001). The remaining liver tissues were frozen in liquid nitrogen and kept at −80° C. for further analysis.

Tissue triglyceride and cholesterol contents. Liver triglyceride and cholesterol contents were determined as described by Chandler et al. (2003), using a Cholesterol E Kit (Wako) and an Infinity Triglyceride Kit (Thermo Electron, Melbourne, Australia).

Figure 23:
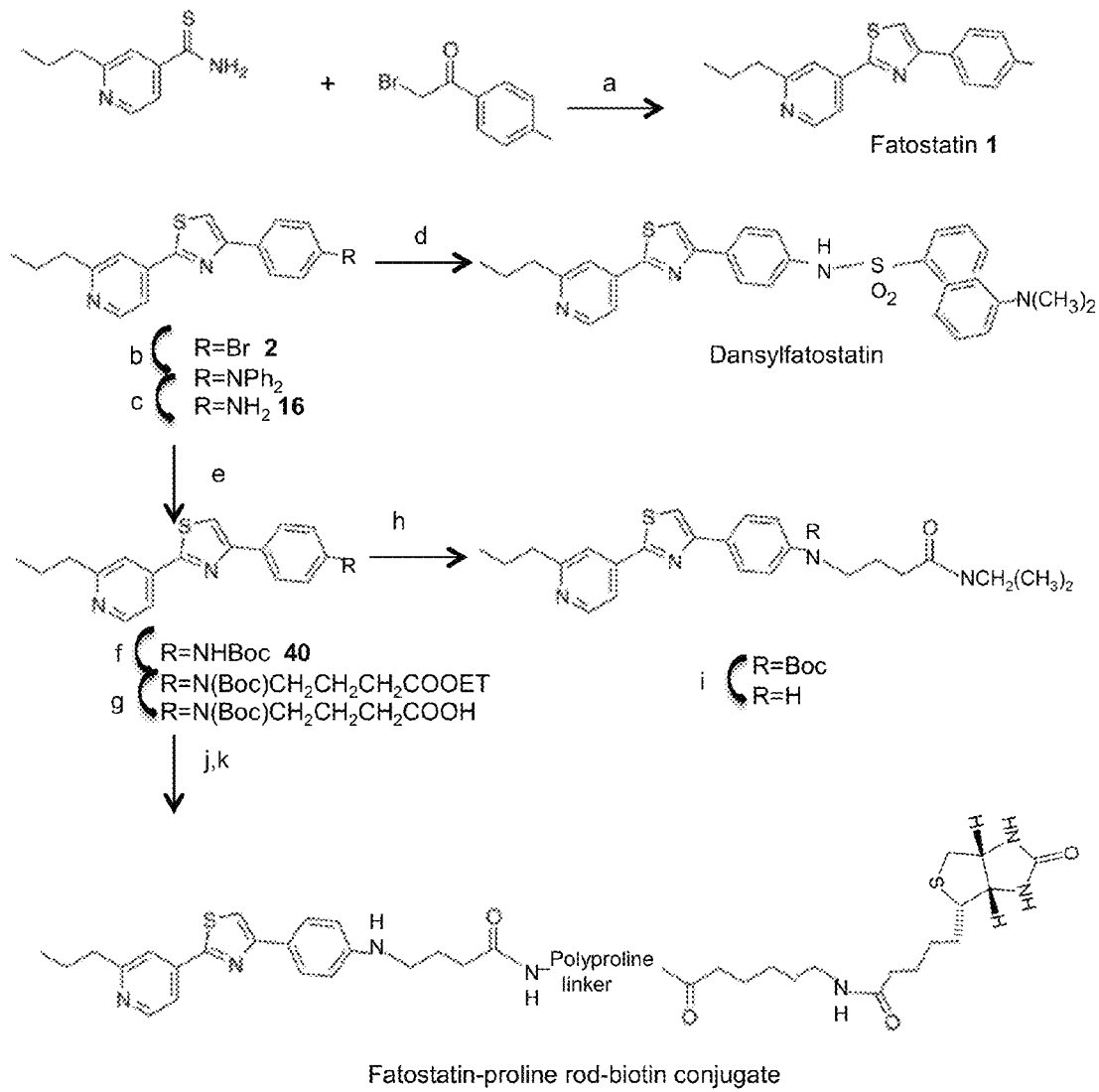
FIG. 23 provides an exemplary synthetic scheme of fatostatin, dansyl fatostatin and fatostatin-polyproline linker-biotin.

Synthesis of Fatostatin 1, Dansyl Fatostatin and Fatostatin-Polyproline Linker-Biotin Conjugate FIG. 23 depicts the synthesis of fatostatin 1, dansyl fatostatin, fatostatin-polyproline linker-biotin conjugates and the synthetic intermediates.

Synthesis of Fatostatin 1

A mixture of prothionamide (1.03 g, 5.70 mmol) and 2-bromo-4'-methylacetophenone (1.22 g, 5.70 mmol) in ethanol (20 ml) was heated at 70° C. with stirring for 0.5 h, and then cooled to 0° C. A yellow precipitate formed was filtered, washed with cold ethanol, and dried to give 2-propyl-4-(4-p-tolylthiazol-2-yl)pyridine (fatostatin) 1 HBr salt (1.78 g, 83%) as yellow needles. mp: 190-193° C.; $^1$H NMR (600 MHz, DMSO-d$_6$): δ 8.88 (d, J=6.2 Hz, 1H), 8.54 (s, 1H), 8.46 (d, J=1.4 Hz, 1H), 8.36 (dd, J=1.4, 6.2 Hz, 1H), 7.99 (d, J=7.6 Hz, 2H), 7.31 (d, J=7.6 Hz, 2H), 3.03 (t, J=7.6 Hz, 2H), 2.35 (s, 3H), 1.80 (m, 2H), 0.96 (t, J=7.6 Hz, 3H); $^{13}$C NMR (150 MHz, DMSO-d$_6$): δ 161.3, 158.5, 156.9, 146.2, 143.2, 138.4, 130.4, 129.5, 126.3, 122.3, 120.3, 119.5, 35.0, 22.4, 20.9, 13.4; HRMS (m/z): [M+H]$^+$ calcd for C$_{18}$H$_{19}$N$_2$S, 295.1269. found, 295.1269.

Synthesis of 4-(2-(2-propylpyridin-4-yl)thiazol-4-yl)benzenamine 16

A pressure tube was charged with 2 (1.08 g, 3.0 mmol), benzophenone imine (0.57 g, 3.3 mmol), Pd$_2$(dba)$_3$ (86 mg, 0.15 mmol), BINAP (280 mg, 0.45 mmol), sodium tert-butoxide (1.44 g, 9.0 mmol), and dry toluene (30 mL) and purged with argon gas. The pressure tube was sealed and heated in a 100° C. bath for 20 h. After being cooled to room temperature, the reaction mixture was chromatographed (SiO$_2$, 4:1 hexane:EtOAc) to provide 1.35 g of 8 (98%) as a yellow oil. Then to a solution of 8 (1.35 g, 2.9 mmol) in THF (20 mL) was added 2 N aqueous HCl solution (15 mL). After being stirred at room temperature for 2 h, the reaction mixture was concentrated under reduced pressure, then diluted with EtOAc (100 mL) and washed with saturated Na$_2$CO$_3$ (50 mL) solution. The aqueous wash was extracted with EtOAc (3×40 mL), and the combined EtOAc layers were dried over Na$_2$SO$_4$ and concentrated. The crude product was chromatographed (SiO$_2$, 4:1 hexane:EtOAc) to provide 0.73 g of 4-(2-(2-propylpyridin-4-yl)thiazol-4-yl)benzenamine 16 (82%) as a white crystal. $^1$H NMR (600 MHz, CDCl$_3$): δ 8.61 (d, J=4.8 Hz, 1H), 7.80 (d, J=8.9 Hz, 2H), 7.75 (d, J=1.4 Hz, 1H), 7.67 (dd, J=1.4, 4.8 Hz, 1H), 7.36 (s, 1H), 6.75 (d, J=8.9 Hz, 2H), 3.82 (brs, 1H), 2.85 (t, J=7.6 Hz, 2H), 1.83 (m, 2H), 1.01 (t, J=7.6 Hz, 3H); $^{13}$C NMR (150 MHz, CDCl$_3$): δ 164.9, 163.4, 157.3, 150.0, 146.8, 140.8, 127.7, 124.8, 119.2, 117.8, 115.1, 111.3, 40.4, 23.1, 13.9; HRMS (m/z): [M+H]$^+$ calcd for C$_{17}$H$_{18}$N$_3$S, 296.1221. found, 296.1228.

Synthesis of Dansyl Fatostatin

To a magnetically stirred solution of 16 (50 mg, 0.17 mmol) and pyridine (27 mg, 0.34 mmol) in CH$_2$Cl$_2$ (5 mL) was added dansyl chloride (50 mg, 0.18 mmol). After being stirred for 17 h, the reaction mixture was concentrated under reduced pressure, and the residue was partitioned between EtOAc (50 mL) and saturated NH4Cl solution (20 mL). The aqueous phase was extracted with EtOAc (2×20 mL). The combined extracts were washed with saturated $NaHCO_3$ solution, dried over $Na_2SO_4$, and concentrated. The crude product was chromatographed ($SiO_2$, 2:1 hexane:EtOAc) to afford dansylfatostatin (65 mg, 73%) as a yellow crystal. $^1$H NMR (600 MHz, $CDCl_3$): δ 8.60 (d, J=4.8 Hz, 1H), 8.50 (d, J=8.2 Hz, 1H), 8.36 (d, J=8.3 Hz, 1H), 8.21 (d, J=8.3 Hz, 1H), 7.76 (d, J=8.6 Hz, 2H), 7.70 (d, J=1.5 Hz, 1H), 7.62 (dd, J=1.5, 4.8 Hz, 1H), 7.61 (t, J=8.3 Hz, 1H) 7.44 (s, 1H), 7.43 (dd, J=7.5, 8.2 Hz, 1H), 7.19 (d, J=7.5 Hz, 1H), 7.04 (d, J=8.6 Hz, 2H), 6.97 (brs, 1H), 2.87 (s, 6H), 2.84 (t, J=7.6 Hz, 2H), 1.81 (m, 2H), 1.00 (t, J=7.6 Hz, 3H); $^{13}$C NMR (150 MHz, $CDCl_3$): δ 165.5, 163.5, 156.1, 152.2, 150.0, 140.5, 136.7, 134.0, 131.1, 131.0, 130.5, 129.8, 129.7, 128.7, 127.3, 123.1, 121.6, 119.2, 118.3, 117.8, 115.3, 113.8, 45.4, 40.4, 23.1, 13.9; HRMS (m/z): [M+H]$^+$ calcd for $C_{29}H_{29}N_4O_2S_2$, 529.1732. found, 529.1733.

Synthesis of tert-butyl 4-(2-(2-propylpyridin-4-yl) thiazol-4-yl)phenylcarbamate 40

To a magnetically stirred solution of 16 (0.57 g, 1.92 mmol) and 4-(dimethylamino)pyridine (5 mg, 0.4 mmol) in THF (20 mL) was added di(tert-butyl)dicarbonate (0.49 g, 2.21 mmol). After being stirred for 17 h, the reaction mixture was concentrated under reduced pressure, and the residue was partitioned between EtOAc (100 mL) and saturated $NH_4Cl$ solution (30 mL). The aqueous phase was extracted with EtOAc (2×50 mL). The combined extracts were washed with saturated $NaHCO_3$ solution, dried over $Na_2SO_4$, and concentrated. The crude product was chromatographed ($SiO_2$, 2:1 hexane:EtOAc) to afford tert-butyl 4-(2-(2-propylpyridin-4-yl)thiazol-4-yl)phenylcarbamate 40 (0.33 g, 43%) as a yellow foam. $^1$H NMR (300 MHz, $CDCl_3$): δ 8.68 (d, J=5.1 Hz, 1H), 7.93 (d, J=8.4 Hz, 2H), 7.79 (s, 1H), 7.72 (d, J=5.1 Hz, 1H), 7.52 (s, 1H), 7.47 (d, J=8.4 Hz, 2H), 6.58 (s, 1H), 2.90 (t, J=7.5 Hz, 2H,), 1.87 (m, 2H), 1.55 (s, 9H), 1.03 (t, J=7.5 Hz, 3H); $^{13}$C NMR (75 MHz, $CDCl_3$): δ 163.1, 156.5, 152.3, 149.6, 140.6, 138.5, 128.7, 128.1, 127.0, 118.3, 117.7, 114.3, 112.9, 80.6, 41.0, 28.4, 24.1, 13.7; HRMS (m/z): [M+H]$^+$ calcd for $C_{22}H_{26}N_3O_2S$, 396.1746. found, 396.1738.

Synthesis of R=N(Boc)$CH_2CH_2CH_2$COOH intermediate

In an $N_2$ atmosphere, 40 (200 mg, 0.51 mmol) was added to a suspension of NaH (60% dispersion in mineral oil, 24 mg, 0.6 mmol) in DMF (5 mL) and the mixture was stirred for 2 hr at room temperature. Then NaI (91 mg, 0.6 mmol) and ethyl 4-bromobutyrate (0.12 g, 0.6 mmol) in DMF (2 mL) were added. After being stirred for 18 h, the reaction mixture was poured into water (20 mL) and was extracted with EtOAc (2×50 mL). The combined extracts were dried over $Na_2SO_4$, and concentrated. The crude product was chromatographed ($SiO_2$, 2:1 hexane:AcOEt) to provide 11 (35 mg, 13%) as a yellow oil. Then to a solution of 11 (30 mg, 2.9 mmol) in THF (1 mL) and MeOH (0.5 mL) was added 2 N aqueous NaOH solution (0.2 mL). After being stirred at room temperature for 18 h, the reaction mixture was concentrated under reduced pressure, then diluted with EtOAc (10 mL) and washed with saturated $NH_4Cl$ solution (5 mL). The aqueous wash was extracted with EtOAc (2×10 mL), and the combined EtOAc layers were dried over $Na_2SO_4$ and concentrated. The crude product was chromatographed ($SiO_2$, EtOAc) to provide 14 mg of the R=N(Boc)$CH_2CH_2CH_2$COOH intermediate (50%) as a white foam. $^1$H NMR (300 MHz, $CDCl_3$): δ 8.69 (d, J=5.1 Hz, 1H), 7.95 (d, J=8.4 Hz, 2H), 7.80 (s, 1H), 7.73 (d, J=5.1 Hz, 1H), 7.53 (s, 1H), 7.51 (d, J=8.4 Hz, 2H), 6.58 (s, 1H), 2.92 (m, 4H), 2.33 (m, 2H), 1.90 (m, 4H), 1.50 (s, 9H), 1.02 (t, J=7.5 Hz, 3H); $^{13}$C NMR (75 MHz, $CDCl_3$): δ 174.2, 162.9, 156.3, 152.9, 149.6, 140.6, 138.5, 129.3, 128.9, 127.2, 119.0, 117.9, 114.8, 113.3, 80.8, 41.0, 40.3, 32.1, 28.4, 24.1, 21.1, 13.7; HRMS (m/z): [M+H]$^+$ calcd for $C_{26}H_{32}N_3O_4S$, 482.2114. found, 482.2120.

Synthesis of 4-(4-(2-(2-propylpyridin-4-yl)thiazol-4-yl)phenylamino)-N-isopropyl butanamide To a solution of the R=N(Boc)$CH_2CH_2CH_2$COOH intermediate (17 mg, 0.035 mmol), triethylamine (17 μl, 0.14 mmol) and isopropylamine (4 μL, 0.046 mmol) in DMF (0.5 mL) was HATU (16 mg, 0.042 mmol). After being stirred for 18 h, the reaction mixture was concentrated under reduced pressure, and the residue was partitioned between EtOAc (20 mL) and saturated $NH_4Cl$ solution (10 mL). The aqueous phase was extracted with EtOAc (2×10 mL). The combined extracts were washed with saturated $NaHCO_3$ solution, dried over $Na_2SO_4$, and concentrated. The crude product was chromatographed ($SiO_2$, 2:1 hexane:EtOAc) to afford the N-Boc protected 4-(4-(2-(2-propylpyridin-4-yl)thiazol-4-yl)phenylamino)-N-isopropyl butanamide (14 mg, 77%) as a yellow oil. Then to a solution of 13 (12 mg, 2.9 mmol) in THF (1 mL) was added TFA (0.2 mL). After being stirred at room temperature for 18 h, the reaction mixture was concentrated under reduced pressure, then diluted with EtOAc (20 mL) and washed with saturated $NH_4Cl$ solution (10 mL). The aqueous wash was extracted with EtOAc (2×5 mL), and the combined EtOAc layers were dried over $Na_2SO_4$ and concentrated. The crude product was chromatographed ($SiO_2$, 2:1 hexane:EtOAc) to provide 6.2 mg of 4-(4-(2-(2-propylpyridin-4-yl)thiazol-4-yl)phenylamino)-N-isopropyl butanamide (63%) as a yellow foam. $^1$H NMR (300 MHz, $CDCl_3$): δ 8.69 (d, J=5.4 Hz, 1H), 8.04 (1H, s), 7.96 (d, J=8.7 Hz, 2H), 7.96 (s, 1H), 7.72 (d, J=5.4 Hz, 1H), 7.51 (s, 1H), 6.65 (d, J=8.7 Hz, 2H), 3.95 (m, 1H), 3.03 (m, 4H,), 2.35 (m, 2H), 1.92 (m, 4H), 1.25 (d, J=6.3 Hz, 6H), 1.03 (t, J=7.5 Hz, 3H); $^{13}$C NMR (75 MHz, $CDCl_3$): δ 171.6, 162.9, 156.3, 152.9, 140.6, 138.5, 129.3, 128.9, 127.2, 119.0, 117.9, 114.8, 113.3, 42.2, 41.0, 40.3, 32.1, 24.1, 23.2, 21.1, 13.7; HRMS (m/z): [M+H]$^+$ calcd for $C_{24}H_{31}N_4OS$, 423.2219. found, 423.2216.

Synthesis of fatostatin-polyproline Linker-Biotin Conjugate

Fatostatin-KPGQFLYELKKPPPPPPPPPKK (SEQ ID NO: 15)-aminocaproic acid-biotin. Conjugates were synthesized on Rink-Amide MBHA resin by coupling N-α-Fmoc-protected amino acids, N-ε-Fmoc-ε-aminocaproic acid, R=N(Boc)$CH_2CH_2CH_2$COOH intermediate, biotin, purified by a reversed phase HPLC as described (Sato et al., 2007). Conjugate 3: calcd for $C_{155}H_{238}N_{35}O_{29}S_2^+$ requires 3119.9. Found (MALDI-TOF-MS) 3119.7 [M+H]$^+$.

Plasmids. pSRE-Luc, pCMV-SREBP-1c(1-436), pCMV-PLAP-BP2(513-1141) and pCMV-SCAP were gifts from J. L. Goldstein and M. S. Brown (University of Texas Southwestern Medical Center) (Sakai et al., 1998; Hua et al., 1995).

Antibodies. Monoclonal anti-SREBP-1 IgG (2A4), anti-SCAP IgG (9D5) and anti-ATF6 IgG (H-280) were purchased from Santa Cruz Biotechnology. Monoclonal anti-SREBP-2 IgG-7D4 was a gift from J. L. Goldstein and M. S. Brown (University of Texas Southwestern Medical Center). Polyclonal anti-FAS, anti-ACC, anti-SCD1 and anti-ACL IgG were purchased from BD Biosciences.

Cell culture. Chinese hamster ovary cells K1 (CHO-K1) cells were maintained in a Dulbecco's modified Eagle's medium/Ham's F12 medium [1:1] with 5% fetal bovine serum, 100 units/mL penicillin, and 100 μg/mL streptomycin sulfate at 37° C. under 5% $CO_2$. Human androgen-independent prostate cancer cells (DU145) were maintained in an Eagle's minimum essential medium containing 2 mM L-glutamine, 1.0 mM sodium pyruvate, 0.1 mM nonessential amino acids, and 1.5 g/L sodium biocarbonate with 10% fetal bovine serum, 100 units/mL penicillin, and 100 μg/mL streptomycin sulfate at 37° C. under 5% $CO_2$.

Preparation of cell membrane fraction. Cells were harvested, and then resuspended in buffer (10 mM Hepes•KOH (pH 7.4), 10 mM KCl, 1.5 mM $MgCl_2$ and 1 mM sodium EDTA), passed through a 22-gauge needle, and centrifuged at 1,000×g for 5 min. The postnuclear supernatants then were centrifuged at 15,000×g for 30 min, and the supernatant was removed.

Oligonucleotide microarray analysis. DU145 prostate cancer cells were treated with 5 mM of fatostatin or DMSO alone in the presence of 1 μg/mL of IGF1 for 6 hrs in a serum free medium, total RNA was extracted in a TRI reagent (Molecular Research Center) and further isolated by RNeasy Mini Kit (Qiagen). Purified mRNA was analyzed by Baylor College of Medicine Microarray Core Facility by Affymetrix Human Genome U133 Plus 2.0 Array consisting of almost 45,000 probe sets representing more than 39,000 transcripts derived from approximately 33,000 well-substantiated human genes (Affymetrix, Inc.).

RT-PCR experiments. Total RNA was extracted from DU145 cells in TRI reagent (Molecular Research Center) and isolated with an RNeasy Mini Kit (Qiagen). The RNA sample was subjected to RT-PCR by using the Access RT-PCR System (Promega). RT-PCR reactions contained total RNA, 1 μM of each primer, 0.2 mM dNTP, 1 mM $MgSO_4$, AMV reverse transcriptase (2 units), and Tfl DNA polymerase (2 units) in a final volume of 25 μL. The primer pairs used are as follows: 5'-TCA GAC CGG GAC TGC TTG GAC GGC TCA GTC-3' (SEQ ID NO: 16) and 5'-CCA CTT AGG CAG TGG AAC TCG AAG GCC G-3' (SEQ ID NO: 17) for Low density lipoprotein receptor (LDLR); 5'-GCC TGC TTG ATA ATA TAT AAA C-3' (SEQ ID NO: 18) and 5'-CAC TTG AAT TGA GCT TTA G-3' (SEQ ID NO: 19) for stearoyl-CoA desaturase (SCD); 5'-AAG AAA AAG TGT CAG ACA GCT GG-3' (SEQ ID NO: 20) and 5'-TGG ACT GAA GGG GTG TTA GC-3' (SEQ ID NO: 21) for ATP citrate lyase (ACL); 5'-GCC CGA CAG TTC TGA ACT GGA ACA-3' (SEQ ID NO: 22) and 5'-GAA CCT GAG ACC TCT CTG AAA GAG-3' (SEQ ID NO: 23) for 3-hydroxy-3-methylglutaryl-CoA reductase (HMG-CoAR); 5'-CTG CCT GAC TGC CTC AGC-3' (SEQ ID NO: 24) and 5'-ACC TCT CCT GAC ACC TGG G-3' (SEQ ID NO: 25) for mevalonate pyrophosphate decarboxylase (MVD); 5'-AAG ACT TCA GGG TAA GTC ATC A-3' (SEQ ID NO: 26) and 5'-CGT GTA TAA TGG TGT CTA TCA G-3' (SEQ ID NO: 27) for insulin induced gene 1 (INSIG1). The amplification conditions are as follows: 1 cycle at 94° C. for 4 min, then denatured at 94° C. for 40 s, annealed at 50° C. for 40 s, and extended at 68° C. for 2 min with 22 cycles for SCD and HMG CoA R, annealed at 58° C. with 24 cycles for LDLR and INSIG1, or annealed at 60° C. with 24 cycles for ACL, annealed at 55° C. with 30 cycles for MVD. The amplified DNAs were analyzed by an agarose gel and quantified with the Scion-image software.

PLAP-BP2 Cleavage. On day 0, CHO-K1 cells were plated out onto a 96-well plate in medium A. On day 2, the cells were transiently co-transfected with pCMV-PLAP-BP2(513-1141), pCMV-SCAP and pAc-3-gal, using Lipofectamine reagent (Invitrogen). After incubation for 5 h, the cells were washed with PBS, and then incubated, in the absence or presence of fatostatin (20 μM) or sterols (10 μg/mL cholesterol and 1 μg/mL 25-hydroxycholesterol), in medium B. After 20 h of incubation, an aliquot of the medium was assayed for secreted alkaline phosphatase activity. The cells in each well were lysed, and used for measurement of β-galactosidase activities. The alkaline phosphatase activity was normalized by the activity of β-galactosidase.

Enzymatic activities and western blot analyses. A portion of the frozen liver was ground to powder in liquid nitrogen. The powdered tissues were suspended in 10 mL of PBS containing 0.1 mM PMSF, 5 mM benzamidine, and 5 mg/mL protease inhibitor cocktail (Roche), and homogenized using Polytron (3×30 Sec, at high speed), and sonicated briefly to degrade DNA. The extracts were clarified by centrifugation at 16,000×g for 20 min. Protein concentrations in the supernatant were determined, and subjected to western blot analysis using antibodies against FAS, ACC, SCD1 and ACL. The intensity of the specific bands of proteins of interest were scanned and normalized against b-actin for quantifications. FAS and ACC activities from the liver extracts were determined as described earlier (Mao et al., 2006).

Example 11

Figure 26:
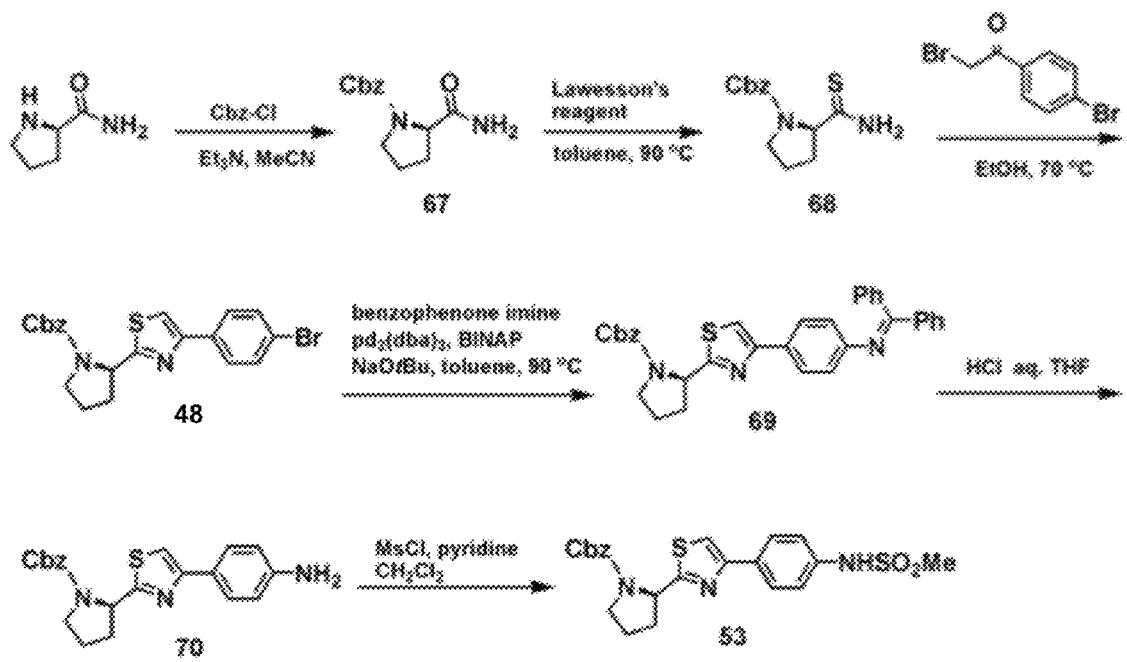
FIG. 26 provides a synthetic scheme of compound 53.

Synthesis of benzyl (R)-2-(4-(4-(methylsulfonamido)phenyl)thiazol-2-yl)pyrrolidine-1-carboxylate As shown in FIG. 26, to a solution of L-prolinamide (1.14 g, 10.0 mmol) in acetonitrile (100 mL) were added benzyl chloroformate (1.55 mL, 11.0 mmol) and triethylamine (2.79 mL, 20 mmol) at rt. The mixture was stirred at rt for 12 h and diluted with AcOEt. The mixture was poured into 0.1 M HCl solution and separated between the organic layer and the aqueous layer. The organic layer was washed with sat. aq. $NaHCO_3$ and brine, dried ($Na_2SO_4$), filtered, and concentrated. The residue was purified by silica gel column chromatography to give 67 (2.26 g, 91%) as colorless oil.

A mixture of 67 (586 mg, 2.36 mmol) and Lawesson's reagent (1.05 g, 2.60 mmol) in toluene (30 mL) was stirred at 90° C. for 1 h. After cooling to rt, the solvent was evaporated. The residue was purified by silica gel column chromatography to give 68 (495 mg, 79%) as a white amorphous solid.

A mixture of 68 (300 mg, 1.13 mmol) and 4-bromophenacyl bromide (318 mg, 1.13 mmol) in EtOH (10 mL) was stirred under reflux for 2 h. After evaporated, the residue was purified by silica gel column chromatography to give 48 (265 mg, 53%) as a white solid.

A mixture of 48 (230 mg, 0.519 mmol), $Pd_2(dba)_3$ (9.50 mg, 2 mol %), BINAP (97%, 20.0 mg, 6 mol %), sodium t-butoxide (69.8 mg, 0.727 mmol), and benzophenone imine (0.105 mL, 0.623 mmol) in toluene (5.0 mL) under reflux for 8 h. After cooling to rt, the mixture was filtered through Celite and the filtrate was evaporated. The residue was purified by silica gel column chromatography to give 69 (228 mg, 81%) as a yellow amorphous solid.

To a solution of 69 (175 mg, 0.321 mmol) in THF (3 mL) was added aqueous HCl solution (4 M, 0.3 mL) and the mixture was stirred at rt for 1 h. The mixture was neutralized with sat. aq. $NaHCO_3$ and extracted with AcOEt. The organic layer was washed with brine, dried ($Na_2SO_4$), filtered, and concentrated. The residue was purified by silica gel column chromatography to give 70 (113 mg, 93%) as a colorless oil.

A mixture of 70 (92 mg, 0.24 mmol), methanesulfonyl chloride (0.021 mL, 0.27 mmol), and pyridine (0.043 mL, 0.53 mmol) in $CH_2Cl_2$ (2 mL) was stirred at rt for 8 h. After addition of MeOH, the mixture was diluted with AcOEt and washed with sat. aq. NaHCO$_3$ and brine. The organic layer was dried (Na$_2$SO$_4$), filtered, and concentrated. The residue was purified by silica gel column chromatography to give 53 (91 mg, 83%) as a white solid.

$^1$H NMR (CDCl$_3$, 600 MHz, two rotamers, ratio=1:0.95) δ 7.80-7.86 (m, 2H), 7.14-7.41 (m, 7H), 6.64 (s, 1H, major rotamer), 6.83 (s, 1H, minor rotamer), 5.07-5.36 (m, 3H), 3.73 (m, 1H), 3.59 (m, 1H), 3.03 (s, 3H, major rotamer), 3.00 (s, 3H, minor rotamer), 2.28-2.39 (m, 2H), 2.00-2.10 (m, 2H); $^{13}$C NMR (CDCl$_3$, 150 MHz, two rotamers, major peaks are shown) 174.7, 155.4, 154.4, 136.4, 131.9, 128.5, 128.3, 127.9, 127.8, 127.7, 127.7, 120.8, 112.3, 67.1, 59.4, 47.2, 39.4, 32.9, 23.1; HRMS (FAB): Exact mass calcd. for C$_{22}$H$_{24}$N$_3$O$_4$S$_2$ [M+H]$^+$, 458.1203. Found 458.1200.

Example 12

Synthesis of N-(4-(2-(2-propylpyridin-4-yl)thiazol-4-yl)phenyl)methanesulfonamide (19)

Figure 27:
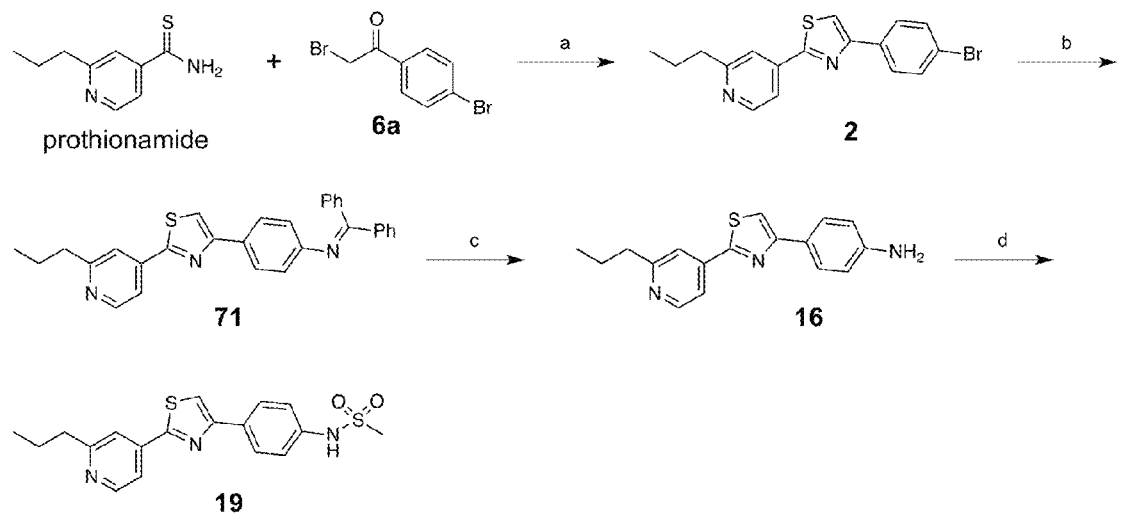
FIG. 27 provides a synthetic scheme of compound 19.

As shown in FIG. 27, in reaction (a) a mixture of prothionamide (9.01 g, 50.0 mmol) and 4-bromophenacyl bromide 6a (13.9 g, 50.0 mmol) in EtOH (400 mL) was stirred at 70° C. for 1 h. After cooled to room temperature, the precipitation was filtered off with EtOAc and washed with EtOAc and saturated aqueous NaHCO$_3$. The organic layer was washed with brine, dried over Na$_2$SO$_4$, and concentrated to give 4-(4-bromophenyl)-2-(2-propylpyridin-4-yl)thiazole 2 (14.3 g, 79%) as a light-yellow solid.

In reaction (b) a pressure tube was charged with 2 (1.08 g, 3.0 mmol), benzophenone imine (0.57 g, 3.3 mmol), Pd$_2$dba$_3$ (86 mg, 0.15 mmol), BINAP (280 mg, 0.45 mmol), sodium tert-butoxide (1.44 g, 9.0 mmol), and dry toluene (30 mL) and purged with argon gas. The pressure tube was sealed and heated in a 100° C. bath for 20 hrs. After being cooled to room temperature, the reaction mixture was chromatographed (SiO$_2$, 4:1 hexane:EtOAc) to provide 1.35 g of 71 (98%) as a yellow oil.

In reaction (c) then to a solution of 71 (1.35 g, 2.9 mmol) in THF (20 mL) was added 2 M aqueous HCl solution (15 mL). After being stirred at room temperature for 2 hrs, the reaction mixture was concentrated under reduced pressure, then diluted with EtOAc (100 mL) and washed with saturated Na$_2$CO$_3$ (50 mL) solution. The aqueous wash was extracted with EtOAc (3×40 mL), and the combined EtOAc layers were dried over Na$_2$SO$_4$ and concentrated. The crude product was chromatographed (SiO$_2$, 4:1 hexane:EtOAc) to provide 0.73 g of 4-(2-(2-propylpyridin-4-yl)thiazol-4-yl)benzenamine 16 (82%) as a white crystal.

$^1$H NMR (600 MHz, CDCl$_3$): δ 8.61 (d, J=4.8 Hz, 1H), 7.80 (d, J=8.9 Hz, 2H), 7.75 (d, J=1.4 Hz, 1H), 7.67 (dd, J=1.4, 4.8 Hz, 1H), 7.36 (s, 1H), 6.75 (d, J=8.9 Hz, 2H), 3.82 (brs, 1H), 2.85 (t, J=7.6 Hz, 2H), 1.83 (m, 2H), 1.01 (t, J=7.6 Hz, 3H); $^{13}$C NMR (150 MHz, CDCl$_3$): δ 164.9, 163.4, 157.3, 150.0, 146.8, 140.8, 127.7, 124.8, 119.2, 117.8, 115.1, 111.3, 40.4, 23.1, 13.9; HRMS (m/z): [M+H]+ calcd for C$_{17}$H$_{18}$N$_3$S, 296.1221. found, 296.1228.

In reaction (d) methanesulfonyl chloride (0.23 mL, 2.97 mmol) was added to a stirred solution of 16 (800 mg, 2.71 mmol) and pyridine (0.66 mL, 8.1 mmol) in CH$_2$Cl$_2$ (20 mL) at 0° C. After being stirred for 0.5 h, the mixture was poured into 2 M citric acid solution and extracted with EtOAc. The combined extracts were washed with saturated NaHCO$_3$ solution and brine, dried over Na$_2$SO$_4$, and concentrated to produce N-(4-(2-(2-propylpyridin-4-yl)thiazol-4-yl)phenyl)methanesulfonamide 19 (880 mg, 87%) as a yellow foam.

$^1$H NMR (300 MHz, CD$_3$OD): δ 8.55 (d, J=5.2 Hz, 1H), 8.02 (d, J=8.8 Hz, 2H), 7.95 (s, 1H), 7.90 (d, J=1.9 Hz, 1H), 7.84 (dd, J=1.9, 5.2 Hz, 1H), 7.34 (d, J=8.8 Hz, 2H), 3.00 (s, 3H), 2.86 (t, J=7.7 Hz, 2H), 1.80 (m, 2H), 1.01 (t, J=7.3 Hz, 3H). m/z=374 [M+H]$^+$.

Example 13

SREBP Activation Assays for Compounds 45-66

Figure 28:
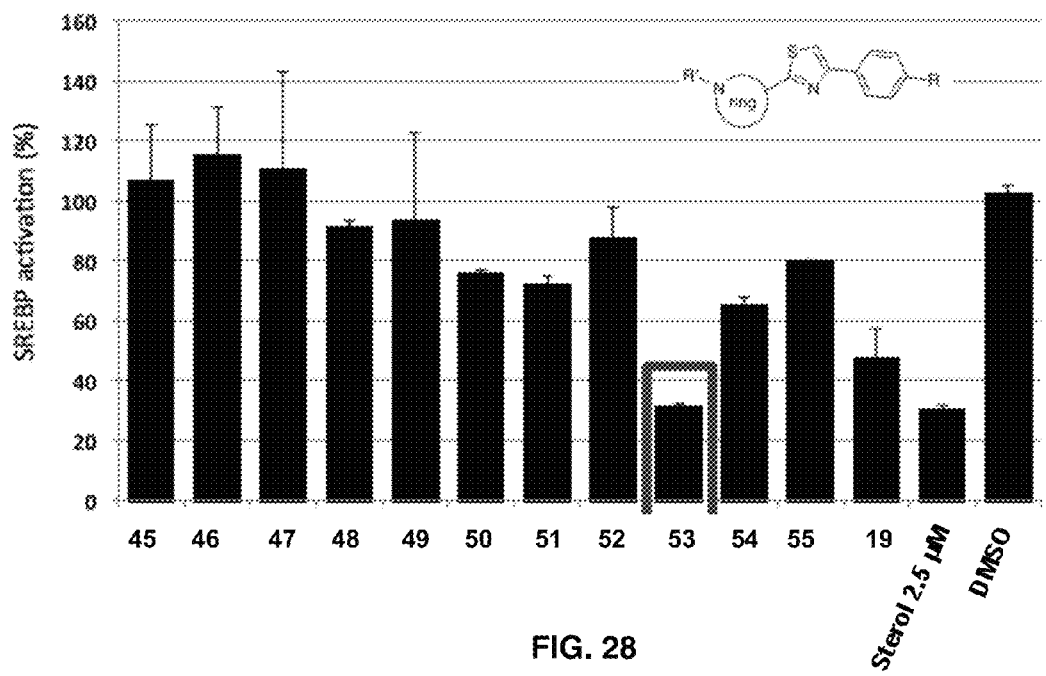
FIG. 28 shows a standard SREBP activation assay with exemplary analogues 45-55 and 19.
Figure 29:
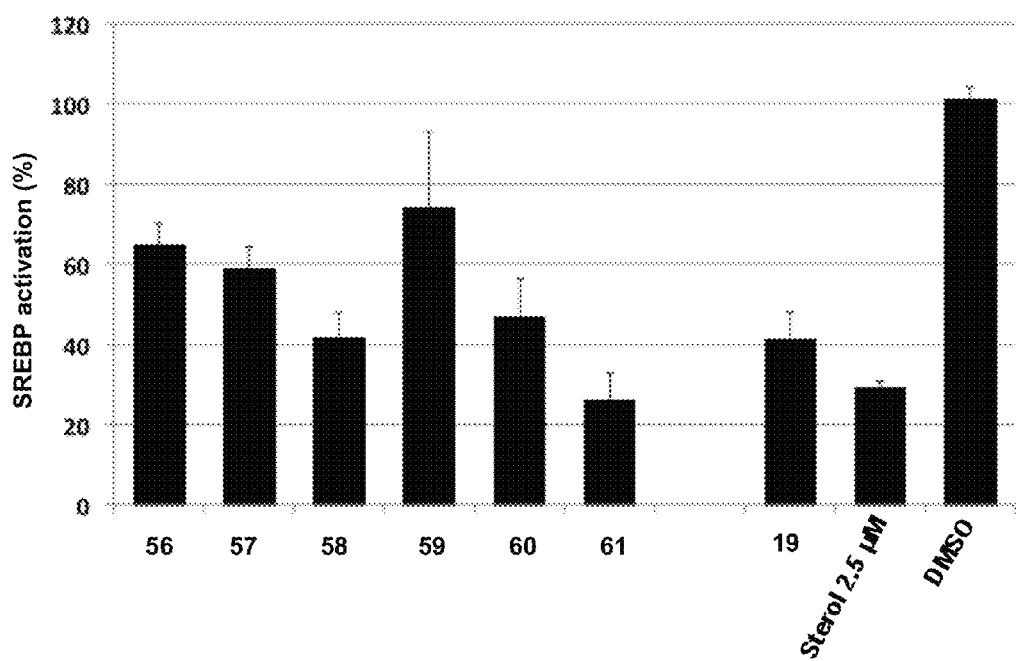
FIG. 29 shows a standard SREBP activation assay with exemplary analogues 56-61 and 19.
Figure 30:
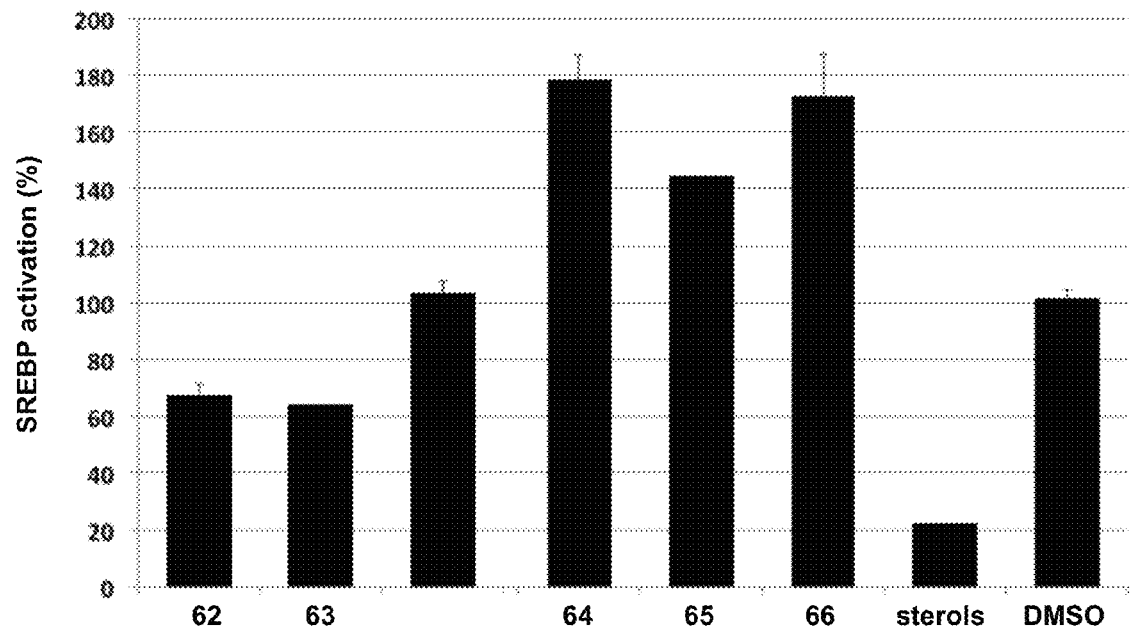
FIG. 30 shows a standard SREBP activation assay with exemplary analogues 62-66.
Figure 31:
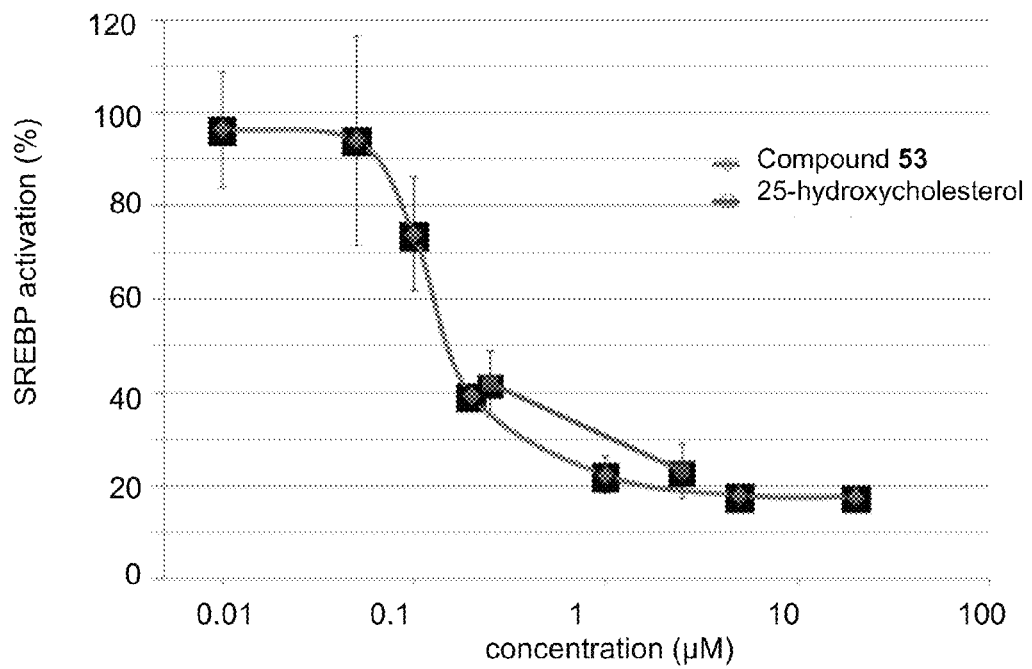
FIG. 31 shows an Inhibitory Concentration (sub 50) data of exemplary compound 53.
Figure 32:
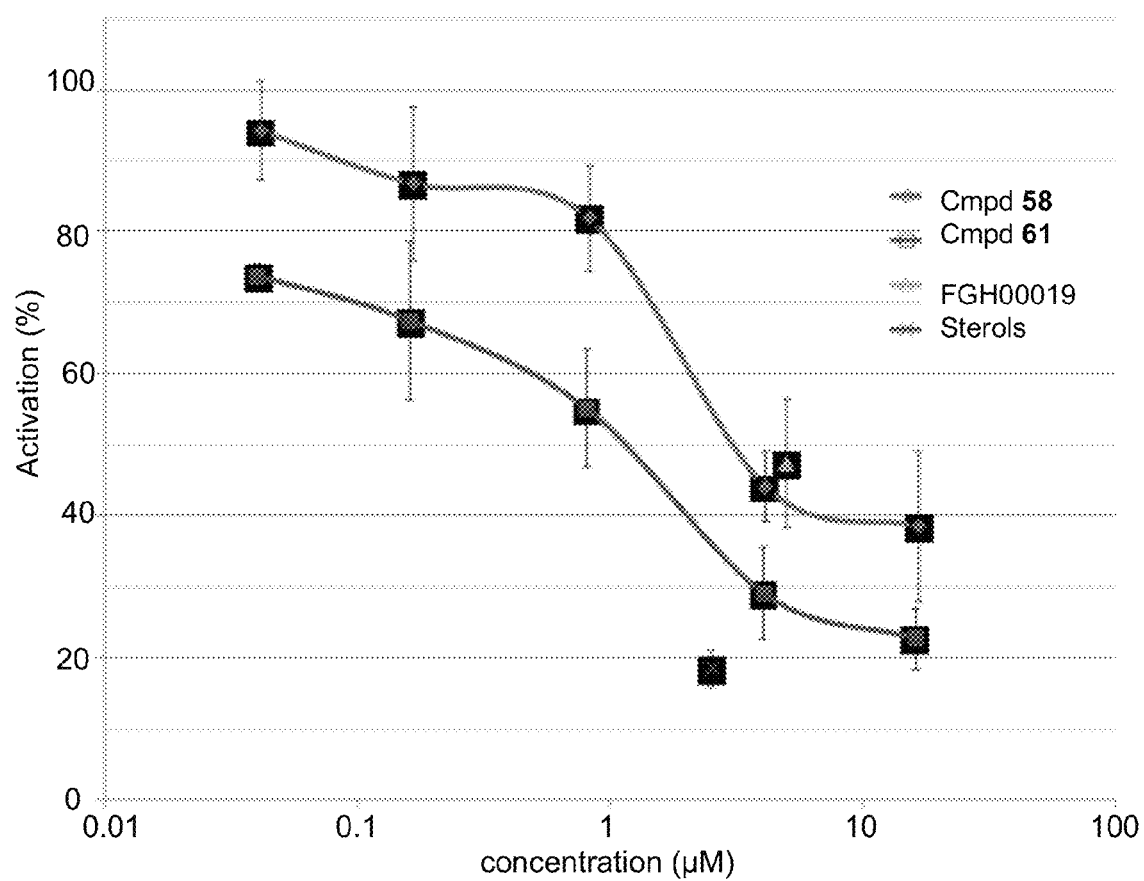
FIG. 32 shows an Inhibitory Concentration (sub 50) data of exemplary compounds 58 and 61.

Standard SREBP activation assays were performed on the exemplary compounds identified in Table 4 as per the method for Fatostatin A in Example 1. The ability of endogenous SREBPs to activate transcription of an SREBP-responsive reporter gene was measured in the presence or absence of compounds 45-55 and 19 (FIG. 28), compounds 56-61 and 19 (FIG. 29) and compounds 62-66 (FIG. 30) at 5 µM in CHOK1 cells. Of these, compound 61 demonstrated inhibition of SREBP activation at about 25%, with compound 53 at about 30%, compound 58 at about 42%, and compound 19 at about 45%. The inhibitory concentrations of compounds 53 (FIG. 31) and compounds 58 and 61 (FIG. 32) were determined.

The following references are cited herein.

Abu-Elheiga et al., (2001) Science 291, 2613-6.
Abu-Elheiga, L. et al., (2003) Proc Natl Acad Sci USA 100, 10207-12.
Abu-Elheiga, L. et al., (1997) J Biol Chem 272, 10669-10677.
Abu-Elheiga, L. et al., (2000) Proc. Natl. Acad. Sci. USA 97, 1444-1449.
Abu-Elheiga, L. et al., (1995) Proc. Natl. Acad. Sci. USA 92, 4011-4015.
Boden G, C. X. et al., (1994) J Clin Invest. 93(6):2438-46 93(6), 2438-2446.
Boizard, M. et al., (1998) J Biol Chem 273, 29164-71.
Brown, M. S. et al., (1997) Cell 89, 331-40.
Chalkley, S. M. et al., (1998) Metabolism 47(9), 1121.
Choi, Y. et al., (2003) J Biol Chem 278, 7320-4.
Cohen, P. et al., (2002) Science 297(5579), 240-243.
Goldstein, J. L. et al., (1983) Methods Enzymol 98, 241-60.
Goldstein, J. L. et al., (2006) Cell 124, 35-46.
Grand-Perret, T. et al., (2001) Nat Med 7, 1332-8.
Hastings, N. et al., (2001) Proc. Natl. Acad. Sci. USA 98(25), 14304-14309.
Hookman et al., (2003) American Journal of Gastroenterology 98(9), 2093-2097.
Horton, J. D. et al., (1998) Proc Natl Acad Sci USA 95, 5987-92.
Horton, J. D., et al., (2003) Proc Natl Acad Sci USA 100, 12027-32.
Horton, J. D. et al., (2003) J. Biol. Chem. 278(38), 36652-36660.
Hua, X. et al. et al., (1996) Cell 87, 415-26.
Hua, X. et al., (1995) J Biol Chem 270, 29422-29427.
Ingalis, A. M. et al., (1950) J. Hered 41, 317-318.
Kim, J. B. et al., (1996) Genes Dev 10, 1096-107.
Ktorza A, B. C. et al., (1997) Diabetes Metab. Suppl 2, 38-46.
Kubota N, T. Y., et al. (1999) Mol. Cell 4, 597-609.
Liang, G., et al., (2002) J Biol Chem 277, 9520-8.
Mao, J. et al., (2006) Proc Natl Acad Sci USA 103, 8552-7.
Marquardt, A., et al., (2000) Genomics 66(2), 175.
Matsusue, K., et al., (2003) J. Clin. Invest. 111(5), 737-747.
Miyazaki, M., et al., (2000) J. Biol. Chem. 275(39), 30132-30138.
Moller, D. E. et al., (2005) Annual Review of Medicine 56(1), 45-62.
Nakamura, M. T. et al., (2004) Annual Review of Nutrition 24(1), 345-376.

Ntambi, J. M., et al., (2002) *Proc Natl Acad Sci USA* 99(17), 11482-11486.
Oh, W., et al., (2005) *Proc Natl Acad Sci USA* 102, 1384-9.
Osborne, T. F. (2000) *J Biol Chem* 275, 32379-82.
Rader, D. J. (2001) *Nat Med* 7, 1282-4.
Remington's Pharmaceutical Sciences, 18th Ed. Mack Printing Company, 1990.
Sakai, J. et al., (1996) *Cell* 85, 1037-46.
Sakai, J. et al. MMol Cell 2, 505-14 (1998).
Sato, S. et al. *J Am Chem Soc* 129, 873-80 (2007).
Sheng, et al., (1995) *Proc Natl Acad Sci USA* 92, 935-938.
Shimano, H. (2000) *Trends Cardiovasc Med* 10, 275-8.
Shimano, H., et al., (1999) *J Biol Chem* 274, 35832-9.
Tontonoz, P., et al., (1993) *Mol Cell Biol* 13, 4753-9.
Yahagi, N., et al., (2002) *J. Biol. Chem.* 277(22), 19353-19357.
Zambrowicz, B. P et al., (2003) *Nat Rev Drug Discov.* 2(1), 38-51.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, composition of matter, means, methods and steps described in the specification. As one of ordinary skill in the art will readily appreciate from the disclosure of the present invention, processes, compositions of matter, means, methods, or steps, presently existing or later to be developed that perform substantially the same function or achieve substantially the same result as the corresponding embodiments described herein may be utilized according to the present invention.

What is claimed is:

1. A compound with a chemical structure:

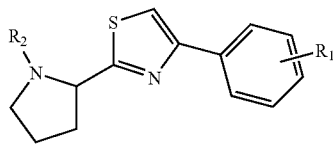

wherein $R_1$ is H, halogen, —OH, —O—$C_{1-3}$ alkoxy, —OC(O)$R_3$ or —NHR$_5$;

$R_3$ is $C_1$-$C_3$ alkyl or aryl, —OCH$_2$—C(O)OR$_4$;

$R_4$ is H or $C_1$-$C_3$ alkyl;

$R_5$ is H, $C_1$-$C_4$ alkyl, alkylcyclopropane, benzyl, —NHC(O)$C_1$-$C_3$ amide, —NHC(O)O—$R_6$ carbamate;

$R_6$ is tert-butyl or fluorenylmethyl or —NH—SO$_2$—$R_7$ sulfonamide;

$R_7$ is alkyl or aryl, $R_2$ is alkyl or $R_8$OC(O)— and $R_8$ is $C_3$-$C_5$ alkyl or aryl.

2. The compound of claim 1, wherein said halogen is bromine.

3. A pharmaceutical composition comprising the compound of claim 1 and a pharmaceutically acceptable excipient.

4. A method for treating a metabolic disorder in an individual, comprising the step of:

administering to the individual a therapeutically effective amount of at least one compound of claim 1, or a pharmaceutically acceptable salt or a stereoisomer thereof or a combination thereof.

5. The method of claim 4, wherein said metabolic disorder comprises obesity, hyperlipemia, diabetes or complications thereof, fatty liver, hypertension prostate, cancer or cardiovascular disease.

6. The method of claim 4, further comprising the step of: providing an additional therapy to said individual.

7. The method of claim 6, wherein the additional therapy comprises dietary therapy, physical therapy, behavior therapy, surgery, drug therapy or a combination thereof.

8. A kit comprising:
the compound of claim 1; and
a container housing the compound.

9. A compound that is:
tert-butyl 2-(4-(4-bromophenyl)thiazol-2-yl)pyrrolidine-1-carboxylate,
benzyl-2-(4-(4-bromophenyl)thiazol-2-yl)pyrrolidine-1-carboxylate,
4-(4-bromophenyl)-2-(pyrrolidin-2-yl)thiazole,
4-(4-bromophenyl)-2-(1-propylpyrrolidin-2-yl)thiazole,
benzyl-(R)-2-(4-(4-(methylsulfonamido)phenyl)thiazol-2-yl)pyrrolidine-1-carboxylate.

* * * * *